(12) United States Patent
Berosik et al.

(10) Patent No.: US 10,913,944 B2
(45) Date of Patent: Feb. 9, 2021

(54) METHODS, SYSTEMS AND COMPOSITIONS THEREOF FOR NUCLEIC ACID LIBRARY QUALITY CONTROL AND QUANTIFICATION

(71) Applicant: Life Technologies Corporation, Carlsbad, CA (US)

(72) Inventors: Stephan Berosik, Carlsbad, CA (US); Jianbo Gao, Carlsbad, CA (US); Shiaw-Min Chen, Carlsbad, CA (US); H. Michael Wenz, Carlsbad, CA (US)

(73) Assignee: Life Technologies Corporation, Carlsbad, CA (US)

( * ) Notice: Subject to any disclaimer, the term of this patent is extended or adjusted under 35 U.S.C. 154(b) by 392 days.

(21) Appl. No.: 15/542,795

(22) PCT Filed: Jan. 11, 2016

(86) PCT No.: PCT/US2016/012785
§ 371 (c)(1),
(2) Date: Jul. 11, 2017

(87) PCT Pub. No.: WO2016/115001
PCT Pub. Date: Jul. 21, 2016

(65) Prior Publication Data
US 2020/0140855 A1    May 7, 2020

Related U.S. Application Data

(60) Provisional application No. 62/102,518, filed on Jan. 12, 2015.

(51) Int. Cl.
*C12Q 1/6806* (2018.01)
*C12N 15/10* (2006.01)

(52) U.S. Cl.
CPC ....... *C12N 15/1093* (2013.01); *C12Q 1/6806* (2013.01)

(58) Field of Classification Search
None
See application file for complete search history.

(56) References Cited

FOREIGN PATENT DOCUMENTS

WO    WO 99/003872    1/1999

OTHER PUBLICATIONS

Gu et al., "Production of Single-Stranded DNAs by Self-Cleavage of Rolling-Circle Amplification Products," Biotechniques, 2013, 54(6):337-343.
Pmiguel, "Single Stranded Molecules Run Crazy Slow on a DNA Agilent Chip," 2002, http://seqanswers.com/forums/showthread.php?t=12852.
Pmiguel, "dsDNA Migrates Crazy Fast on Pico RNA Chip," 2011, http://seqanswers.com/forums/showthread.php?t=12501.
International Search Report for PCT/US2016/012785, dated Jul. 27, 2016, 12 pages.

*Primary Examiner* — Christopher M Gross
(74) *Attorney, Agent, or Firm* — McNeill Baur PLLC

(57) ABSTRACT

Methods, systems, kits and compositions are described for quality control and quantitation of nucleic acid libraries of double stranded nucleic acid libraries prior to massively parallel sequencing. Electrophoretic separation within a channel using a detectably labeled single stranded sizing ladder may be used to define the molecular weight range and amount of the double stranded nucleic acids.

20 Claims, 24 Drawing Sheets
Specification includes a Sequence Listing.

| No. | Size | Area | Ratio | Start | End |
|---|---|---|---|---|---|
| 1 | 202 | 1835406 | 91.255 | 2994 | 3831 |
| 2 | 4810 | 1138546 | 56.608 | 12192 | 13213 |

FIG. 4

METHODS, SYSTEMS AND COMPOSITIONS THEREOF FOR NUCLEIC ACID LIBRARY QUALITY CONTROL AND QUANTIFICATION

This application claims priority to International Patent Application No. PCT/US2016/012785, filed Jan. 11, 2016, which claims priority to U.S. Provisional Application No. 62/102,518, filed Jan. 12, 2015, the disclosures of which are hereby incorporated by reference in its entirety for all purposes.

The present application contains a Sequence Listing in electronic format. The Sequence Listing is provided as a file entitled "2018-10-01_01129-0048-00US_ST25.txt" created on Oct. 1, 2018, which is 1,819 bytes in size.

Next-Generation Sequencing (NGS) work flow requires good library construction in order to provide successful results in massively parallel sequencing strategies. The requirements for a good DNA library includes a requirement that the plurality of double stranded nucleic acids produced in the preliminary steps of the workflow are of a pre-selected range of lengths, including primer and adapter sequences, and must be quantitated sufficiently to determine effective library loading into the sequencing step to thereby generate good sequencing data in a NGS workflow. Improved workflows, simpler instrumentation demand, and increased sensitivity of detection are needed. The methods described here may be applied to any plurality of double stranded nucleic acids, obtained from any method, that requires knowledge of the range of lengths and amount of material contained in that plurality, and is no way limited to NGS libraries.

SUMMARY

In a first aspect, a method for determining a range of lengths of a plurality of double stranded nucleic acids is provided including the steps of contacting the plurality of double stranded nucleic acids with a) a first dye, and b) a detectably labeled single stranded sizing ladder, under conditions where the first dye is configured to label a double stranded nucleic acid; producing a mixture comprising a plurality of first dye-labeled double stranded nucleic acids and the detectably labeled single stranded sizing ladder; migrating the mixture under mobility dependent separation conditions; separating each of the plurality of first dye-labeled double stranded nucleic acids; and determining a migration time of each of the plurality of first dye-labeled double stranded nucleic acids. In various embodiments, the method may further include determining a migration time of each of the plurality of fragments of the detectably labeled single stranded sizing ladder. The method may further include converting the migration time of each of the plurality of first dye-labeled double stranded nucleic acids to a length. In some embodiments, the converting step may include a step of comparing a migration time of the first dye-labeled double stranded nucleic acid to a migration time of at least one fragment of the detectably labeled single stranded sizing ladder. In some embodiments, comparing a migration time of the first dye-labeled double stranded nucleic acid to the migration time of the at least one fragment of the detectably labeled single stranded sizing ladder may include comparing the first dye-labeled double stranded nucleic acid migration time to a plurality of fragment migration times of the detectably labeled single stranded sizing ladder. In various embodiments, converting the migration time of each of the plurality of first dye-labeled double stranded nucleic acids may further include assigning a length of each first dye-labeled double stranded nucleic acid based on a correlation factor assigned to each fragment of the detectably labeled single stranded sizing ladder.

In various embodiments of the method, the plurality of double stranded nucleic acids may be ribonucleic acid having at least a partially double stranded structure.

In various embodiments of the method, the first dye may be configured to label at least a detectable portion of the plurality of double-stranded nucleic acids. In some embodiments, the first dye may be configured to label a substantial portion of the plurality of double stranded nucleic acids. In various embodiments, the first dye may label the plurality of double stranded nucleic acids noncovalently. In some embodiments, the first dye may label each of the plurality of double stranded nucleic acids non-covalently. In various embodiments, the first dye may label each of the plurality of double stranded nucleic acids as an intercalating dye.

In various embodiments of the method, the first dye may be configured to substantially not label a single stranded nucleic acid.

In various embodiments of the method, the first dye has a structure of Formula I:

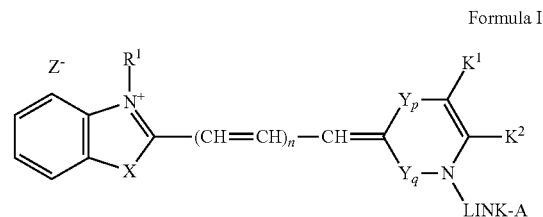

Formula I where X is O, S, Se, or $C(CH_3)$; $R^1$ is $C_1$-$C_6$ alkyl; n=0, 1 or 2; Y is $-CH_2=CH_2-$, where p and q are equal to 0 or 1, such that p+q=1; $K^1$ and $K^2$ are the same or different, and are independently hydrogen, an alkyl group having 1-6 carbons, or aryl; or $K^1$ and $K^2$ are taken in combination to complete a 6-membered aromatic ring to yield a quinolinium ring system; LINK is an aliphatic chain containing a backbone of 4 to 19 methylene groups ($-CH_2-$), which is optionally interspersed at one or more intervals with a heteroatom, each of which is independently N, O or S, wherein each N heteroatom is additionally substituted by 1-2 H, or 1-2 alkyl groups with 1 to 6 carbons, which alkyl substituents may be the same or different, provided that any heteroatom is separated from another heteroatom by at least 2 methylene groups, wherein one methylene terminus of LINK is attached to a nitrogen atom of the pyridinium or quinolinium heterocycle and another methylene terminus of LINK is attached to A, except that where A is H or $CH_3$, LINK must contain at least one N heteroatom; A is either H, $CH_3$ or has a structure of Formula A:

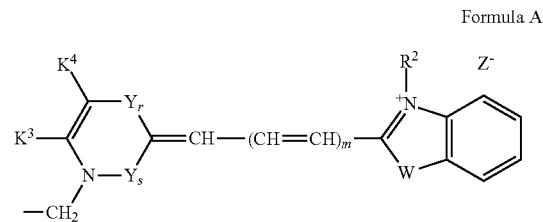

Formula A where W is O, S, Se, or C(CH$_3$); R$^2$ is C$_1$-C$_6$ alkyl; m=0, 1 or 2; Y is —CH$_2$=CH$_2$—, with subscripts r and s equal to 0 or 1, such that r+s=1; K$^3$ and K$^4$ may be the same or different, and are independently hydrogen, an alkyl group having 1-6 carbons, or aryl; or K$^3$ and K$^4$ are taken in combination to complete a 6-membered aromatic ring to yield a quinolinium ring system; when A is not H or CH$_3$, m and n can be the same or different; and W and X can be the same or different. In some embodiments, the first dye may be a cyanine dye of Formula I where X is O; R$^1$ is methyl; the methine bridge is monomethine, where n is 0; Y$_p$ has p=0 and Y$_q$ has q=1; K$^1$ and K$^2$ are taken together in combination to complete a 6 membered aromatic ring yielding a quinolinium ring system; LINK has a backbone of 9-12 methylene groups and interspersed at two intervals with a nitrogen atom, where each nitrogen atom is mono- or di-substituted with C$_1$-C$_6$ carbons, and further where the two nitrogen atoms are separated from each other by at least two methylene groups; A has a structure of Formula A:

Formula A

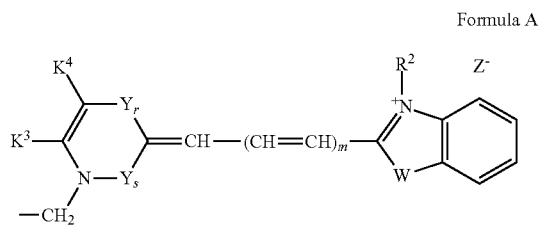

where W is O; R$^2$ is methyl; the methine bridge is monomethine where m=0; Y$_r$ has r=0 and Y$_s$ has s=1; and K$^3$ and K$^4$ are taken in combination to complete a 6 membered aromatic ring to yield a quinolinium ring system.

In various embodiments of the method, the mobility dependent separation may be performed in the presence of at least one denaturing additive. In some embodiments, the mobility dependent separation conditions may be configured to maintain at least a detectable amount of the first dye label labeling each of the plurality of double stranded nucleic acids. In various embodiments, the mobility dependent separation conditions may include a running temperature configured to maintain the at least detectable amount of first dye-labeled double stranded nucleic acid. In various embodiments, the running temperature may be a temperature wherein the plurality of first-dye labeled double stranded nucleic acids retains the first-dye labeling. In various embodiments, the mobility dependent separations conditions may substantially maintain the first dye-label labeling of at least a first portion of the plurality of first dye-labeled double stranded nucleic acids. In various embodiments, a proportion of each of the first dye labeled double stranded nucleic acids that is maintained under the mobility dependent separation conditions may be related to the migration time. In various embodiments, the mobility dependent separation conditions may include no denaturing additive. In various embodiments, the mobility dependent separation conditions may be configured to substantially maintain the first dye label labeling each of the plurality of double stranded nucleic acids.

In various embodiments of the method, the detectably labeled single stranded sizing ladder may be labeled covalently by a second dye. In various embodiments, the second dye may be spectrally resolvable from the first dye.

In various embodiments, the method may further include obtaining quantification of the plurality of double stranded nucleic acids by correlating one or more areas under the curve of at least a first plurality of detected peaks of the plurality of first dye-labeled double stranded nucleic acids with at least one or more areas under the curve of a second plurality of detected peaks of the fragments of the detectably labeled sizing ladder. In some embodiments, the at least first plurality of detected peaks of the plurality of first dye-labeled double stranded nucleic acids may be all of the detected peaks of the plurality of first dye-labeled double stranded nucleic acids.

In various embodiments, the method may further include summing all of the correlated areas under the curve of the plurality of the first dye-labeled double stranded nucleic acids, thereby providing quantification for the plurality of double stranded nucleic acids.

In another aspect, a method of quantifying the amount of a plurality of double stranded nucleic acids is provided, including: contacting the plurality of double stranded nucleic acids with a) a first dye, and b) a detectably labeled single stranded sizing ladder, under conditions wherein the first dye is configured to label a double stranded nucleic acid; producing a mixture comprising a plurality of first dye-labeled double stranded nucleic acids and the detectably labeled single stranded sizing ladder; migrating the mixture under mobility dependent separation conditions; separating each of the plurality of first dye-labeled double stranded nucleic acids; receiving fluorescence data related to the plurality of first-dye double stranded nucleic acids, where the fluorescence data may include intensity values over time; identifying a peak within the fluorescence data; determining an area of the peak; and normalizing the area of the peak data to generate a relative concentration value of the double stranded nucleic acid labeled with the first dye.

In yet another aspect, a method of generating a calibration curve is provided including: receiving data related to: a) migrating a plurality of double stranded nucleic acids labeled with a first dye under mobility dependent separation conditions, where the size of each of the double stranded nucleic acids is known, b) migrating a plurality of detectably labeled single stranded reference nucleic acids under the mobility dependent separation conditions, where the size of each of the detectably labeled single stranded reference nucleic acids is known, c) separating each of the plurality of double stranded nucleic acids labeled with the first dye and determining a migration time of each of the plurality of double stranded nucleic acids labeled with the first dye, and d) separating each of the detectably labeled single stranded reference nucleic acids and determining a migration time of each of the detectably labeled single stranded reference nucleic acids; interpolating, based on the determined migration times of the plurality of double stranded nucleic acids labeled with the first dye and determined migration times of the detectably labeled single stranded reference nucleic acids, correlated sizes of single stranded reference nucleic acids; and generating a calibration curve relating double stranded nucleic acids labeled with the first dye and detectably labeled single stranded reference nucleic acids. In some embodiments, the calibration curve may be used to determine a size of an unknown double stranded nucleic acid labeled with the first dye. In various embodiments, the method of generating a calibration curve may further include storing the calibration curve in memory.

In another aspect, a computer-readable storage medium encoded with instructions, executable by a processor is provided, the instructions including instructions for: receiving data related to: a) migrating a plurality of double stranded nucleic acids labeled with a first dye under mobility dependent separation conditions, where the size of each of the double stranded nucleic acids is known, b) migrating a plurality of detectably labeled single stranded reference nucleic acids under the mobility dependent separation conditions, where the size of each of the detectably labeled single stranded reference nucleic acids is known, c) separating each of the plurality of double stranded nucleic acids labeled with the first dye and determining a migration time of each of the plurality of double stranded nucleic acids labeled with the first dye, and d) separating each of the detectably labeled single stranded reference nucleic acids and determining a migration time of each of the detectably labeled single stranded reference nucleic acids; interpolating, based on the determined migration times of the plurality of double stranded nucleic acids labeled with the first dye and determined migration times of the detectably labeled single stranded reference nucleic acids, correlated sizes of single stranded reference nucleic acids; and generating a calibration curve relating double stranded nucleic acids labeled with the first dye and detectably labeled single stranded reference nucleic acids.

In yet another aspect, a system for generating a calibration curve is provided, the system including: a fluorescence detector interface configured to receive data related to: a) migrating a plurality of double stranded nucleic acids labeled with a first dye under mobility dependent separation conditions, where the size of each of the double stranded nucleic acids is known, b) migrating a plurarlity of detectably labeled single stranded reference nucleic acids under the mobility dependent separation conditions, where the size of each of the detectably labeled single stranded reference nuclic acids is known, c) separating each of the plurality of double stranded nucleic acids labeled with the first dye, d) determining a migration time of each of the plurality of double stranded nucleic acids labeled with the first dye, and e) separating each of the detectably labeled single stranded reference nucleic acids and determining a migration time of each of the detectably labeled single stranded reference nucleic acids; a migration time correlator configured to: a) interpolate, based on the determined migration times of the plurality of double stranded nucleic acids labeled with the first dye and determined migration times of the detectably labeled single stranded reference nucleic acids, correlated sizes of single stranded reference nucleic acids, and b) generate a calibration curve relating double stranded nucleic acids labeled with the first dye and detectably labeled single stranded reference nucleic acids; a calibration curve database configured to store the calibration curve, and a display configured to display the calibration curve to a user.

In another aspect, a system for generating a calibration curve is provided, the system including: a processor; and a memory encoded with instructions, executable by the processor, the instructions for receiving data related to: a) migrating a plurality of double stranded nucleic acids labeled with a first dye under mobility dependent separation conditions, where the size of each of the double stranded nucleic acids is known, b) migrating a plurality of detectably labeled single stranded reference nucleic acids under the mobility dependent separation conditions, wherein the size of each of the detectably labeled single stranded reference nucleic acids is known, c) separating each of the plurality of double stranded nucleic acids labeled with the first dye and determining a migration time of each of the plurality of double stranded nucleic acids labeled with the first dye, and d) separating each of the detectably labeled single stranded reference nucleic acids and determining a migration time of each of the detectably labeled single stranded reference nucleic acids; interpolating, based on the determined migration times of the plurality of double stranded nucleic acids labeled with the first dye and determined migration times of the detectably labeled single stranded reference nucleic acids, correlated sizes of single stranded reference nucleic acids; and generating a calibration curve relating double stranded nucleic acids labeled with the first dye and detectably labeled single stranded reference nucleic acid.

In another aspect, a method of determining relative concentration is provided, the method including: receiving fluorescence data related to a double stranded nucleic acid labeled with a first dye, wherein the fluorescence data includes intensity values over time; identifying a peak within the fluorescence data; determining an area of the peak; and normalizing the area of the peak data to generate a relative concentration value of the double stranded nucleic acid labeled with the first dye.

In yet another aspect, a computer-readable storage medium encoded with instructions, executable by a processor provided, the instructions including instructions for: receiving fluorescence data related to a double stranded nucleic acid labeled with a first dye, wherein the fluorescence data includes intensity values over time; identifying a peak within the fluorescence data; determining an area of the peak; and normalizing the area of the peak data to generate a relative concentration value of the double stranded nucleic acid labeled with the first dye.

In a further aspect, a system for determining relative concentration is provided, the system including: a fluorescence detector interface configured to receive fluorescence data related to a double stranded nucleic acid labeled with a first dye, wherein the fluorescence data includes intensity values over time; a relative concentration calculator configured to: a) identify a peak within the fluorescence data, b) determine an area of the peak, and c) normalize the area of the peak data to generate a relative concentration value of the double stranded nucleic acid labeled with the first dye; a relative concentration database configured to store the relative concentration value; and a display for displaying the relative concentration value to the user.

In another aspect, a system for determining relative concentration is provided, the system including: a processor; and a memory encoded with instructions, executable by the processor, the instructions for: a) receiving fluorescence data related to a double stranded nucleic acid labeled with a first dye, wherein the fluorescence data includes intensity values over time; b) identifying a peak within the fluorescence data; c) determining an area of the peak; and d) normalizing the area of the peak data to generate a relative concentration value of the double stranded nucleic acid labeled with the first dye.

In yet another aspect, a system for determining a range of lengths of a plurality of double stranded nucleic acids is provided; including: a reactor vessel configured for a) contacting a first dye with a plurality of double stranded nucleic acids, where the first dye may label each of the plurality of double stranded nucleic acids, and b) permitting addition of a detectably labeled single stranded sizing ladder; a channel configured to migrate a mixture of the detectably labeled single stranded sizing ladder and a plurality of first dye-labeled double stranded nucleic acids; an anode and a cathode operably connected to the channel, configured to provide an electric field to the channel; and a detector configured to detect the first dye and a label of the detectably labeled single stranded sizing ladder. In various embodiments, the detector may detect uv absorbance, visible light absorbance, fluorescence, or chemiluminescence. In various embodiments, the system may further include a temperature controllable environment for the channel. In various embodiments, the system may further include a temperature controllable environment for the reactor vessel. In various embodiments, the system further includes a data processor operably connected to the detector.

In various embodiments of the system, the channel may further include a separation medium. In some embodiments, the separation medium may be a sieving medium. In some embodiments, the channel may further include a denaturing additive. In various embodiments, the channel may be configured within a microfluidic chip. In various embodiments, the channel may be an electrophoretic capillary. The channel may be part of a multichannel array.

In another aspect, a kit for determining a range of lengths of a plurality of double stranded nucleic acids is provided; including: a first dye configured to label a double stranded nucleic acid; and a detectably labeled single stranded sizing ladder. In various embodiments, the first dye may label the double stranded nucleic acid non-covalently. In some embodiments, the first dye may be an intercalator. In various embodiments of the kit, the detectably labeled single stranded sizing ladder may be covalently labeled. In various embodiments, the detectably labeled single stranded sizing ladder may be fluorescently labeled. In various embodiments, the detectably labeled single stranded sizing ladder may be labeled with pyrene, naphthalene, aminopyridine, xanthene, cyanine, coumarin, borapolyazaindacine, benzofuran, or indole dye.

In various embodiments of the kit, the first dye may be a cyanine dye, acridine dye, or phenanthridinium dye. In various embodiments, the first dye is a cyanine dye and may be a monomethine cyanine dye. In various embodiments, the first dye is a cyanine dye and may be a dimeric cyanine dye. In various embodiments of the kit, the first dye has a structure of Formula I:

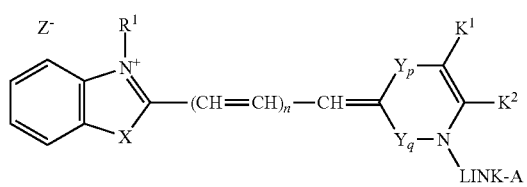

Formula I where X is O, S, Se, or C(CH$_3$); R$^1$ is C$_1$-C$_6$ alkyl; n=0, 1 or 2; Y is —CH$_2$=CH$_2$—, where p and q are equal to 0 or 1, such that p+q=1; K$^1$ and K$^2$ are the same or different, and are independently hydrogen, an alkyl group having 1-6 carbons, or aryl; or K$^1$ and K$^2$ are taken in combination to complete a 6-membered aromatic ring to yield a quinolinium ring system; LINK is an aliphatic chain containing a backbone of 4 to 19 methylene groups (—CH$_2$—), which is optionally interspersed at one or more intervals with a heteroatom, each of which is independently N, O or S, wherein each N heteroatom is additionally substituted by 1-2 H, or 1-2 alkyl groups with 1 to 6 carbons, which alkyl substituents may be the same or different, provided that any heteroatom is separated from another heteroatom by at least 2 methylene groups, wherein one methylene terminus of LINK is attached to a nitrogen atom of the pyridinium or quinolinium heterocycle and another methylene terminus of LINK is attached to A, except that where A is H or CH$_3$, LINK must contain at least one N heteroatom; A is either H, CH$_3$ or has a structure of Formula A:

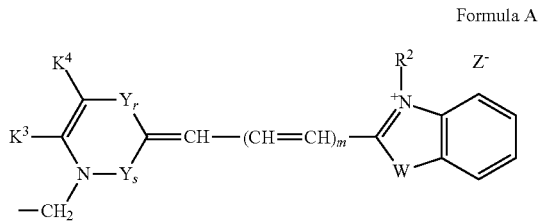

Formula A where W is O, S, Se, or C(CH$_3$); R$^2$ is C$_1$-C$_6$ alkyl; m=0, 1 or 2; Y is —CH$_2$=CH$_2$—, with subscripts r and s equal to 0 or 1, such that r+s=1; K$^3$ and K$^4$ may be the same or different, and are independently hydrogen, an alkyl group having 1-6 carbons, or aryl; or K$^3$ and K$^4$ are taken in combination to complete a 6-membered aromatic ring to yield a quinolinium ring system; when A is not H or CH$_3$, m and n can be the same or different; and W and X can be the same or different.

In some embodiments, the first dye may be a cyanine dye of Formula I where X is 0; R$^1$ is methyl; the methine bridge is monomethine, where n is 0; Y$_p$ has p=0 and Y$_q$ has q=1; K$^1$ and K$^2$ are taken together in combination to complete a 6 membered aromatic ring yielding a quinolinium ring system; LINK has a backbone of 9-12 methylene groups and interspersed at two intervals with a nitrogen atom, where each nitrogen atom is mono- or di-substituted with C$_1$-C$_6$ carbons, and further where the two nitrogen atoms are separated from each other by at least two methylene groups; A has a structure of Formula A:

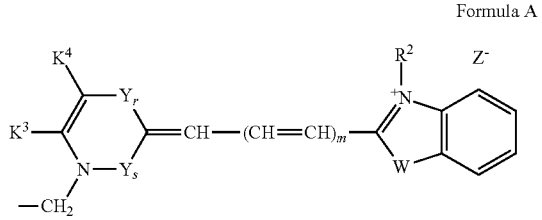

Formula A where W is O; R$^2$ is methyl; the methine bridge is monomethine where m=0; Y$_r$ has r=0 and Y$_s$ has s=1; and K$^3$ and K$^4$ are taken in combination to complete a 6 membered aromatic ring to yield a quinolinium ring system.

In various embodiments of the kit, the first dye may be spectrally resolvable from a second dye labelling the detectably labeled single stranded sizing ladder.

In various embodiments of the kit, the kit may further include a channel incorporated in a microfluidic chip. In various embodiments of the kit, the channel may include a separation medium. In various embodiments, the channel may include a denaturing additive. In various embodiments of the kit, the channel may include a buffer solution.

In another aspect, a composition for determining a range of lengths of a plurality of double stranded nucleic acids is provided, including: a first dye configured to label a double stranded nucleic acid; a plurality of double stranded nucleic acids; and a detectably labeled single stranded sizing ladder. In various embodiments, the plurality of double stranded nucleic acids may be ribonucleic acids having at least a partially double stranded structure. In other embodiments, the plurality of double stranded nucleic acids may be DNA. In various embodiments, the composition may further include a denaturing additive. In various embodiments, the first dye may be configured to not label a single stranded nucleic acid. In various embodiments, the first dye may label the double stranded nucleic acid non-covalently. In various embodiments, the first dye is an intercalating dye. In various embodiments, the detectably labeled single stranded sizing ladder may be covalently labeled. In various embodiments, the detectably labeled single stranded sizing ladder may be fluorescently labeled. In various embodiments, the detectably labeled single stranded sizing ladder may be labeled with pyrene, naphthalene, aminopyridine, xanthene, cyanine, coumarin, borapolyazaindacine, benzofuran, or indole dye. In various embodiments, the first dye may be a cyanine dye, acridine dye, or phenanthridinium dye. In various embodiments, the first dye is a cyanine dye and may be selected from a monomethine cyanine or a dimeric cyanine.

In various embodiments of the composition, the first dye may have a structure of Formula I:

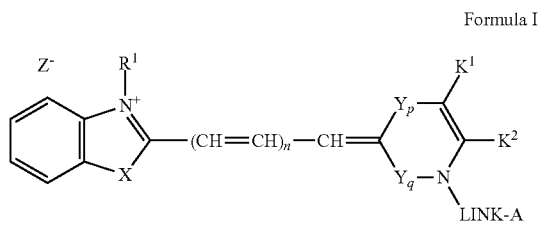

Formula I where X is O, S, Se, or C(CH$_3$); R$^1$ is C$_1$-C$_6$ alkyl; n=0, 1 or 2; Y is —CH$_2$=CH$_2$—, where p and q are equal to 0 or 1, such that p+q=1; K$^1$ and K$^2$ are the same or different, and are independently hydrogen, an alkyl group having 1-6 carbons, or aryl; or K$^1$ and K$^2$ are taken in combination to complete a 6-membered aromatic ring to yield a quinolinium ring system; LINK is an aliphatic chain containing a backbone of 4 to 19 methylene groups (—CH$_2$—), which is optionally interspersed at one or more intervals with a heteroatom, each of which is independently N, O or S, wherein each N heteroatom is additionally substituted by 1-2 H, or 1-2 alkyl groups with 1 to 6 carbons, which alkyl substituents may be the same or different, provided that any heteroatom is separated from another heteroatom by at least 2 methylene groups, wherein one methylene terminus of LINK is attached to a nitrogen atom of the pyridinium or quinolinium heterocycle and another methylene terminus of LINK is attached to A, except that where A is H or CH$_3$, LINK must contain at least one N heteroatom; A is either H, CH$_3$ or has a structure of Formula A:

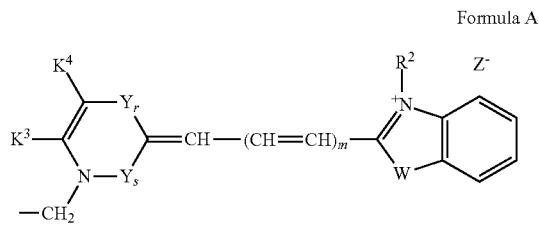

Formula A where W is O, S, Se, or C(CH$_3$); R$^2$ is C$_1$-C$_6$ alkyl; m=0, 1 or 2; Y is —CH$_2$=CH$_2$—, with subscripts r and s equal to 0 or 1, such that r+s=1; K$^3$ and K$^4$ may be the same or different, and are independently hydrogen, an alkyl group having 1-6 carbons, or aryl; or K$^3$ and K$^4$ are taken in combination to complete a 6-membered aromatic ring to yield a quinolinium ring system; when A is not H or CH$_3$, m and n can be the same or different; and W and X can be the same or different.

In some embodiments, the first dye may be a cyanine dye of Formula I where X is O; R$^1$ is methyl; the methine bridge is monomethine, where n is 0; Y$_p$ has p=0 and Y$_q$ has q=1; K$^1$ and K$^2$ are taken together in combination to complete a 6 membered aromatic ring yielding a quinolinium ring system; LINK has a backbone of 9-12 methylene groups and interspersed at two intervals with a nitrogen atom, where each nitrogen atom is mono- or di-substituted with C$_1$-C$_6$ carbons, and further where the two nitrogen atoms are separated from each other by at least two methylene groups; A has a structure of Formula A:

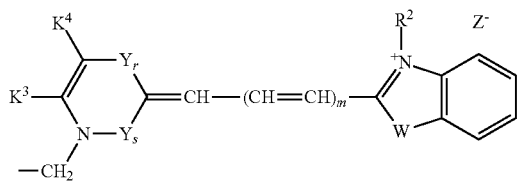

Formula A where W is O; R$^2$ is methyl; the methine bridge is monomethine where m=0; Y$_r$ has r=0 and Y$_s$ has s=1; and K$^3$ and K$^4$ are taken in combination to complete a 6 membered aromatic ring to yield a quinolinium ring system.

In various embodiments, the first dye may be spectrally resolvable from a dye labeling the detectably labeled single stranded sizing ladder.

Various patents, patent applications, and other publications are referred to herein, all of which are incorporated herein in their entireties by reference. In addition, the following standard reference works are incorporated herein by reference: Current Protocols in Molecular Biology, John Wiley & Sons, N.Y., edition as of October 2007; Sambrook, Russell, and Sambrook, Molecular Cloning: A Laboratory Manual, 3rd ed., Cold Spring Harbor Laboratory Press, Cold Spring Harbor, 2001. In the event of a conflict between the instant specification and any document incorporated by reference, the specification shall control, it being understood that the determination of whether a conflict or inconsistency exists is within the discretion of the inventors and can be made at any time.

Additional features and advantages of the present teachings will be evident from the description that follows, and in part will be apparent from the description, or can be learned by practice of the present teachings. It is to be understood that both the foregoing summary and the following detailed description are exemplary and explanatory only and are intended to provide further explanation of the present teachings without limiting the present teachings.

The section headings used herein are for organizational purposes only and are not to be construed as limiting the desired subject matter in any way. All literature cited in the specification, including but not limited to, patents, patent applications, articles, books and treatises are expressly incorporated by reference in their entirety for any purpose. In the event that any of the incorporated literature contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

BRIEF DESCRIPTION OF THE FIGURES

FIG. 4 illustrates peak normalization area to determine a relative concentration of sample according to various embodiments described herein.

DETAILED DESCRIPTION

Figure 1:
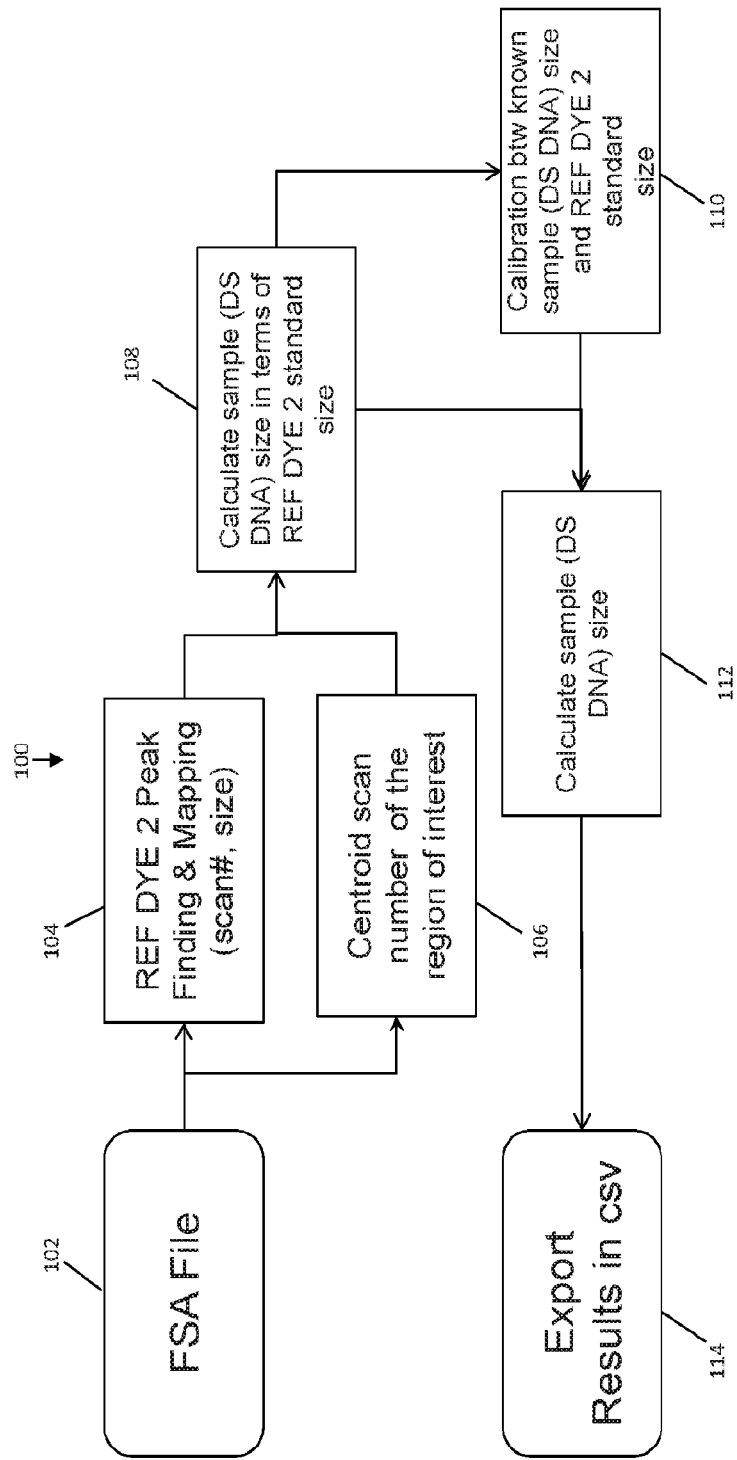
FIG. 1 is a schematic representation of determining a sample size using a calibration curve according to various embodiments described herein.

As used herein, "channel" and its derivatives, refers to a groove, a tube or a capillary or other structure for carrying out electrophoresis that is capable of supporting a volume of separation medium, such as a composition for separating labeled nucleic acids as disclosed herein. The geometry of a channel may vary widely and includes, but is not limited to, grooves, capillaries or tubes with circular, rectangular or square cross-sections, grooves, and the like, and may be fabricated by a wide range of technologies. One feature of a channel for use with certain embodiments of the invention is the surface-to-volume ratio of the surface in contact with the volume of separation medium. High values of this ratio typically permit better heat transfer from the separation medium during electrophoresis.

In certain embodiments, values in the range of about 0.8 to 0.02 $m^{-1}$ may be employed. These correspond to the surface-to-volume ratios of tubular channels with circular cross-sections having inside diameters in the range of about 5 µm to about 200 µm. The term "uncoated channel" means that the channel is uncoated prior to the introduction of compositions of the invention, i.e., not coated prior to use. In certain embodiments, channels for use with the invention are made of silica, fused silica, quartz, silicate based glass, such as borosilicate glass, phosphate glass, alumina-containing glass, and the like, or other silica-like materials. In certain embodiments, channels formed in plastic substrates are used. Plastic substrates may comprise, for example, polyacrylates and polyolefins, such as LUCRYL®(BASF, Germany), TPX™ (Matsui Plastics, Inc., White Plains, N.Y.), TOPAS® (Hoechst Celanese Corp., Summit, N.J.), and ZEONOR® (Zeon Chemicals, Louisville, Ky.) Descriptions of plastic substrates for channels formed within such substrate may be found, among other places, in U.S. Pat. No. 5,750,015. Channels may be part of a microfluidic structure.

As used herein, "contacting" and its derivatives, when used in reference to two or more components, refers generally to any process whereby the approach, proximity, mixture or commingling of the referenced components is promoted or achieved, and may include mixing of solutions containing any one or more of the referenced components with each other. The referenced components may be contacted in any particular order or combination and the particular order of recitation of components is not limiting.

As used herein, "sample" and its derivatives, is used in its broadest sense and includes any specimen, culture and the like that is suspected of including a double stranded nucleic acid. A sample comprising at least one double stranded nucleic acid may be obtained from a wide variety of sources including, but not limited to, therapeutic formulations and biological samples, which may include but is not limited to cell cultures, patient samples (including tissue, sputum, blood or urine) or manufacturing processes for therapeutics. The term also includes any isolated nucleic acid sample such a genomic DNA, fresh-frozen or formalin-fixed paraffin-embedded nucleic acid specimen.

The term "mobility-dependent separation" as used herein refers to the separation of labeled nucleic acids due to the charge and size associated with the labeled nucleic acid.

The term "fluorescent dye" as used herein refers to moieties that absorb light energy at a defined excitation wavelength and emit light energy at a different wavelength. Preferably, if a plurality of fluorescent dyes is selected for use in one experiment, the dyes are spectrally resolvable. As used herein, "spectrally resolvable" means that the dyes can be distinguished on the basis of their spectral characteristics, particularly fluorescence emission wavelength, under conditions of operation. For example, the identity of the one or more terminal nucleotides can be correlated to a distinct wavelength of maximum light emission intensity, or perhaps a ratio of intensities at different wavelengths.

As used herein, the term "nucleotide" and its variants refers to any naturally occurring nucleotide or analog thereof, without limitation. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281. In some embodiments, the nucleotide comprises a label and referred to herein as a "labeled nucleotide"; the label of the labeled nucleotide is referred to herein as a "nucleotide label". In some embodiments, the label can be in the form of a fluorescent dye attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group can include sulfur substitutions for the various oxygens, e.g., alpha-thio-nucleotide 5'-triphosphates. For a review of nucleic acid chemistry, see: Shabarova, Z. and Bogdanov, A. Advanced Organic Chemistry of Nucleic Acids, VCH, New York, 1994.

As used herein, the terms "polynucleotide", "nucleic acid", or "oligonucleotide" refers to a linear polymer of nucleosides (including deoxyribonucleosides, ribonucleosides, or analogs thereof) joined by inter-nucleosidic linkages. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes deoxythymidine, unless otherwise noted. The letters A, C, G, and T can be used to refer to the bases themselves, to nucleosides, or to nucleotides comprising the bases, as is standard in the art. In naturally occurring polynucleotides, the inter-nucleoside linkage is typically a phosphodiester bond, and the subunits are referred to as "nucleotides." Oligonucleotide primers comprising other inter-nucleoside linkages, such as phosphorothioate linkages, are used in certain embodiments of the teachings. The polynucleotide may also include locked nucleic acid (LNA). It will be appreciated that one or more of the subunits that make up such an oligonucleotide primer with a non-phosphodiester linkage may not comprise a phosphate group. Such analogs of nucleotides are considered to fall within the scope of the term "nucleotide" as used herein, and nucleic acids comprising one or more inter-nucleoside linkages that are not phosphodiester linkages are still referred to as "polynucleotides", "oligonucleotides", etc.

As used herein, the term "phosphorothioate linkage" refers to an inter-nucleotide linkage comprising a sulfur atom in place of a non-bridging oxygen atom within the phosphate linkages of a sugar phosphate backbone. The term phosphorothioate linkage refers to both phosphorothioate inter-nucleotide linkages and phosphorodithioate inter-nucleotide linkages. A "phosphorothioate linkage at a terminal 3' end" refers to a phosphorothioate linkage at the 3' terminus, that is, the last phosphate linkage of the sugar phosphate backbone at the 3' terminus.

As used herein, the term "phosphodiester linkage" may refer to the linkage—$PO_4$— which is used to link nucleotide monomers, such as the inter-nucleotide linkages found in naturally-occurring DNA. Additionally, "phosphodiester linkage" may refer to portions of the NCMs or NCM linkers of the chemically-enhanced primers of the present disclosure.

The term "nucleobase" or "base" as used herein refers to a nitrogen-containing heterocyclic moiety capable of forming Watson-Crick type hydrogen bonds with a complementary nucleobase or nucleobase analog, e.g. a purine, a 7-deazapurine, or a pyrimidine. Typical nucleobases are the naturally occurring nucleobases adenine, guanine, cytosine, 5mC, uracil, thymine, and analogs of naturally occurring nucleobases, e.g. 7-deazaadenine, 7-deaza-8-azaadenine, 7-deazaguanine, 7-deaza-8-azaguanine, N6-$\Delta$2 isopentenyl-adenine(6iA), N6-$\Delta$2-isopentenyl-2-methylthioadenine (2ms6iA), N2-dimethyl-guanine(dmG), 7-methylguanine (7mG), inosine, nebularine, nitropyrrole, nitroindole, 2-amino-purine, 2,6-diamino-purine, hypoxanthine, pseudouridine, pseudocytidine, pseudoisocytidine, 5-propynyl-cytidine, isocytidine, isoguanine, 2-thiopyrimidine, 6-thioguanine, 4-thiothymine, 4-thiouracil, $O^6$-methylguanine, $N^6$-methyl-adenine, $O^4$-methylthymine, 5,6-dihydrothymine, 5,6-dihydrouracil, 4-methylindole, pyrazolo[3,4-D]pyrimidines (see, e.g., U.S. Pat. Nos. 6,143,877 and 6,127,121 and PCT Published Application WO 01/38584) and ethenoadenine. Nonlimiting examples of nucleotide bases can be found, e.g., in Fasman, Practical Handbook of Biochemistry and Molecular Biology, pp. 385-394, CRC Press, Boca Raton, Fla. (1989).

As used herein, the term "end" and its variants, when used in reference to a nucleic acid molecule, can include the terminal 3 nucleotides, the terminal 2 and even more typically the terminal nucleotide of the nucleic acid molecule. A linear nucleic acid molecule comprised of linked series of contiguous nucleotides typically includes at least two ends. In some embodiments, one end of the nucleic acid molecule can include a 3' hydroxyl group or its equivalent, and can be referred to as the "3' end" and its derivatives. Optionally, the 3' end includes a 3' hydroxyl group that is not linked to a 5' phosphate group of a mononucleotide pentose ring.

As used herein, "5' end", and its derivatives, generally refers to an end of a nucleic acid molecule, which in a native nucleic acid may include a free 5' phosphate group or its equivalent. In some embodiments, the 5' end includes a 5' phosphate group that is not linked to a 3' hydroxyl of a neighboring mononucleotide pentose ring, but is linked, optionally via a 5' linker, to a detectable moiety including a dye, which may include a visible, fluorescent dye (including polymeric or energy transfer dyes), or chemiluminescent dye.

Selected compounds having a formal electronic charge may be shown without an appropriate biologically compatible counterion. Such a counterion serves to balance the positive or negative charge present on the compound. As used herein, a substance that is biologically compatible is not toxic as used, and does not have a substantially deleterious effect on biomolecules. Examples of negatively charged counterions include, among others, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Preferred counterions may include chloride, iodide, perchlorate and various sulfonates. Examples of positively charged counterions include, among others, alkali metal, or alkaline earth metal ions, ammonium, or alkylammonium ions.

As used herein, "to size", "sizing" a plurality of double stranded nucleic acids (including nucleic acid libraries produced for next generation sequencing) refers to determining the number of base pairs in a nucleic acid strand. As the molecular weight of each of the typically occurring natural nucleotides are roughly equivalent, a measure of size can also infer a molecular weight.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

While Next Generation Sequencing technologies offer higher genome throughput per run, the sequencing workflow for any of these platforms (including but not limited to: Ion Torrent™ (ThermoFisher Scientific), MiSeq® (Illumina, Inc.), and 454 Flx and GS Junior+systems (Roche), for example) requires good library construction and quality control. The nucleic acid library produced from the original sample needs to have fragment sizes within a predetermined range to be effectively sequenced in any of these technologies. Additionally, the amount of amplicons present in the nucleic acid library, resulting from a variety of manipulations including one or more of fragmentation, amplification, ligation and labeling, is necessary to be quantified prior to introduction of an aliquot of the library to the sequencing reaction conditions. The currently available methods to perform this analysis often requires acquisition of yet another instrument to characterize the library pool, and/or may further require separate quantification by a separate qPCR method.

What is provided here are electrophoretic methods to size a nucleic acid library or any plurality of double stranded nucleic acids that require characterization before further analysis or processing. In some embodiments, the electrophoretic methods also include methods of quantifying the amount of nucleic acid present in the plurality of double stranded nucleic acids under examination. Using electrophoretic methods and instrumentation already available in laboratories that run many different types of experiments, characterization can be made using separation media and conditions which do not require tedious reagent switchovers and/or flushing routines. Therefore, QC and/or quantitation may be provided with standard reagents and instrumentation typically available to many laboratories.

It has been surprisingly discovered that sizing double stranded nucleic acids can be performed in the presence of a single stranded size standard, i.e. sizing ladder, in electrophoretic separations, to obtain meaningful information about the sizes of the plurality of double stranded nucleic acids. Generally one of skill in the art sizes double stranded nucleic acids with a double stranded nucleic acid sizing ladder and singled stranded nucleic acid with a single stranded nucleic acid sizing ladder. Single stranded nucleic acids and double stranded nucleic acids migrate differently if one were to use nucleic acids of different type to size the other. It has been surprisingly discovered that the differences can be correlated and modeled to be used in sizing applications. It has further been surprisingly found that these differences are dependent to the separation conditions, such as, but not limited to, temperature, denaturant, sieving polymer, and the like.

Methods.

A method for determining a range of lengths of a plurality of double stranded nucleic acids is described here that includes contacting the plurality of double stranded nucleic acids with a first dye, and a detectably labeled single stranded sizing ladder, under conditions where the first dye is configured to label a double stranded nucleic acid; producing a mixture including a plurality of first dye-labeled double stranded nucleic acids and the detectably labeled single stranded sizing ladder; migrating the mixture under mobility dependent separation conditions; separating each of the plurality of first dye-labeled double stranded nucleic acids and determining a migration time of each of the plurality of first dye-labeled double stranded nucleic acids. In some embodiments, the method further includes the step of determining a migration time of each of the plurality of fragments of the single stranded sizing ladder. In some embodiments, the method further includes a step of quantifying the amount of the plurality of double stranded nucleic acids.

A plurality of double stranded nucleic acids, including but not limited to a library prepared from DNA or RNA, may be characterized for the range of nucleic acid lengths present in the plurality, prior to any massively parallel process step, which may include an amplification, ligation, hybridization or sequencing step. The double stranded nucleic acids may be contacted with a first dye which labels the double stranded nucleic acids to produce a plurality of first dye-labeled double stranded nucleic acids. The first dye may label the plurality of double stranded nucleic acids noncovalently. In some embodiments, the first dye may be configured to label at least a detectable portion of the plurality of double-stranded nucleic acids. Alternatively, the first dye may be configured to label a substantial portion of the plurality of double stranded nucleic acids. The first dye may be configured to label double stranded nucleic acids, but not be configured to label single stranded nucleic acid. The first dye may label double stranded nucleic acid by interacting with nucleic acid only when nucleic acid is present in double stranded form, i.e. when a first single stranded nucleic acid strand is hybridized to its complementary nucleic acid strand. In some embodiments, the plurality of double stranded nucleic acid may be RNA where the RNA has a partially double stranded structure due to self hybridization of a first strand and does not require hybridization to a second, separate complementary strand. In these embodiments, the first dye may label the portion of RNA that has double stranded structure. In yet other embodiments, the RNA, such as a viral RNA, may be a double stranded RNA with two complementary strands. In these embodiments, the first dye may label the entirety of the double stranded RNA having two complementary strands.

In some embodiments, the first dye may be configured to substantially not label a single stranded nucleic acid. In various embodiments, the first dye may label the plurality of double stranded nucleic acids noncovalently. In some embodiments, the first dye may label the plurality of double stranded nucleic acids as an intercalating dye. When the first dye is not configured to label single stranded nucleic acid, it may not label the single stranded sizing ladder. In some embodiments, the first dye does not substantially label the single stranded sizing ladder while it does substantially label the plurality of double stranded nucleic acids. The first dye may be added to the plurality of double stranded nucleic acids before, after, or simultaneously with the detectably labeled single stranded sizing ladder to form the mixture of the plurality of first dye-labeled double stranded nucleic acids and the detectably labeled single stranded sizing ladder. The first dye may label the plurality of double stranded nucleic acids, or at least a detectably portion of it, by holding the mixture at a pre-selected temperature for a period of time. In some embodiments, the preselected temperature may be at room temperature or at an elevated temperature.

The second dye may label the fragments of the detectably labeled single stranded sizing ladder covalently. The second dye may be spectrally resolvable from the first dye. In some embodiments, the second dye, which is covalently attached to the fragments of the single stranded sizing ladder, may be observable at the same wavelength as the first dye.

The mixture of the plurality of first-dye labeled double stranded nucleic acids and the detectably labeled single stranded sizing ladder may be subjected to mobility dependent separation conditions. The mixture may be injected into a channel that can support a mobility dependent separation and may be migrated under the mobility dependent separation conditions, which may include the influence of an electric field. The detectably labeled single stranded sizing ladder may be migrated in the same channel as the double stranded nucleic acids. In some embodiments, the second dye of the detectably labeled single stranded sizing ladder is spectrally resolvable from the first dye of the dye-labeled plurality of double stranded nucleic acids when being co-migrated in the same channel. Migration in the same channel during the same experimental run may provide the most robust comparison of known migratory speed for the sizing ladder to the unknown individual components of the plurality of double stranded nucleic acids.

Mobility dependent separations include electrophoretic separations, which may depend upon mass-to-charge ratio, and optionally, apparent size of the analyte. The mobility dependent separation conditions may include a separation medium. In some embodiments, the separation medium includes a sieving medium to assist in the separation by size. In some embodiments, nucleic acid mobility dependent separation conditions may include one or more denaturants. Denaturants may be used in a separation buffer and/or separation medium to disrupt any secondary or tertiary structure in a nucleic acid under investigation, which may affect its mobility. Denaturants useful for nucleic acid separations include but are not limited to one or more of urea, formamide, dimethylsulfoxide (DMSO), and glyoxal. For double stranded nucleic acid, denaturant effects of one or more denaturant additives may be modified by other reaction conditions such as run temperature selection, joule heating, or run module parameters such as injection voltage, run voltage, and/or run temperature/voltage-ramping.

In some embodiments, the mobility dependent separation conditions include no denaturing additive. These conditions may include the use of increased or decreased temperature, relative to the $T_m$ of a double stranded nucleic acid pair of the plurality of dye-labeled double stranded nucleic acids or the temperature at which the single stranded sizing ladder may assume some secondary structure.

Figure 6A:
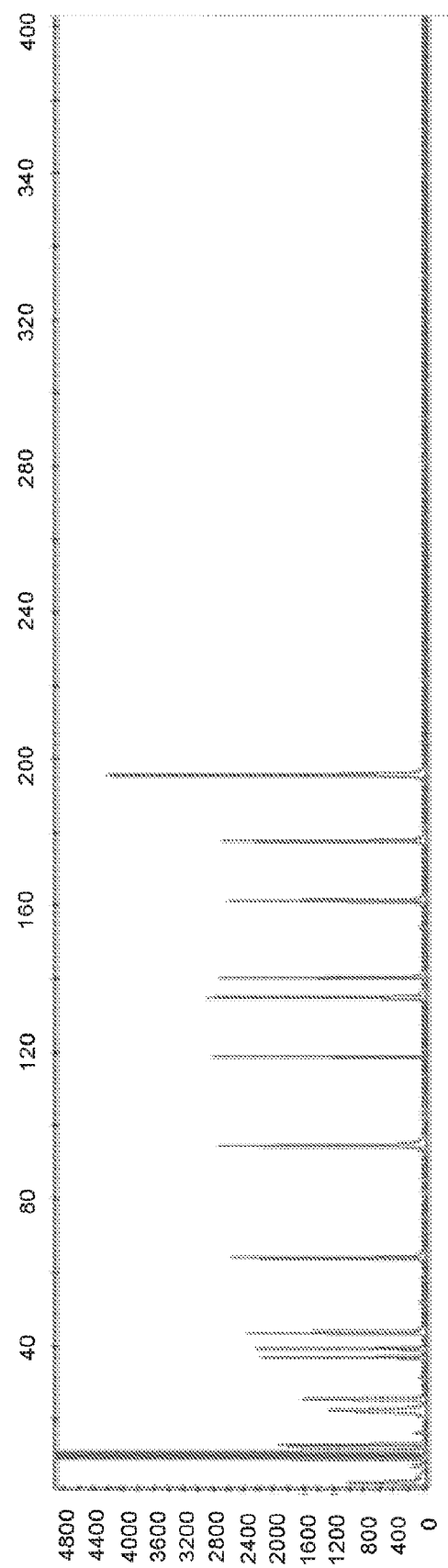
FIG. 6 is a graphical representation of electropherograms of the separation of the same model plurality of double stranded nucleic acids as in FIG. 5, all performed using the same separation medium as that of FIG. 3, and run at 40° C. Each of the top, middle and bottom electropherogram lanes shown is a different capillary run.
Figure 6B:
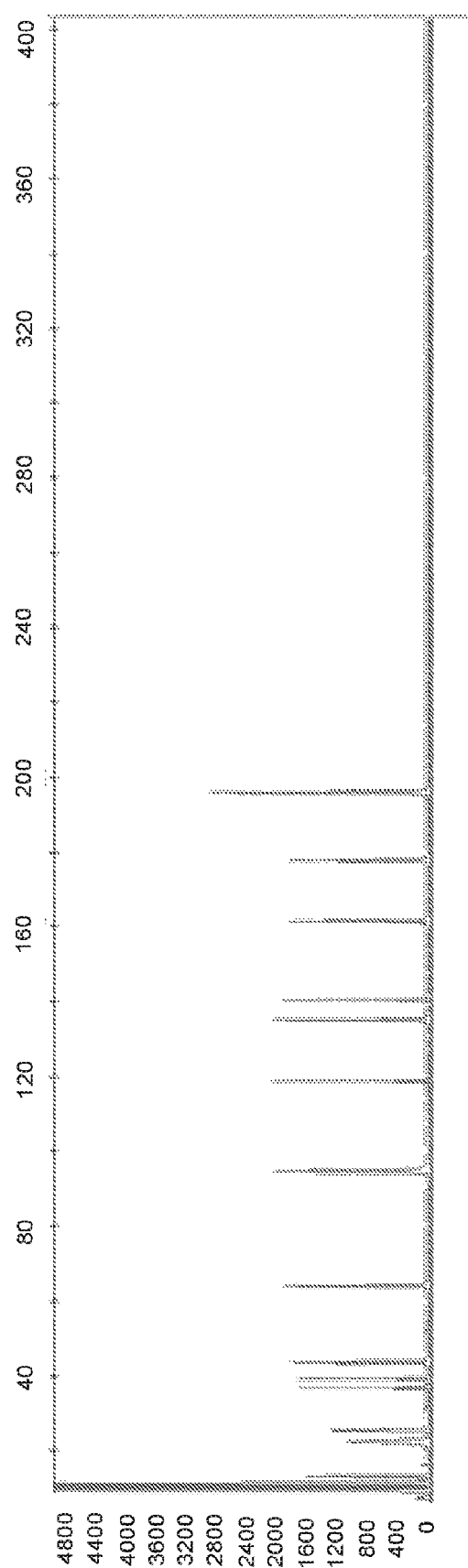
Figure 6C:
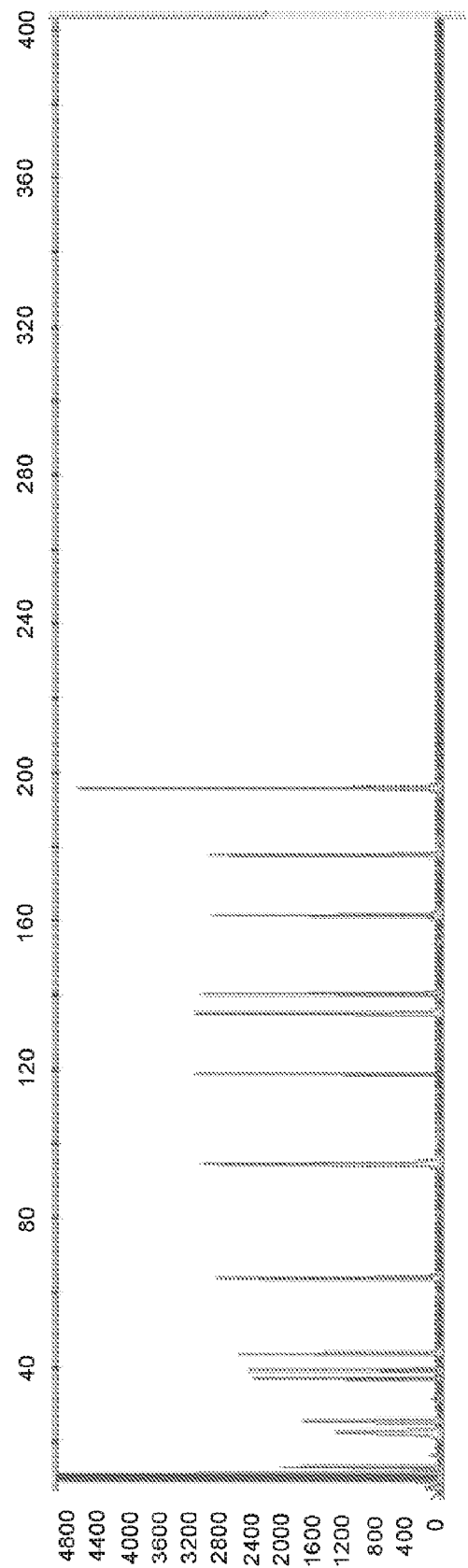
Figure 7:
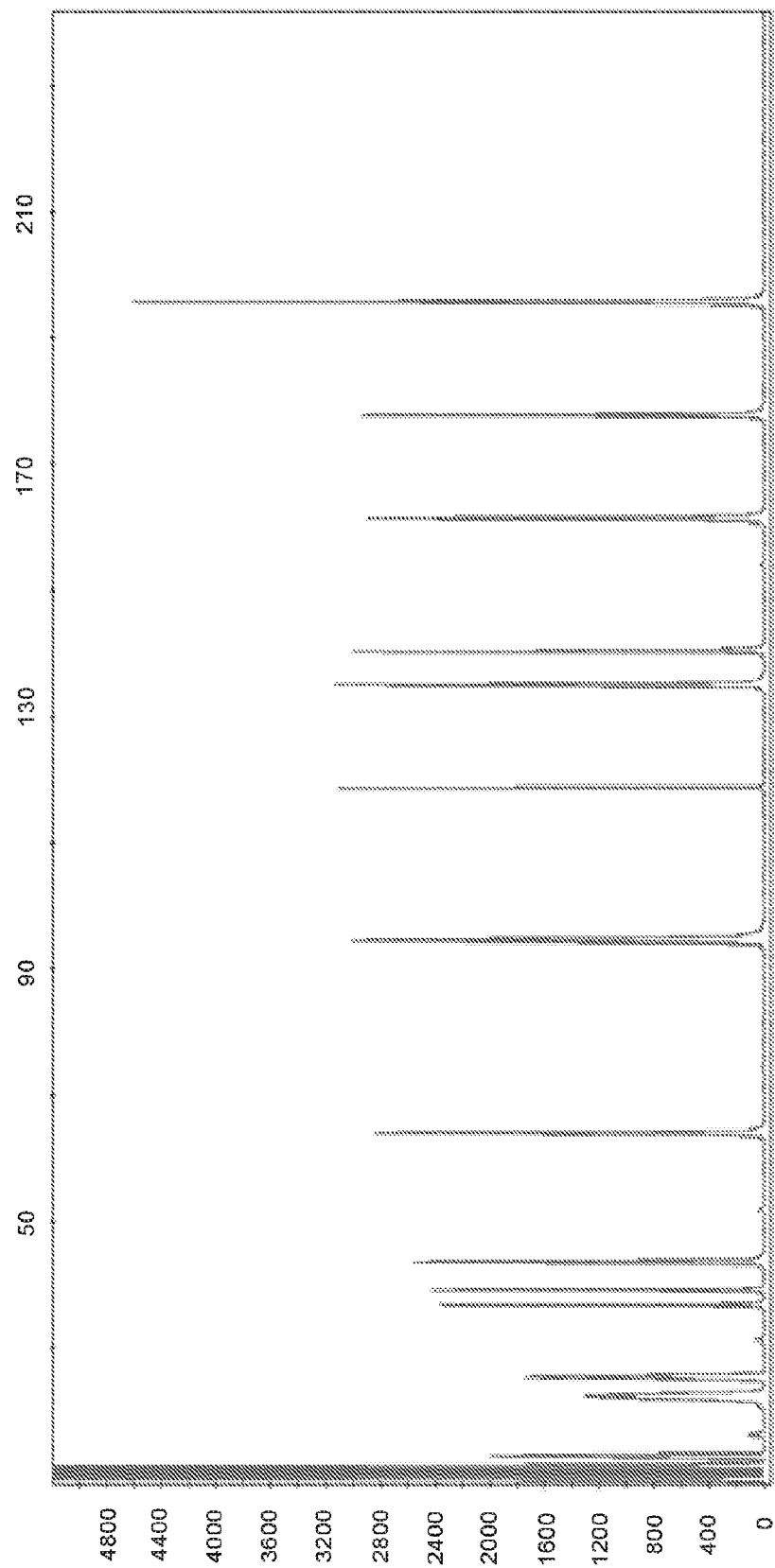
FIG. 7 is a graphical representation of four electropherograms of the separation of the same model plurality of double stranded nucleic acids as in FIG. 5, which are overlaid to shown the reproducibility of migration under these conditions.

In various embodiments, the mobility dependent separation conditions are selected such that the plurality of first-dye labeled double stranded nucleic acids maintains the first-dye labeling. In embodiments when the mobility dependent separation conditions are at least partially denaturing or alternatively, completely denaturing, some portion of the plurality of first dye-labeled double stranded nucleic acids may start to lose hybridization, with resultant loss of at least some of the first dye label. This may be more prevalent with larger fragments which are exposed to the at least partially denaturing conditions for a longer time period. This may be compensated by choosing a lower running temperature than typical denaturing electrophoretic conditions where running temperatures of greater than about 60° C. may be utilized. Additionally, the migration of double stranded nucleic acids may vary considerably under at least partially or wholly denaturing conditions and modification of running temperature may provide more consistent migration times. In FIG. 5 a double stranded sizing ladder which is covalently labeled is run under denaturing conditions as a model for a dye-labeled double stranded nucleic acid library. The migration times are examined at various temperatures. It was determined that 40° C. provided the best separation of this ladder having fragments in the range of 50 to 500 bp. FIG. 6 shows that for multiple separate capillaries separating the same double stranded sizing ladder under the same denaturing conditions as shown in FIG. 5 at 40° C., that consistent migration results were obtained across several capillaries (3 different capillary results are shown). In FIG. 7, the electropherograms from four different capillaries, from the separation of the same dye labeled double stranded model for the dye labeled nucleic acid library as in FIGS. 5 and 6, under the same denaturing conditions, and run at 40° C., are shown, overlaid to demonstrate the reproducibility of the double stranded nucleic acid migration times. In various embodiments, the mobility dependent separation conditions may include a running temperature configured to maintain at least a detectable amount of first dye-labeled double stranded nucleic acids. In some embodiments, the mobility dependent separations conditions may substantially maintain the first dye-label labeling of at least a first portion of the plurality of first dye-labeled double stranded nucleic acids. In some embodiments, the running temperature may be selected to be lower than the temperature at which the first dye label and/or the double strands dissociate from the first dye-labeled double stranded nucleic acids. In some embodiments, the running temperature is lower than the temperature at which the first dye label and/or the double strands dissociate significantly from the first dye-labeled double stranded nucleic acids, whereupon at least a detectable amount of the first dye-labeled double stranded nucleic acids can be detected. In some embodiments, the mobility dependent separation conditions are configured to maintain at least a detectable amount of the first dye label labeling each of the plurality of double stranded nucleic acids. While the first dye may dissociate from some portion of the dye-labeled double stranded nucleic acids, for example, due to the presence of a denaturing additive or run temperature selection, a detectable amount of the first-dye labeled double stranded nucleic acids may remain associated under the mobility dependent separation conditions. In some embodiments, a portion of each of the first dye labeled double stranded nucleic acids may be maintained under the mobility dependent separation conditions in a manner that may be related to the migration time of each first-dye labeled double stranded nucleic acid. In some embodiments, the mobility dependent separation conditions may be configured to substantially maintain the first dye label labeling each of the plurality of double stranded nucleic acids.

When the mixture of the plurality of first-dye labeled double stranded nucleic acids and the detectably labeled single stranded sizing ladder is migrated under mobility dependent separation conditions, each of the plurality of first dye-labeled double stranded nucleic acids may be separated. Migration may separate each of the plurality of first dye-labeled double stranded nucleic acids into bands or peaks having the same weight, within the limits of resolution of the system. In some embodiments, the limit may be about the weight of one nucleotide unit, for example, about 100 Daltons (Da). When the limit of resolution is about one nucleotide unit, each band or peak detected will differ from the preceding or following band or peak by about one nucleotide difference. In other embodiments, the limit of resolution may be the weight of about two nucleotides (200 Da) to about 5 nucleotides (500 Da). When the limit of resolution is about two nucleotides to about 5 nucleotides, each band or peak detected with differ from the preceding or following band or peak by about two to about five nucleotides. Each band or peak having the same weight, within the limits of resolution, may include one distinct nucleic acid or it may include a whole set of distinct nucleic acids of differing sequence but having the same weight/length and therefore, the same mobility under the mobility dependent separation conditions. In some embodiments, the plurality includes a sufficiently large number of double stranded nucleic acids that separation of individual bands may not be visible. In this embodiment, the plurality of first-dye labeled double stranded nucleic acids may be detected as a broad band spanning the range of sizes of nucleic acids in the plurality of double stranded nucleic acids.

The detectably labeled single stranded sizing ladder migrates under the mobility dependent separation conditions to provide each fragment of the sizing ladder as a single peak or band. The migration times of the fragments of the single stranded sizing ladder may be predictable based upon the known fragment size or may be established by running a standards migration separately. In either case, each known fragment of the single stranded sizing ladder may be assigned to a peak in the electropherogram.

Once the mixture of the plurality of first dye-labeled double stranded nucleic acids and the detectably labeled single stranded sizing ladder is separated, a migration time of each of the plurality of first dye-labeled double stranded nucleic acids may be determined. In some embodiments, the migration time is distinct for each of the plurality of first dye-labeled double stranded nucleic acids. In others, a migration time for the plurality may be detected as a broadened band containing a large number of dye-labeled double stranded nucleic acids. A migration time may be determined for each of the fragments of the detectably labeled single stranded sizing ladder. In some embodiments, only a subset of the fragments of the detectably labeled single stranded sizing ladder may be determined. In some embodiments, fragments falling outside of the range of the peaks or bands detected for the plurality of first dye-labeled double stranded nucleic acids may have migration times determined.

The method may further include converting the migration time of each of the plurality of first dye-labeled double stranded nucleic acids to a length. A schematic of one approach to this process is shown in FIG. 1. In some embodiments, the step of converting the migration time includes a step of comparing a migration time of the first dye-labeled double stranded nucleic acid to a migration time of at least one fragment of the detectably labeled single stranded sizing ladder (See FIG. 2). In some embodiments, the step of comparing the migration time of the first dye-labeled double stranded nucleic acid to the migration time of the at least one fragment of the detectably labeled single stranded sizing ladder further includes comparing the first dye-labeled double stranded nucleic acid migration time to a plurality of fragment migration times of the detectably labeled single stranded sizing ladder.

The step of converting the migration time of each of the plurality of first dye-labeled double stranded nucleic acids to a length may further include assigning a length of each first dye-labeled double stranded nucleic acid based on a correlation factor assigned to each fragment of the detectably labeled single stranded sizing ladder.

The method may further include the step of obtaining quantification of the plurality of double stranded nucleic acids by correlating one or more areas under the curve of at least a first plurality of detected peaks of the plurality of first dye-labeled double stranded nucleic acids with at least one or more areas under the curve of a second plurality of detected peaks of the fragments of the detectably labeled sizing ladder. In some embodiments, the at least first plurality of detected peaks of the plurality of first dye-labeled double stranded nucleic acids may include all of the detected peaks of the plurality of first dye-labeled double stranded nucleic acids. The method of quantitation may further include summing all of the correlated areas under the curve of the plurality of the first dye-labeled double stranded nucleic acids, thereby providing quantification for the plurality of double stranded nucleic acids Methods to Determine Size, by Correlating Migration Time.

FIG. 1 is a schematic representation of a method of determining a sample size using a calibration curve according to various embodiments described herein. The method of determining a sample size may be implemented on an exemplary computing system with a processor, such as the computing system shown in FIG. 8. The method may also be implemented in a local computing system or in a server computing system within a network configuration, such as the configuration shown in FIG. 9.

With reference to FIG. 1, step 102 includes using electropherogram data for an unknown sample and electropherogram data of reference nucleic acids. In one embodiment, the reference nucleic acids are detectably labeled single stranded reference nucleic acids of known sizes. The electropherogram data may be included in an FSA file, for example.

In step 104, the reference nucleic acid electropherogram data is analyzed and the intensity peaks for the known sizes of the reference nucleic acid are determined with the corresponding migration times.

In step 106, the electropherogram data of the unknown sample is analyzed to determine a region of interest of peak activity within the data.

In step 108, using the known sizes and migration times of the reference nucleic acids, the unknown sample size is determined in terms of the reference nucleic acid size.

In step 110, a calibration curve is generated by correlating the reference nucleic acid sizes and corresponding migration times with double stranded nucleic acid of known size and the corresponding migration times. The migration time of a double stranded nucleic acid may not have a 1 to 1 direct comparison to a migration time of a reference nucleic acid. In that case, the size of a reference nucleic acid corresponding to the migration time is interpolated. An exemplary calibration curve is illustrated in FIG. 2.

In step 112, using the calibration curve generated in step 110 and the previously calculated unknown sample size in terms of the reference nucleic acid size generated in step 108, the unknown sample size is calculated.

In step 114, the unknown sample size calculation is optionally exported in a CSV file, for example. The calculated unknown sample size may also be displayed to the user on a graphical user interface (GUI).

Figure 2:
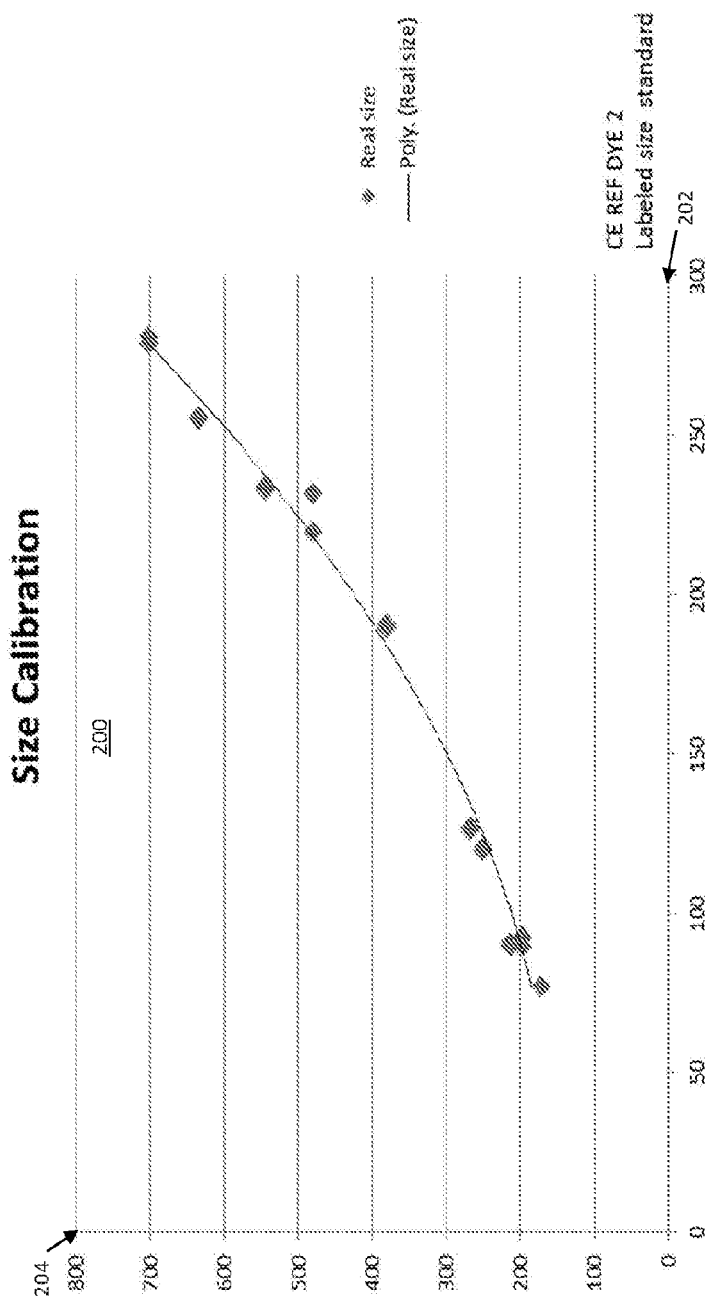
FIG. 2 is a graphical representation of a calibration curve generated according to various embodiments described herein.

As mentioned with reference to the description of FIG. 1, FIG. 2 is a graphical representation 200 of a calibration curve generated according to various embodiments described herein. The calibration curve is generated, according to various embodiments, by correlating migration times of double stranded nucleic acids of known sizes with the migration times of reference single stranded nucleic acids of known sizes. In graphical representation 200, the x-axis 202 shows the sizes of the reference single stranded nucleic acid and the y-axis 204 shows the sizes of the known double stranded nucleic acids. If there is not a direct 1 to 1 match of migration times, the size of the reference single stranded nucleic acid is interpolated. Data plotted in graphical representation of the calibration curve is shown in Table 1.

TABLE 1

| Cap Index | Reference Single Stranded Nucleic Acid Size | Known Double stranded Nucleic Acid Size |
|---|---|---|
| 1 | 255 | 634 |
| 2 | 220 | 481 |
| 3 | 256 | 634 |
| 4 | 234 | 545 |
| 5 | 127 | 268 |
| 6 | 233 | 545 |
| 7 | 281 | 701 |
| 8 | 120 | 251 |
| 9 | 279 | 701 |
| 10 | 191 | 381 |
| 12 | 190 | 381 |
| 13 | 91 | 213 |
| 14 | 232 | 481 |
| 15 | 90 | 213 |
| 16 | 93 | 197 |
| 17 | 126 | 268 |
| 18 | 90 | 197 |
| 19 | 92 | 198 |
| 20 | 121 | 251 |
| 21 | 90 | 198 |
| 22 | 77 | 172 |
| 24 | 77 | 172 |

In this example, the calibration curve is generated using the data shown in Table 1. A line is fitted through the data. The equation for curve fitting for FIG. 2 is $y=0.0078x^2-0.2044x+155.1$, $R^2=0.9925$.

The calibration curve is used to determine the unknown sample size. The unknown sample size in terms of the reference nucleic acid sample size is compared against a calibration curve to determine the double stranded nucleic acid size.

According to various embodiments described herein, calibration curve generation methods and systems are further described below with reference to FIGS. 10 and 11.

Methods to Quantitate Nucleic Acids in the Plurality of Double Stranded Nucleic Acids.

Figure 3:
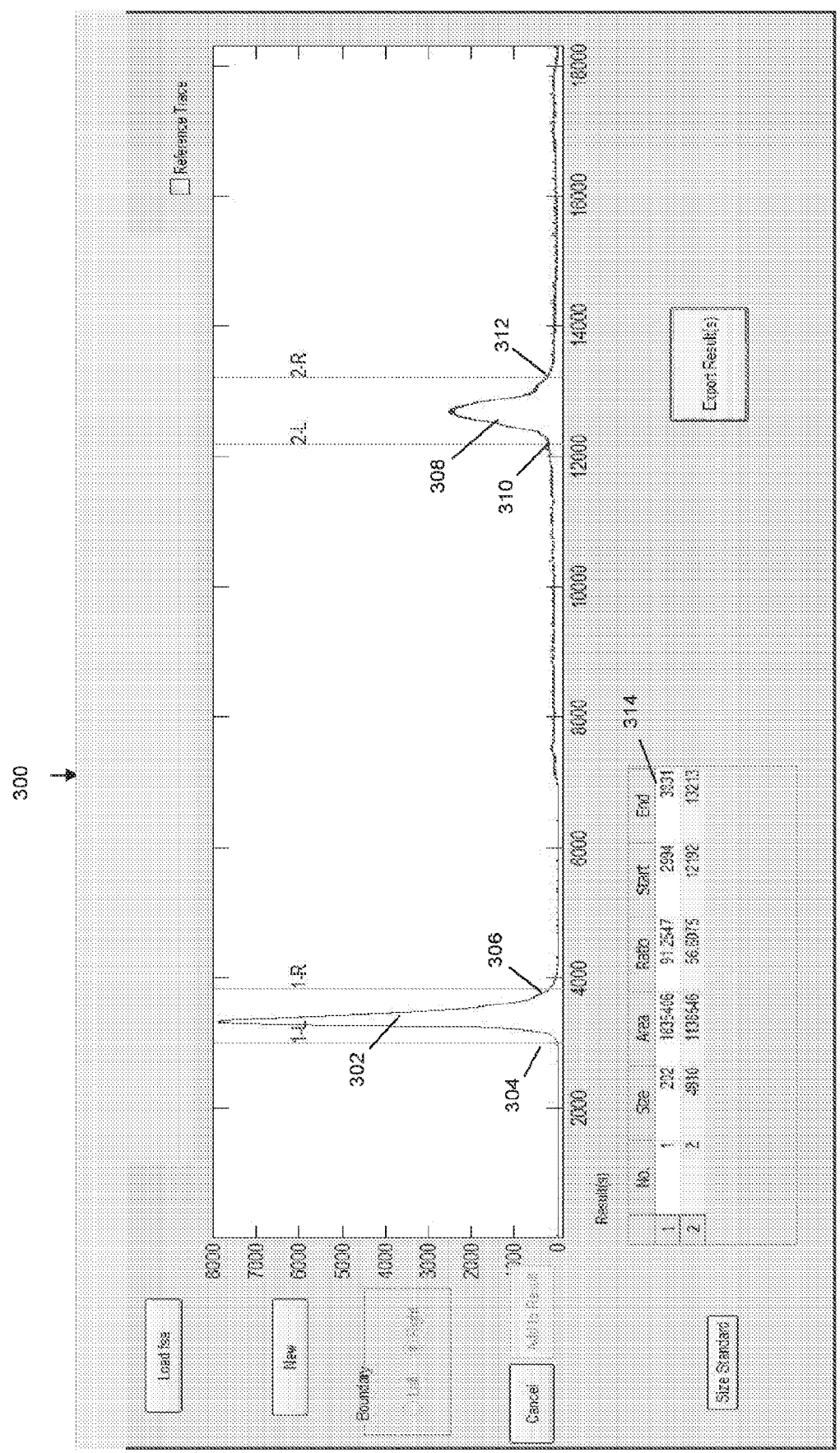
FIG. 3 is a graphical representation of peak detection and normalization according to various embodiments described hererin.
Figure 5A:
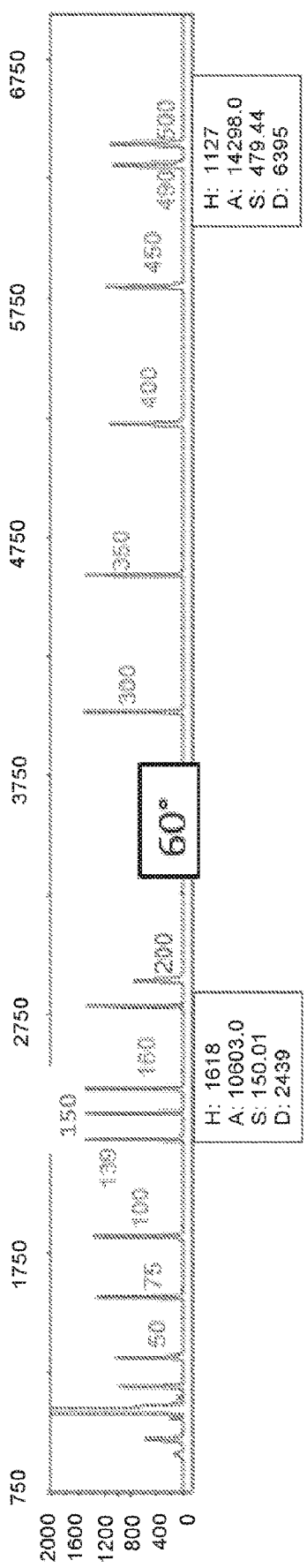
FIG. 5 is a graphical representation of electropherograms of separations of a covalently labeled double stranded sizing ladder which is a model for a dye labeled double stranded nucleic acid library. Separation is performed under totally denaturing conditions (6-8M urea) using a sieving medium (POP-7®, ThermoFisher Scientific). Four electropherogram lanes are shown and from the top lane to the fourth lane at the bottom of the figure, the running temperature is reduced by 10° C., from 60° C., 50° C., 40° C. to 30° C.
Figure 5B:
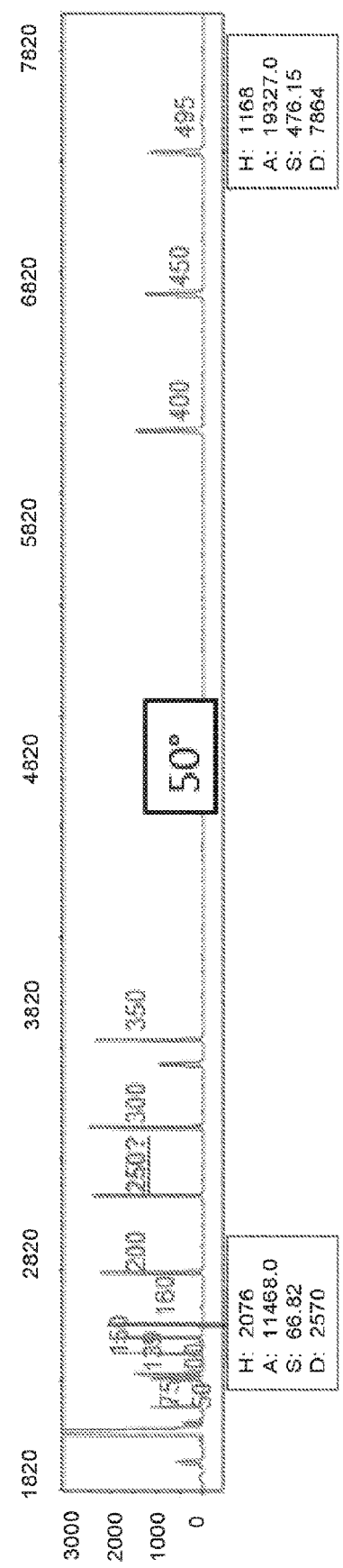
Figure 5C:
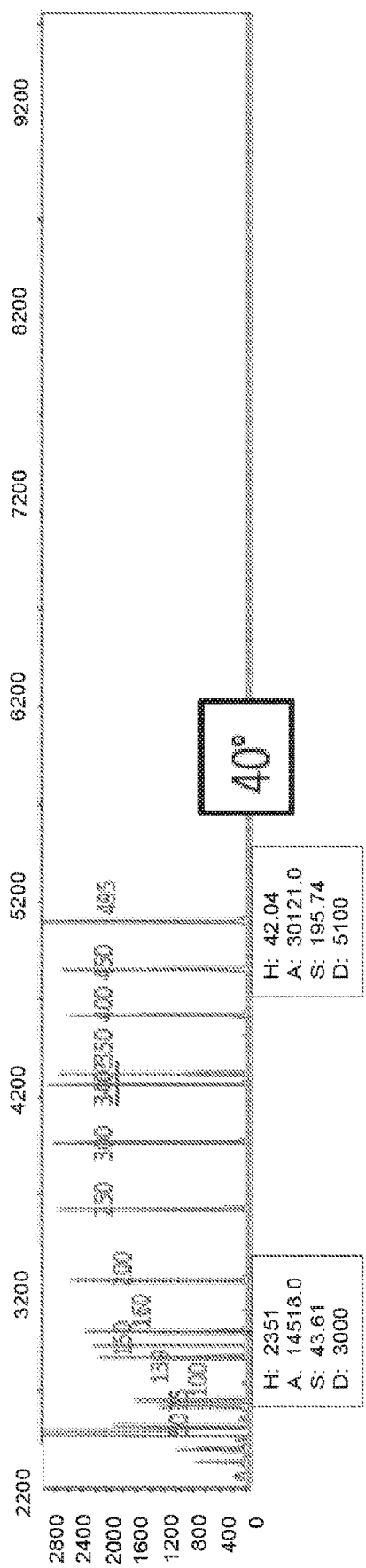
Figure 5D:
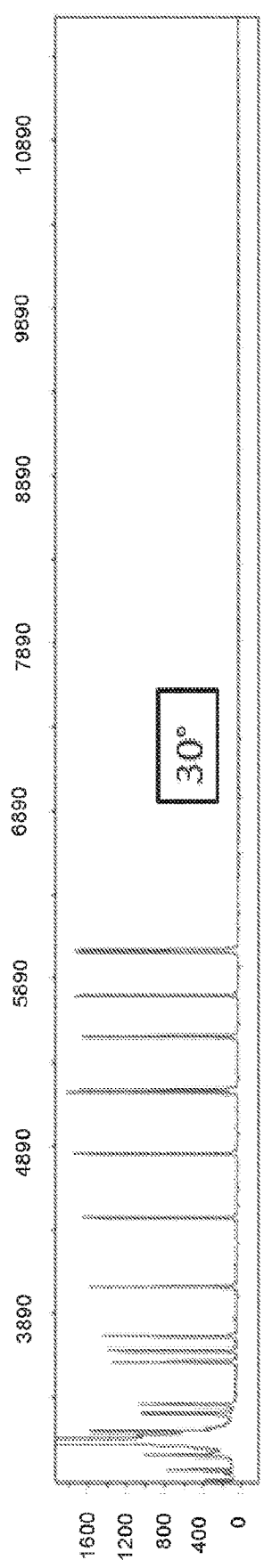

FIG. 3 is a graphical representation 300 of peak detection and normalization according to various embodiments described herein. The normalized value indicates the relative concentration of a sample of double stranded nucleic acid. Graphical representation 300 may be displayed on a graphical user interface (GUI).

For a double stranded nucleic acid, the peaks are determined from the electropherogram. In the example shown in FIG. 3, peaks 302 and 308 are detected. Start point 304 and end point 306 of peak 302 is determined. Similarly, start point 310 and end point 312 is determined for peak 308. The start and end points may be manually by a user or automatically determined by a processor. Using the start and end points, the areas for peaks 302 and 308 are calculated.

The calculated areas are then divided by a standard area value to normalize the values. A standard area value may be the peak area of a reference single stranded nucleic acid of size 100 in some embodiments. However, other normalizing peak area values may be used to normalize the areas. A peak generated by a known stable size reference single stranded nucleic acid may be used to normalize the area values.

FIG. 4 illustrates data associated with normalizing the peak areas of a double stranded nucleic acid. The peak normalization areas indicate a relative concentration of the double stranded nucleic acid in the sample according to various embodiments described herein.

Various embodiments of methods and system to quantitate nucleic acids in the plurality of double stranded nucleic acids are further described below with reference to FIGS. 12 and 13.

Plurality of Double Stranded Nucleic Acids.

A plurality of double-stranded nucleic acids may be obtained in a variety of ways. A sample which may contain DNA or RNA, may be interrogated with a set of primers directed at a preselected set of sequences. The set of primers may be a highly multiplexed set of primers. The primer set may be directed at a set of sequences targeted as potentially relevant for the specific study, such as exploring sequences related to one or more oncological targets. The primers may be extended to provide a library of double stranded nucleic acids. The extension may occur in an amplification method. Alternatively, the sample containing DNA and/or RNA may be subjected to whole genome, PCR free preparations to provide a library of double stranded nucleic acids. Sample nucleic acid may be subjected to one or more of fragmentation, ligation with adaptors, and amplification methods to provide the plurality of double stranded nucleic acids. For example, library preparation of fragmented DNA, for use with the Ion Torrent™ sequencing platform, involves repair of 3' and 5' ends before ligation to an adaptor. After ligation, adaptor-DNA constructs are purified and size selected, and amplified via polymerase chain reaction (PCR).

Sizing Ladder.

A single stranded sizing ladder may include a plurality of detectably labeled fragments. The fragments may be of predetermined length. The detectably labeled fragments of the single stranded sizing ladder may be covalently labeled with a second dye. In some embodiments, the second dye may be configured to be spectrally resolvable from the first dye. The first dye may not substantially label the detectably labeled fragments of the single stranded sizing ladder. In some embodiments, the second dye, which is covalently attached to the fragments of the single stranded sizing ladder, may be observable at the same wavelength as the first dye. A single stranded sizing ladder may be constructed in various ways. One method is described in U.S. Pat. No. 7,700,287, herein incorporated by reference in its entirety.

Dyes.

A dye may be a visible dye, a fluorescent dye, or a chemiluminescent dye. In various embodiments, a fluorescent dye, which may be used as the first dye that labels the plurality of double stranded nucleic acids or may be used as the second dye that labels the sizing ladder, is a pyrene dye, a naphthalene dye, an aminopyridine dye, a xanthene dye which may be a fluorescein, rhodol or rhodamine dye, a cyanine dye, a coumarin dye, a borapolyazaindacine dye, a benzofuran dye, or an indole dye. In other embodiments, the fluorescent dye is a fluorescein dye or a rhodamine dye.

In some embodiments a xanthene dye that may be used as the first dye labeling the plurality of double stranded nucleic acids or may be used to label the single stranded sizing ladder, is a xanthene dye having a structure of Formula X:

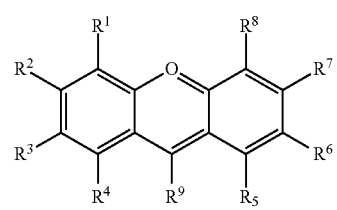

Formula X or a tautomer or salt thereof;

wherein $R^1$, $R^2$, $R^3$, $R^4$, $R^5$, $R^6$, $R^7$, $R^8$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonyl-amino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, sulfo, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or one or more of $R^1$ and $R^2$, $R^2$ and $R^3$, Wand $R^4$, $R^5$ and $R^6$, $R^6$ and $R^7$ or $R^7$ and $R^8$ are taken together to form a fused unsubstituted aryl, fused substituted aryl, fused unsubstituted heteroaryl, fused substituted heteroaryl, unsaturated unsubstituted heterocycyl, unsaturated substituted heterocycyl, saturated unsubstituted heterocycyl or saturated substituted heterocycyl ring; and one of $R^1$, $R^2$, $R^3$, $R^4$, $R^5$, $R^6$, $R^7$, $R^8$ and $R^9$ may be the point of attachment to a first linker through a covalent bond, -alkyl-, -substituted alkyl-, -alkenyl-, -substituted alkenyl-,-carboxamidyl-, substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-, -substituted carbonyl-, -alkoxy-, -substituted alkoxy-,-sulfonamidyl-, -substituted sulfonamidyl-, -thio-, -amino-, or -substituted amino-, when the xanthene dye is attached covalently. When the first linker attaches the dye to a single stranded sizing ladder, for example, the first linker may be a covalent bond or may also include 1-100 non-hydrogen atoms including carbon, nitrogen, oxygen, sulfur, and phosphorus atoms in any arrangement and oxidative states. The first linker may be linear or branched, and may include cyclic moieties including carbocyclic, heterocyclic, aryl, or heteroaryl rings. The xanthene dye, if part of an energy transfer dye, may be linked via the first linker to a second dye, forming the other partner in an energy transfer pair, where the second dye is the moiety attached to the sizing ladder thru a second linker which may be the same or may be different from the first linker. The second linker may have any structure as defined above for the first linker.

In some embodiments, $R^9$ may be a substituted aryl. In yet other embodiments, the substituted aryl $R^9$ is substituted with two halo substituents, which may be the same or different halide. In other embodiments, the two halo substituents are each chloro. In yet other embodiments, the substituted aryl $R^9$ has two halo substituents and a third substituent is the point of attachment to $L_1$ through a covalent bond, -alkyl-, -substituted alkyl-, -alkenyl-, -substituted alkenyl-,-carboxamidyl-, substituted carboxamidyl-, -heterocyclyl-, -substituted heterocyclyl-, -aryl-, -substituted aryl-, -heteroaryl-, -substituted heteroaryl-, -cycloalkyl-, -substituted cycloalkyl-, -carbonyl-,-substituted carbonyl-, -alkoxy-, -substituted alkoxy-,-sulfonamidyl-, -substituted sulfonamidyl-, -thio-, -amino-, or -substituted amino-. In some embodiments, at least one $R^9$ substituent is a covalent bond, -alkyl-, -substituted alkyl-, -carboxamidyl-, substituted carboxamidyl-, -carbonyl-, -substituted carbonyl-, -alkoxy-, -substituted alkoxy-,-sulfonamidyl-, or -substituted sulfonamidyl-. In yet other embodiments, the at least one $R^9$ substituent is a covalent bond, -carboxamidyl-, substituted carboxamidyl-, -carbonyl-, -substituted carbonyl-, -alkoxy-, -substituted alkoxy-,-sulfonamidyl-, or -substituted sulfonamidyl-. In other embodiments, $R^9$ is hydrogen.

In some embodiments, the xanthene dye has $R^2$ and $R^7$ selected from the group consisting of alkoxy, substituted alkoxy, acyl, acylamino, acyloxy, carboxyl ester)oxy and hydroxy, with the proviso that at least one of $R^2$ and $R^7$ is hydroxy, and the xanthene dye is a fluorescein.

In other embodiments, the xanthene dye has $R^2$ and $R^7$ selected from the group consisting of amino, substituted amino, aminocarbonyl, aminothiocarbonyl, aminocarbonylamino, aminothiocarbonyl-amino, aminocarbonyloxy, aminosulfonyl, aminosulfonyloxy, aminosulfonylamino, amidino, (carboxyl ester)amino, heteroaryl, substituted heteroaryl, heterocyclyl, and substituted heterocyclyl, where each of $R^2$ and $R^7$ are connected to the core of the xanthene dye via a nitrogen atom of the substituent, thereby forming a rhodamine dye. In some embodiments, $R^8$ and Fe are taken together and form an unsaturated unsubstituted heterocycyl, unsaturated substituted heterocycyl, saturated unsubstituted heterocycyl or saturated substituted heterocycyl ring, where the ring has 5-7 members. In other embodiments, $R^1$ and $R^2$ are taken together and form an unsaturated unsubstituted heterocycyl, unsaturated substituted heterocycyl, saturated unsubstituted heterocycyl or saturated substituted heterocycyl ring, where the ring has 5-7 members.

In some embodiments, when $R^9$ is hydrogen, $R^5$ and $R^6$ are taken together to form a fused 5-6 membered aromatic or heteroaromatic ring which may be unsubstituted or substituted. In other embodiments, $R^9$ is hydrogen, $R^3$ and $R^4$ are taken together to form a fused 5-6 membered aromatic or heteroaromatic ring which may be unsubstituted or substituted. In some embodiments, $R^9$ is hydrogen, Wand $R^4$ are taken together to form a fused 5-6 membered aromatic or heteroaromatic ring which may be unsubstituted or substituted, and $R^5$ and Fe are taken together to form a fused 5-6 membered aromatic or heteroaromatic ring which may be unsubstituted or substituted.

Synthesis of some exemplary xanthene dyes that are suitable for use in the methods, systems, compositions and kits are described in U.S. Pat. Nos. 5,188,934; 5,770,716; 6,008,379, 6,025,505; 6,080,852; RE39663, and 6,051,719, amongst others and is in no way a limiting list. Each of these patents is herein incorporated by reference in its entirety.

In various embodiments, more than one dye may be incorporated in the labeling species that act as either the first dye, which labels the plurality of double stranded nucleic acids, or the second dye, which detectably labels the single stranded sizing ladder in the methods described here. When more than one dye is incorporated in the labeling species, the fluorescent dye may be a polymeric dye or an energy transfer dye. An energy transfer dye may have a donor dye and an acceptor dye, where the donor dye is configured to absorb energy at one wavelength and emit energy at a second wavelength which emitted energy excites the acceptor dye at the second wavelength. The acceptor dye then emits at a third wavelength, which is detectable. In some embodiments, an energy transfer dye may have a donor dye that is a fluorescein dye, and a rhodamine acceptor dye. Any suitable combination of classes of donor and acceptor dyes may be used. If more than one labeling species is used in the methods described here, then the more than one energy transfer dyes are configured to be detected at different wavelengths, and therefore are spectrally resolvable.

In some embodiments, the dye is NBD, Texas Red®, FAM™, JOE™, TAMRA™, ROX™, VIC™, HEX™, TET™, NED™, PET®, BigDye®, LIZ® or a tautomer or salt thereof. When any of these dyes are covalently attached, the dye may be attached via a linker. The linker may be a covalent bond or may also include 1-100 non-hydrogen atoms including carbon, nitrogen, oxygen, sulfur, and phosphorus atoms in any arrangement and oxidative states. The linker may be linear or branched, and may include cyclic moieties including carbocyclic, heterocyclic, aryl, or heteroaryl rings. In other embodiments, the energy transfer dye is attached to the linker at the same point of attachment, i.e. is attached at one atom of the labeling species. In other embodiments, the energy transfer dye is attached to different atoms in the labeling species, while still being configured to donate and accept excitation energy for energy transfer dye performance.

In some embodiments, the single stranded sizing ladder may be covalently labeled with a xanthene dye. The xanthene dye may be a dye of Formula X as described above. The xanthene dye may be attached to the sizing ladder via a linker, as described above. The xanthene dye may be a rhodamine or a fluorescein dye. In other embodiments, the sizing ladder may be covalently labeled with an energy transfer dye where either of the donor or acceptor dye is attached to the sizing ladder via a linker. An energy transfer dye that is suitable for covalently labeling the sizing ladder may include a xanthene dye as either or both of the donor and acceptor dyes. In some embodiments, the acceptor dye is a rhodamine dye. In other embodiments, the single stranded sizing ladder may be covalently labeled with a cyanine dye.

The plurality of double stranded nucleic acids is labeled with a first dye. The first dye may label the plurality of double stranded nucleic acids non-covalently. The mode of non-covalent labeling may include one or more of intercalation (including bis-intercalation), minor-groove binding, major groove binding, external binding or specific motif recognition. In some embodiments, the first dye may label each of the plurality of double stranded nucleic acids at least via intercalation. In other embodiments, the first dye may label double stranded nucleic acid by bis-intercalation. In various embodiments, when the first dye labels double stranded nucleic acid as an intercalator, other binding modes may also be operating to some degree. In various embodiments, the first dye is configured to label the plurality of double stranded nucleic acids and it is configured to not label the single stranded sizing ladder, whether it is detectably labeled or not. In some embodiments, the first dye is configured to label at least a detectable portion of the plurality of double stranded nucleic acids while not labeling the single stranded sizing ladder. A suitable first dye may be selected from the dyes described here or known in the art.

In some embodiments, the first dye is a cyanine dye, acridine dye, or phenanthridinium dye, where the first dye has a fluorescence emission maximum in the range of about 450 nm to about 750 nm. The cyanine dye may be a monomethine cyanine dye. The cyanine dye may be an unsymmetric cyanine dye. The cyanine dye may be a dimeric cyanine dye.

In some embodiments, the cyanine dye has a structure of Formula I:

Formula I

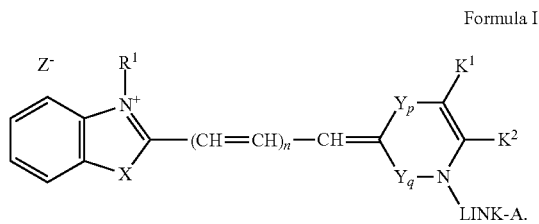

The ring member X may be O, S, Se, or $C(CH_3)$. The nitrogen substituent $R^1$ is $C_1$-$C_6$ alkyl. In some embodiments, $R^1$ is methyl. The methine bridge may be monomethine, trimethine or pentamethine, where n=0, 1 or 2, respectively. The aromatic ring component Y is:

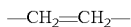

with subscripts p and q equal to 0 or 1, such that p+q=1. Ring substituents $K^1$ and $K^2$ may be the same or different, and are independently hydrogen, an alkyl group having 1-6 carbons, or aryl; or $K^1$ and $K^2$ taken in combination complete a 6-membered aromatic ring to yield a quinolinium ring system.

LINK is an aliphatic chain containing a backbone of 4 to 19 methylene groups ($-CH_2-$), which is optionally interspersed at one or more intervals with a heteroatom, each of which is independently N, O or S, wherein each N heteroatom is additionally substituted by 1-2 H, or 1-2 alkyl groups with 1 to 6 carbons, which alkyl substituents may be the same or different, provided that any heteroatom is separated from another heteroatom by at least 2 methylene groups, wherein one methylene terminus of LINK is attached to a nitrogen atom of the pyridinium or quinolinium heterocycle and another methylene terminus of LINK is attached to A, except that where A is H or $CH_3$, LINK must contain at least one N heteroatom. Preferred LINK chains contain two or three heteroatoms, each separated from one another by three methylenes. Preferably the heteroatom is N, where N is substituted by two alkyl groups of 1-6 carbons, which may be the same or different. Preferably LINK contains 12 or less methylene groups.

A is either H, $CH_3$ or is

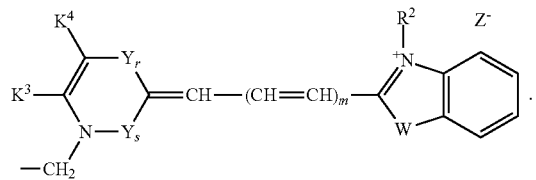

The ring member W is O, S, Se, or $C(CH_3)$. The nitrogen substituent $R^2$ is $C_1$-$C_6$ alkyl, preferably methyl. The methine bridge is either monomethine, trimethine or pentamethine, for m=0, 1 or 2. The aromatic ring component Y is $-CH_2=CH_2-$, with subscripts r and s equal to 0 or 1, such that r+s=1. Ring substituents $K^3$ and $K^4$ may be the same or different, and are independently hydrogen, an alkyl group having 1-6 carbons, or aryl; or $K^3$ and $K^4$ taken in combination complete a 6-membered aromatic ring to yield a quinolinium ring system.

When A is not H or $CH_3$, m and n can be the same or different, and W and X can be the same or different. Methods of synthesis of these dyes may be found in U.S. Pat. Nos. 5,534,416; 5,321,130, and 5,435,134, each of which is herein incorporated by reference in its entirety, and references therein.

In various embodiments, the first dye may be a dye having the structure of Formula I where X is O. In various embodiments the first dye may have a structure of Formula I where $R^1$ is methyl. In various embodiments, the first dye may have a structure of Formula 1 where the methine bridge is monomethine, where n is 0. In various embodiments the first dye may have a structure of Formula I where $Y_p$ has p=0 and $Y_q$ has q=1. In various embodiments the first dye may have a structure of Formula I where $K^1$ and $K^2$ are taken together in combination to complete a 6 membered aromatic ring yielding a quinolinium ring system. In various embodiments the first dye may have a structure of Formula I where LINK has a backbone of 9-12 methylene groups and interspersed at two intervals with a nitrogen atom, where each nitrogen atom may be mono- or di-substituted with $C_1$-$C_6$ carbons, and further where the two nitrogen atoms are separated from each other by at least two methylene groups. In various embodiments the first dye may have a structure of Formula I where A has a structure of Formula A:

Formula A

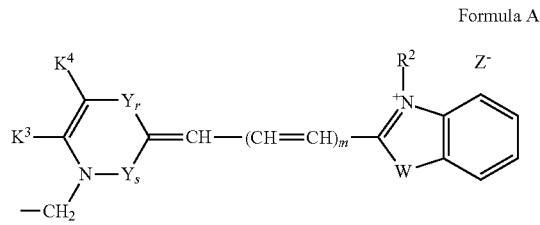

where W is O. In various embodiments, the first dye of Formula I may have a structure including Formula A where $R^2$ may be methyl. In various embodiments, the first dye of Formula I may have a structure including Formula A where the methine bridge is monomethine where m=0. In various embodiments, the first dye of Formula I may have a structure including Formula A where $Y_r$ has r=0 and $Y_s$ has s=1. In various embodiments, the first dye of Formula I may have a structure including Formula A where $K^3$ and $K^4$ are taken in combination to complete a 6 membered aromatic ring to yield a quinolinium ring system. In various embodiments, the first dye having a structure of Formula I may have any of these limitations in any combination.

In some embodiments, the first dye may be a cyanine dye of Formula I where X is O; $R^1$ is methyl; the methine bridge is monomethine, where n is 0; $Y_p$ has p=0 and $Y_q$ has q=1; $K^1$ and $K^2$ are taken together in combination to complete a 6 membered aromatic ring yielding a quinolinium ring system; LINK has a backbone of 9-12 methylene groups and interspersed at two intervals with a nitrogen atom, where each nitrogen atom is mono- or di-substituted with $C_1$-$C_6$ carbons, and further where the two nitrogen atoms are separated from each other by at least two methylene groups; A has a structure of Formula A:

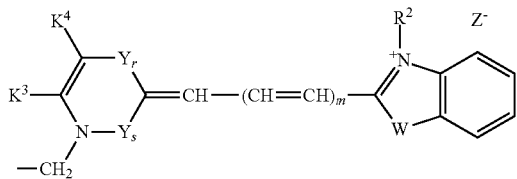

Formula A where W is O; $R^2$ is methyl; the methine bridge is monomethine where m=0; $Y_r$ has r=0 and $Y_s$ has s=1; and $K^3$ and $K^4$ are taken in combination to complete a 6 membered aromatic ring to yield a quinolinium ring system.

In some embodiments, the first dye is a cyanine dye, and may be selected from the group consisting of YOYO-1, YOYO-3, TOTO-1, TOTO-3, BOBO-1, BOBO-3, POPO-1, POPO-3, LOLO-1, and LOLO-3.

In other embodiments, the first dye may be a cyanine dye having a structure of Formula II:

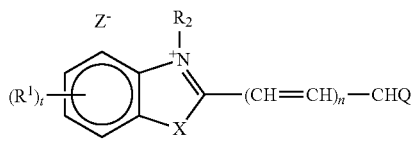

Formula II wherein each $R^1$ is independently H, a $C_1$-$C_6$ alkyl group, a trifluoromethyl, a halogen, —$OR^8$, —$SR^8$ or —($NR^8$ $R^9$) where $R^8$ and $R^9$, which can be the same or different, are independently H, unsubstituted or substituted $C_1$-$C_6$ alkyl groups, 1-2 alicyclic rings, 1-2 heteroalicyclic rings, 1-2 aromatic rings or 1-2 heteroaromatic rings containing 1-4 heteroatoms, wherein the hetero atoms are O, N or S; or $R^8$ and $R^9$ taken in together are —$(CH_2)_2$-L-$(CH_2)_2$—, where L is a single bond, —O—, —$CH_2$—, or —$NR_{10}$—, where $R^{10}$ is H or a $C_1$-$C_6$ alkyl group; and t=1-4;
$R^2$ is a $C_1$-$C_6$ alkyl group;
X is O, S, Se or —$NR^{15}$, where $R^{15}$ is H or a $C_1$-$C_6$ alkyl group; or X is $CR^{16}$ $R^{17}$ where $R^{16}$ and $R^{17}$, which may be the same or different, are independently $C_1$-$C_6$ alkyl groups, or $R^{16}$ and $R^{17}$ taken in combination complete a five or six membered saturated ring;
n=0, 1 or 2;
$Z^-$ is a biologically compatible counterion;
Q has the formula Q1 or Q2

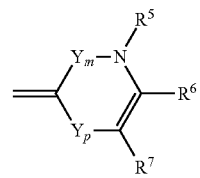

Q1

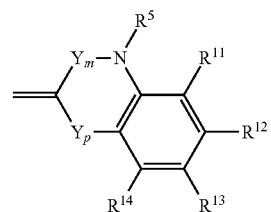

Q2 where Y is —$CR^3$=$CR^4$—; and p and m=0 or 1, such that p+m=1;
$R^5$ is $C_1$-$C_6$ alkyl, $C_1$-$C_6$ alkenyl, $C_1$-$C_6$ polyalkenyl, $C_1$-$C_6$ alkynyl or $C_1$-$C_6$ polyalkynyl group; or $R^5$ is an OMEGA;
$R^3$, $R^4$, $R^6$ and $R^7$, which may be the same or different, are independently H, $C_1$-$C_6$ alkyl, $C_1$-$C_6$ alkenyl, $C_1$-$C_6$ polyalkenyl, $C_1$-$C_6$ alkynyl, $C_1$-$C_6$ polyalkynyl group, halogen, —OH, $OR^8$, —$SR^8$, —($NR^8$ $R^9$), or —$OSO_2$ $R^{19}$ where $R^{19}$ is $C_1$-$C_6$ alkyl, $C_1$-$C_6$ perfluoroalkyl, aryl, or an OMEGA; or $R^6$ and $R^7$, taken in combination are —$(CH_2)_v$— where v=3 or 4, or $R^6$ and $R^7$ form a fused aromatic ring according to formula Q2;
$R^{11}$, $R^{12}$, $R^{13}$, and $R^{14}$, which may be the same or different, are independently H, $C_1$-$C_6$ alkyl, $C_1$-$C_6$ alkenyl, $C_1$-$C_6$ polyalkenyl, $C_1$-$C_6$ alkynyl, $C_1$-$C_6$ polyalkynyl group, halogen, an OMEGA, —OH, —$OR^8$, —$SR^8$, or —($NR^8R^9$);
OMEGA is a cyclohexyl, cyclohexenyl, morpholino, piperidinyl, naphthyl, phenyl, thienyl, benzothiazolyl, furanyl, oxazolyl, benzoxazolyl or pyridinyl that is unsubstituted or optionally substituted one or more times, independently, by halogen, alkyl, perfluoroalkyl, amino, alkylamino, dialkylamino, alkoxy or carboxyalkyl, having 1-6 carbons, and that is attached as $R^3$, $R^4$, $R^5$, $R^6$, $R^7$, $R^{12}$, $R^{13}$, or $R^{14}$ by a single bond;
such that at least one of $R^3$, $R^4$, $R^5$, $R^6$, $R^7$, $R^{11}$, $R^{12}$, $R^{13}$, and $R^{14}$ is an OMEGA, and, where more than one of $R^3$, $R^4$, $R^5$, $R^6$, $R^7$, $R^{11}$, $R^{12}$, $R^{13}$, and $R^{14}$ is an OMEGA, each OMEGA is optionally the same or different.

The $C_1$-$C_6$ alkyl substituents for $R^8$ and $R^9$ include substituted or unsubstituted amino groups. The substituted amino substituent may itself have one, two or three substituents which may be the same or different and which may be a $C_1$-$C_6$ alkyl group, a hydroxy substituted $C_1$-$C_6$ alkyl group, or a alkylaryl group where the aryl group has 6-10 carbons in one or more fused rings and further where the aryl group may be unsubstituted or substituted by 1-4 groups selected from $C_1$-$C_6$ alkoxy, $C_1$-$C_6$ alkyl, trifluoromethyl or halo.

Each of the alicyclic, heteroalicyclic, aromatic or heteroaromatic rings may be of $R^8$ and $R^9$ may be fused or not fused.

In some embodiments, when the first dye has a structure of Formula II and Q has the formula Q1, then n=0. In some embodiments, when the first dye has a structure of Formula II, X is O or S.

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

In various embodiments, the first dye is spectrally resolvable from a second dye labeling the detectably labeled single stranded sizing ladder.

Separation.

The mixture of the plurality of first dye-labeled double stranded nucleic acids and the detectably labeled single stranded sizing ladder is separated in a mobility dependent manner by migrating the mixture under the influence of an electric field in a channel. Electrophoresis can provide differential migration as mobility is dependent upon both size and charge characteristics. Migration under mobility dependent separation conditions will separate each of the plurality of first dye-labeled double stranded nucleic acids into bands or peaks having the same weight, within the limits of resolution of the system. In some embodiments, the limit may be about the weight of one nucleotide unit, for example, about 100 Daltons (Da). When the limit of resolution is about one nucleotide unit, each band or peak detected will differ from the preceding or following band or peak by about one nucleotide difference. In other embodiments, the limit of resolution may be the weight of about two nucleotides (200 Da) to about 5 nucleotides (500 Da). When the limit of resolution is about two nucleotides to about 5 nucleotides, each band or peak detected with differ from the preceding or following band or peak by about two to about five nucleotides. Each band or peak having the same weight, within the limits of resolution, may include one distinct nucleic acid or it may include a whole set of distinct nucleic acids of differing sequence but having the same weight/length and therefore, the same mobility under the mobility dependent separation conditions. In some embodiments, while the detectably labeled single stranded sizing ladder may be detected as a set of distinct and individual bands or peaks, the plurality of dye-labeled double stranded nucleic acids may not be detected as individual bands or peaks, but will be visible in an electropherogram as a broadened band, as the sum of most of the individual double stranded nucleic acids of the plurality will be of a molecular weight closely related to the others in the plurality.

Separation Medium.

The channel may contain a separation medium containing a buffer and additional components as described here, which may be selected to provide electrophoretic force to the plurality of first dye-labeled double stranded nucleic acids and the detectably labeled single stranded sizing ladder and may permit a distinct migration time to be detected for each of the fragments of the detectably labeled single stranded sizing ladder present in the electrophoretic separation, as well as a range of migration times for the plurality of first dye-labeled double stranded nucleic acids. The migration time of these species may be moderated by choice of electric field strength, length of channel, polarity, ionic species and ionic strength of the separation medium amongst other variables.

Separation Medium Includes a Sieving Medium.

In various embodiments, the channel may include a sieving polymer in the separation medium used for the separation of the mixture. A sieving polymer may be either a crosslinked physical gel or, more typically a non-crosslinked polymer present at high enough concentration to provide an entangled polymer network in the channel. The entanglement concentration threshold or higher concentrations provide a dynamic entangled network "pores" that smaller molecules can enter more frequently, leading to faster migration, while molecules larger than the "pores" travel by reptation which slows as size increases.

Sieving Polymers.

Any suitable sieving polymer may be used in the separations. In some embodiments, one or more water soluble, uncrosslinked polymers may be selected as sieving polymeric components of the separation medium. Some polymers that may be used as sieving polymers include polyacrylamide, including, for example, linear polyacrylamide (LPA); substituted polyacrylamides, including but not limited to polydimethylacrylamide (PDMA), poly N-methyl acrylamide, and co-polymers of substituted acrylamides with acrylamide, particularly LPA, of all physical types (block, graft or random); vinyl polymers, including but not limited to polyvinylpyrrolidone (PVP) or polyvinyloxazolidone; polysaccharide polymers such as methylcellulose, hydroxyethylcellulose or copolymers thereof; and polyether polymers such as PEO. Sieving polymers may be present in the separation medium in a concentration in a range of about 0.1% to about 10% by weight. In some embodiments, the sieving polymers are present in a range of about 0.1% to about 5% by weight. Their average molecular weight $M_w$ may be in a range from about 50,000 Da to about 6 MDa. In some embodiments, the $M_w$ for a sieving polymer may be in a range from about 500.00 Da to about 3 MDa. The average molecular weight $M_w$ may be obtained by gel permeation chromatography and may also include detection by light scattering.

Other Polymeric Components.

In some embodiments, the polymeric components of the separation medium may include other polymers which may contribute other behaviors in addition or in place of sieving behaviors. One exemplary, but not limiting, additional behavior is that of surface interaction with the channel wall to decrease migration band irregularities due to non-uniform electroosmosis, excess electroosmotic flow or solute adsorption, as described below. A surface interaction polymer may be an uncharged, water soluble, silica-adsorbing polymer, including, but not limited to polymers of acrylamide and acrylamide derivatives such as PDMA and PHEA (poly-N-hydroxyethylacrylamide), polysaccharide and its derivatives such as dextran, HPMC (hydroxypropyl methyl cellulose), MC, HEC (hydroxyethyl cellulose), HPC (hydroxypropyl cellulose), MHEC (methylhydroxyethylcellulose), and other polymers such as PVP, PVA (polyvinyl alcohol) and PEG (polyethylene glycol). In some embodiments, the surface interaction polymer may be a copolymer of acrylamide and acrylamide derivatives such as PDMA or PHEA, including random, block or graft copolymers. In some other embodiments, a charged, water soluble silica-adsorbing polymer may be used as a surface interaction polymer, including but not limited to cationic HEC (hydroxyethyl cellulose quaternized with tertiary ammonium moieties) or cationic starch derivatives.

In some embodiments, a sieving polymer is the same polymer as a surface interaction polymer. In other embodiments, the sieving polymer is a different polymer from the surface interaction polymer.

Buffer.

A buffer composition configured to permit migration of the mixture of the plurality of first dye-labeled double stranded nucleic acids and the detectably labeled single stranded sizing ladder may be included in the channel when the mixture is subjected to the influence of an electric field. Any suitable buffer may be used. A buffer for use in CE may have one or more of the following properties: good buffering capacity in the pH range of choice; low absorbance at the wavelength of detection; large, minimally-charged ions, which is useful to minimize current generation.

Effective buffer systems have a range of approximately two pH units centered around the pKa value. Polybasic buffers have more than one useful pKa and thus can be used in more than one pH range. Useful buffers and their pKa include but are not limited to: Phosphate 2.12 (pKa1); Citrate 3.06 (pKa1); Formate 3.75; Succinate 4.19 (pKa 1); Citrate 4.74 (pKa2); Acetate 4.75; Citrate 5.40 (pKa3); Succinate 5.57 (pKa2); MES 6.15; ADA 6.60; BIS-TRIS propane 6.80; PIPES 6.80; ACES 6.90; MOPSO 6.90; Imidazole 7.00; MOPS 7.20; Phosphate 7.21 (pKa2); TES 7.50; HEPES 7.55; HEPPS 8.00; TRICINE 8.15; Glycine amide, 8.20; Glycylglycine 8.25; TRIS 8.30; BICINE 8.35; Morpholine 8.49; Borate 9.24; CHES 9.50; CHAPSO 9.60; CAPS 10.40; and Phosphate 12.32 (pKa 3). Tris, borate, histidine, or CAPS are especially useful, as these buffer ions are generally large and can be used in high concentrations without generating significant currents. However, UV absorbance may also be a consideration in using any of these.

Buffer Additives.

Numerous types of surfactants can be used in the separations, including anionic, cationic, zwitterionic, or non-ionic. Ionic surfactant molecules can act as solubilizing agents for hydrophobic solutes, as ion-pairing reagents, or as wall modifiers. The interaction of the surfactant with the solute can occur via two mechanisms; ionic interactions with the charged end of the surfactant and/or through hydrophobic interactions between the alkyl chain and hydrophobic moieties of the solute. In addition to interacting with the solute, many surfactants can adsorb to the capillary wall, modifying electroosmotic flow (EOF) and also limiting potential solute adsorption. Depending on surfactant charge, EOF can be increased, reduced, or reversed.

Other additives may include adding a chirality selective agent to the running buffer. These agents can be cyclodextrins, crown ethers, bile salts, copper (II)-aspartate complexes, for example, and their performance may also be moderated by the addition of modifiers such as alcohols, surfactants, urea, and metal ions.

In some embodiments, glycerol may be added to the buffer to assist with fluorescence peak detection.

Denaturing Additives.

In some embodiments, nucleic acid mobility dependent separations may include one or more denaturants. Denaturants may be used in a separation buffer and/or separation medium to disrupt any secondary or tertiary structure in a nucleic acid under investigation, which may affect its mobility. Denaturants useful for nucleic acid separations include but are not limited to one or more of urea, formamide, pyrrolidine, dimethylsulfoxide (DMSO), and glyoxal. When formamide is used as a denaturing additive, it may be present at about 40% to about 90% by weight in the separation medium, when completely denaturing conditions are desired. When urea is used as a denaturing additive, it may be present at about 4M to about 8M in the separation medium, when completely denaturing conditions are desired. For double stranded nucleic acid, the denaturing effects of one or more denaturant additives may be modified by other reaction conditions such as run temperature selection or joule heating.

In other embodiments, the mobility dependent separation may use a separation buffer including no denaturing additives. In these separations, the double stranded nucleic acids labeled with the first dye may be most strongly hybridized to each other and maintain the greatest amount of first dye labeling the pair. Secondary and tertiary structure may be retained in separations under these conditions, or may be moderated by other reaction conditions such as temperature selection or joule heating. Depending on the design of the single stranded sizing ladder, behavior may be altered under non-denaturing conditions.

Channel Surface Treatment.

In some embodiments, the inner surface of the channel may be treated to minimize migration band irregularities due to non-uniform electroosmosis, excess electroosmotic flow or solute adsorption. Coating the channel wall can be a useful method for decreasing solute adsorption by decreasing the free energy of interaction. Coatings may include buffer additives such as hydrophilic polymers or detergents, providing dynamic reduction of wall/solute interactions, or by covalent modification of the wall. Both can be used to eliminate or reverse the charge on the channel wall, alter hydrophobicity and limit nonspecific adsorption.

Treatment with polyacrylamide or polyethylene glycol, for example, may reduce or help to eliminate electroosmotic flow (EOF). This results from both decreased effective wall charge and increased viscosity at the wall. Treatment with cationic groups may reverse the EOF. Some examples of cationic polymers containing tertiary amino groups, useful as additives, include but are not limited to Biobrene™ Plus (Life Technologies Catalog number: 400385, CAS-No 9011-04-5) and Hexadimethrine bromide, sold as Polybrene® (Sigma Aldrich Catalog Numbers: 107689).

Compositions.

In another aspect, compositions are provided. A composition for determining a range of lengths of a plurality of double stranded nucleic acids may include a first dye configured to label a double stranded nucleic acid; a plurality of double stranded nucleic acids; and a detectably labeled single stranded sizing ladder. The plurality of double stranded nucleic acids may be DNA, RNA or a combination of both. The first dye may be configured to not label a single stranded nucleic acid, or substantially not label single stranded nucleic acid. In various embodiments, the first dye may label the double stranded nucleic acid non-covalently. In some embodiments, the first dye may be an intercalator. In various embodiments, the detectably labeled single stranded sizing ladder may be covalently labeled. In various embodiments, the detectably labeled single stranded sizing ladder may be fluorescently labeled. The detectably labeled single stranded sizing ladder may be labeled with a pyrene, naphthalene, aminopyridine, xanthene, cyanine, coumarin, borapolyazaindacine, benzofuran, or indole dye. In some embodiments, the first dye may be a cyanine dye, acridine dye, or phenanthridinium dye. In some embodiments, the first dye may be a cyanine dye. The cyanine first dye of the composition may be a monomethine cyanine. The cyanine first dye of the composition may be a dimeric cyanine. The first dye may be a dye of Formula I or a dye of Formula II as described above, or any of the specific embodiments included in that general formula.

In various embodiments, the first dye may be spectrally resolvable from a second dye which labels the detectably labeled single stranded sizing ladder. The composition may further include a denaturing additive.

Kits.

A kit for determining a range of lengths of a plurality of double stranded nucleic acids may include a first dye configured to label a double stranded nucleic acid and a detectably labeled single stranded sizing ladder. In some embodiments the first dye may substantially label a double stranded nucleic acid. In other embodiments, first dye may substantially label a double stranded nucleic acid not label a single stranded nucleic acid. In some embodiments, the first dye may be a cyanine dye. The cyanine dye may be a monomethine cyanine. In other embodiments, the first dye may be a cyanine dye, acridine dye, or phenanthridinium dye. In some embodiments, the first dye may label the double stranded nucleic acid non-covalently. In some embodiments, the first dye may be an intercalator. The first dye may be a dye of Formula I or a dye of Formula II as described above, or any of the specific embodiments included in that general formula.

The detectably labeled single stranded sizing ladder of the kit may be covalently labeled. In some embodiments, the detectably labeled single stranded sizing ladder may be fluorescently labeled. In various embodiments, the detectably labeled single stranded sizing ladder may be labeled with pyrene, naphthalene, aminopyridine, xanthene, cyanine, coumarin, borapolyazaindacine, benzofuran, or indole dye. Any of these dyes may be used as a second dye to label the singly stranded sizing ladder where the first dye used to label the plurality of double stranded nucleic acids may be a cyanine dye, acridine dye, or phenanthridinium dye. In various embodiments, the first dye may be spectrally resolvable from a second dye labeling the detectably labeled single stranded sizing ladder.

The kit may further include a channel. The channel may be incorporated in a microfluidic chip. In various embodiments, the channel includes a separation medium. The channel may include a denaturing additive. The channel may include a buffer solution.

A kit for quantifying the amount of a plurality of double stranded nucleic acids may have any of the components of the above kit in any combination.

As used herein, the term "kit" refers to any delivery system for delivering materials. In the context of reaction assays, such delivery systems include systems that allow for the storage, transport, or delivery of reaction reagents (e.g., oligonucleotides, enzymes, primer set(s), etc. in the appropriate containers) and/or supporting materials (e.g., buffers, written instructions for performing the assay etc.) from one location to another. For example, kits can include one or more enclosures (e.g., boxes) containing the relevant reaction reagents and/or supporting materials. As used herein, the term "fragmented kit" refers to a delivery system comprising two or more separate containers that each contains a subportion of the total kit components. The containers may be purchased and/or delivered to the intended recipient together or separately. For example, a first container may contain an enzyme for use in an assay, while a second container contains oligonucleotides. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

Systems. A system for determining a range of lengths of a plurality of double stranded nucleic acids may include a reactor vessel configured for a) contacting a first dye with a plurality of double stranded nucleic acids, where the first dye labels each of the plurality of double stranded nucleic acids, and b) permitting addition of a detectably labeled single stranded sizing ladder The system may include a channel configured to migrate a mixture of the detectably labeled single stranded sizing ladder and a plurality of first dye-labeled double stranded nucleic acids; an anode and a cathode operably connected to the channel, configured to provide an electric field to the channel; and a detector configured to detect the first dye and a label of the detectably labeled single stranded sizing ladder.

The detector may detect uv absorbance, visible light absorbance, fluorescence, or chemiluminescence.

The system may further include a temperature controllable environment for the channel. In other embodiments, the system may further include a temperature controllable environment for the reactor vessel. The system may further include a data processor operably connected to the detector.

In the channel of the system, the channel may further include a separation medium. The separation medium may include a sieving medium. The channel may further include a denaturing additive. In some embodiments, the channel may be configured to be part of a microfluidic chip. In other embodiments, the channel may be an electrophoretic capillary. In various embodiments, the channel is part of a multichannel array.

An apparatus for nucleic acid analysis may include: (1) at least one loading well, which may be the same or different from the reactor vessel, configured to receive a plurality of double stranded nucleic acids; (2) at least one channel arranged in correspondence with the reactor vessel; and optionally (3) at least one eluting well arranged in correspondence with the channel and adapted to receive a portion of the first-dye labeled plurality of double stranded nucleic acids having traversed the channel. In various embodiments, a plurality of loading wells (alternatively reactor vessels) are arranged in correspondence with a plurality of channels, and optionally each of the plurality of channels is arranged in correspondence with a respective eluting well.

Each loading well, which may be the reactor vessel, may be a receptacle in fluid communication through an ion permeable membrane with its respective channel. Each loading well may have a volume capacity of between about 10 µl and about 500 µl, or of between about 50 µl and about 150 µl, for example. Each eluting well may have a volume capacity of between about 10 µl and about 500 µl, or of between about 50 µl and about 150 µl, for example. The apparatus may further include a reservoir including a buffer solution, the reservoir being in fluid communication through an ion permeable membrane with the loading well. The buffer solution may be any suitable buffer for separating labeled nucleic acids. The apparatus may further include a sample loader configured to load samples in the reactor vessels.

If a plurality of channels is present, the plurality of channels may be substantially parallel to one another. A channel may have a substantially circular cross-section, or may have a substantially rectangular cross-section, for example. The plurality of channels may be connected structurally to form a channel array unit that is removable as a whole, and may further include first and second support structures arranged at opposite sides so as to form a single channel array unit. In some embodiments, there are at least two channels in an array, at least three channels in an array, or at least four channels in an array. In various other embodiments, there are at least five channels in an array. The channel array unit may be configured for a single use and disposable. A channel may be configured for a single use and disposable. A total length of a channel may be between about 10 cm to about 50 cm, about 10 cm to about 30 cm, or may be about 10 cm, for example. In some embodiments, the channel may have a length of less than 10 cm. The channel array may include at least two channels, at least three channels, at least four channels, at least five channels, at least ten channels, or at least twenty channels, for example. A channel may have an internal diameter of between about 150 micrometers and about 250 micrometers, or between about 50 micrometers and about 100 micrometers, or between about 0.1 millimeter and about 2.5 millimeters, or between about 0.5 millimeter and about 1.5 millimeters, for example.

The apparatus may further include an ion permeable membrane arranged between the loading well (or reactor vessel) and the channel. The apparatus may further include at least two electrodes arranged on opposite sides of the channel, and the at least two electrodes may be platinum electrodes and may include a positive electrode arranged between the channel and the eluting well and a negative electrode arranged between the channel and the loading well. The apparatus may further include a power source connected to the at least two electrodes and configured to subject at least part of the channel to an electric field. The electric field may have an intensity of between about 200 V/cm and about 400 V/cm, or of between about 250 V/cm and about 350 V/cm, for example. The apparatus may further include a light source configured to subject at least one region of the channel to electromagnetic radiation, and the light source may be a diode laser, a blue Argon ion laser, or a yellow Krypton ion laser, for example. The electromagnetic radiation may be radiation having a wavelength in the range of about 400-500 nm or in the range of about 500-600 nm, for example. The apparatus may further include a fluorescence detector configured to detect fluorescence emitted from the capillaries, and the fluorescence detector may be a CCD camera, a CMOS camera or a PMT detector. In some embodiments, a photomultiplier tube (PMT) detector may be included to provide greater dynamic range. In some embodiments, the apparatus may further include a bandpass filter arranged between the channel and the fluorescence detector and be configured to allow radiation having a wavelength of about 510 nm or greater to pass. In some embodiments, the apparatus may include a bandwidth filter arranged between the channel and the fluorescence detector and is configured to allow radiation having a wavelength between about 530 nm to about 850 nm to pass. The apparatus may be a bench top apparatus, and may have a largest width, depth, or height that does not exceed about twelve inches.

The apparatus may further include a peak processor configured to process a peak related to fluorescence detected by the fluorescence detector, and the peak processor may be configured to generate an electropherogram showing peaks representing labeled nucleic acids having migrated through the channel so as to reveal a time point at which each nucleic acid passed across the fluorescence detector before eluting off the end of the channel. The apparatus may further include a computing system in communication with the fluorescence detector, where the computing system is configured to process a peak related to fluorescence detected by the fluorescence detector. The computing system may be configured to generate an electropherogram showing peaks representing labeled nucleic acids of equivalent apparent "size" having migrated through the channel so as to reveal a time point at which each nucleic acid passed across the fluorescence detector before eluting off the end of the channel.

A computing system may include or be configured to calculate an empirically-derived correlation, and may include or be configured to access and run a computer program product configured to compare the stored empirically-derived correlation migration times with determined migration times obtained by running an experiment with the apparatus to identify individual nucleic acids having migrated through the channel during the experiment.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

Figure 8:
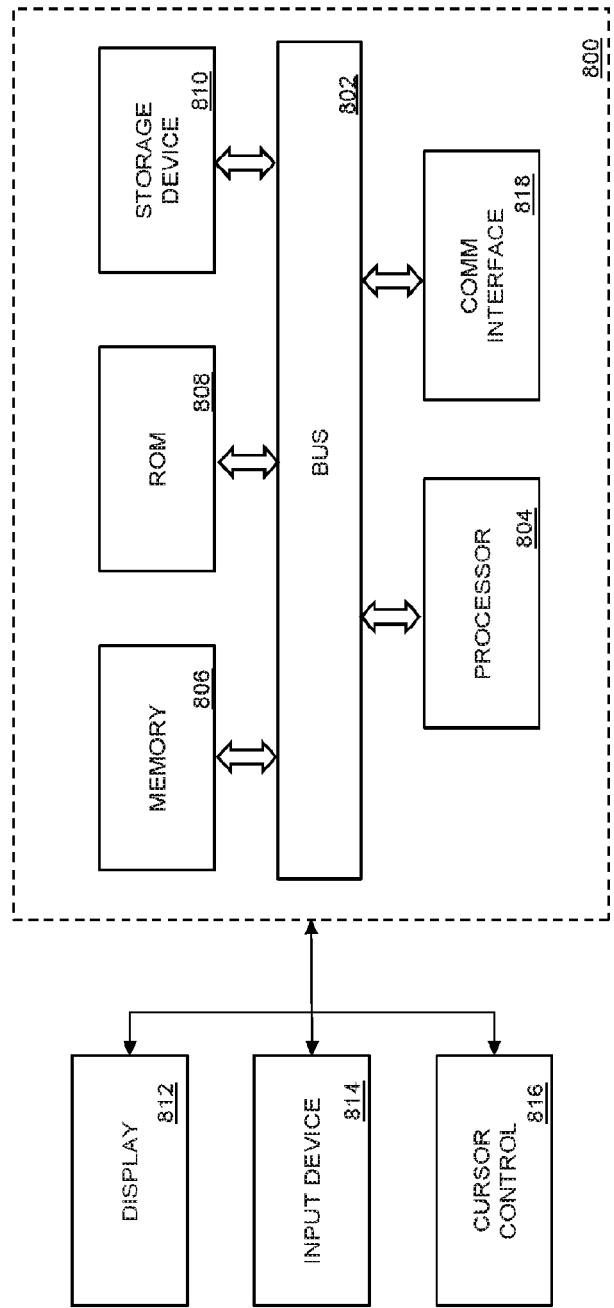
FIG. 8 is a schematic representation of a computing system configured for use in the methods and systems.

FIG. 8 is a block diagram that illustrates a computing system 800 that may be employed to carry out processing functionality, according to various embodiments, upon which embodiments of a fluorescence detector may utilize. Computing system 800 can include one or more processors, such as a processor 804. Processor 804 can be implemented using a general or special purpose processing engine such as, for example, a microprocessor, controller or other control logic. In this example, processor 804 is connected to a bus 802 or other communication medium.

Further, it should be appreciated that a computing system 800 of FIG. 8 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 800 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 800 may include bus 802 or other communication mechanism for communicating information, and processor 804 coupled with bus 802 for processing information.

Computing system 800 also includes a memory 806, which can be a random access memory (RAM) or other dynamic memory, coupled to bus 802 for storing instructions to be executed by processor 804. Memory 806 also may be used for storing temporary variables or other intermediate information during execution of instructions to be executed by processor 804. Computing system 800 further includes a read only memory (ROM) 808 or other static storage device coupled to bus 802 for storing static information and instructions for processor 804.

Computing system 800 may also include a storage device 810, such as a magnetic disk, optical disk, or solid state drive (SSD) is provided and coupled to bus 802 for storing information and instructions. Storage device 810 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored there in particular computer software, instructions, or data.

In alternative embodiments, storage device 810 may include other similar instrumentalities for allowing computer programs or other instructions or data to be loaded into computing system 800. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 810 to computing system 800.

Computing system 800 can also include a communications interface 818. Communications interface 818 can be used to allow software and data to be transferred between computing system 800 and external devices. Examples of communications interface 818 can include a modem, a network interface (such as an Ethernet or other NIC card), a communications port (such as for example, a USB port, a RS-232C serial port), a PCMCIA slot and card, Bluetooth, etc.

Computing system 800 may be coupled via bus 802 to a display 812, such as a cathode ray tube (CRT) or liquid crystal display (LCD), for displaying information to a computer user. An input device 814, including alphanumeric and other keys, is coupled to bus 802 for communicating information and command selections to processor 804, for example. An input device may also be a display, such as an LCD display, configured with touchscreen input capabilities. Another type of user input device is cursor control 816, such as a mouse, a trackball or cursor direction keys for communicating direction information and command selections to processor 804 and for controlling cursor movement on display 812. This input device typically has two degrees of freedom in two axes, a first axis (e.g., x) and a second axis (e.g., y), that allows the device to specify positions in a plane. A computing system 800 provides data processing and provides a level of confidence for such data. Consistent with certain implementations of embodiments of the present teachings, data processing and confidence values are provided by computing system 800 in response to processor 804 executing one or more sequences of one or more instructions contained in memory 806. Such instructions may be read into memory 806 from another computer-readable medium, such as storage device 810. Execution of the sequences of instructions contained in memory 806 causes processor 804 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 804 for execution. Such instructions, generally referred to as "computer program code" (which may be grouped in the form of computer programs or other groupings), when executed, enable the computing system 800 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 810. Volatile media includes dynamic memory, such as memory 806. Transmission media includes coaxial cables, copper wire, and fiber optics, including the wires that comprise bus 802.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 804 for execution. For example, the instructions may initially be carried on magnetic disk of a remote computer. The remote computer can load the instructions into its dynamic memory and send the instructions over a telephone line using a modem. A modem local to computing system 800 can receive the data on the telephone line and use an infra-red transmitter to convert the data to an infra-red signal. An infra-red detector coupled to bus 802 can receive the data carried in the infra-red signal and place the data on bus 802. Bus 802 carries the data to memory 806, from which processor 804 retrieves and executes the instructions. The instructions received by memory 806 may optionally be stored on storage device 810 either before or after execution by processor 804.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Further, according to various embodiments described herein, a fluorescence detector may communicate with a computing system over a network.

Figure 9:
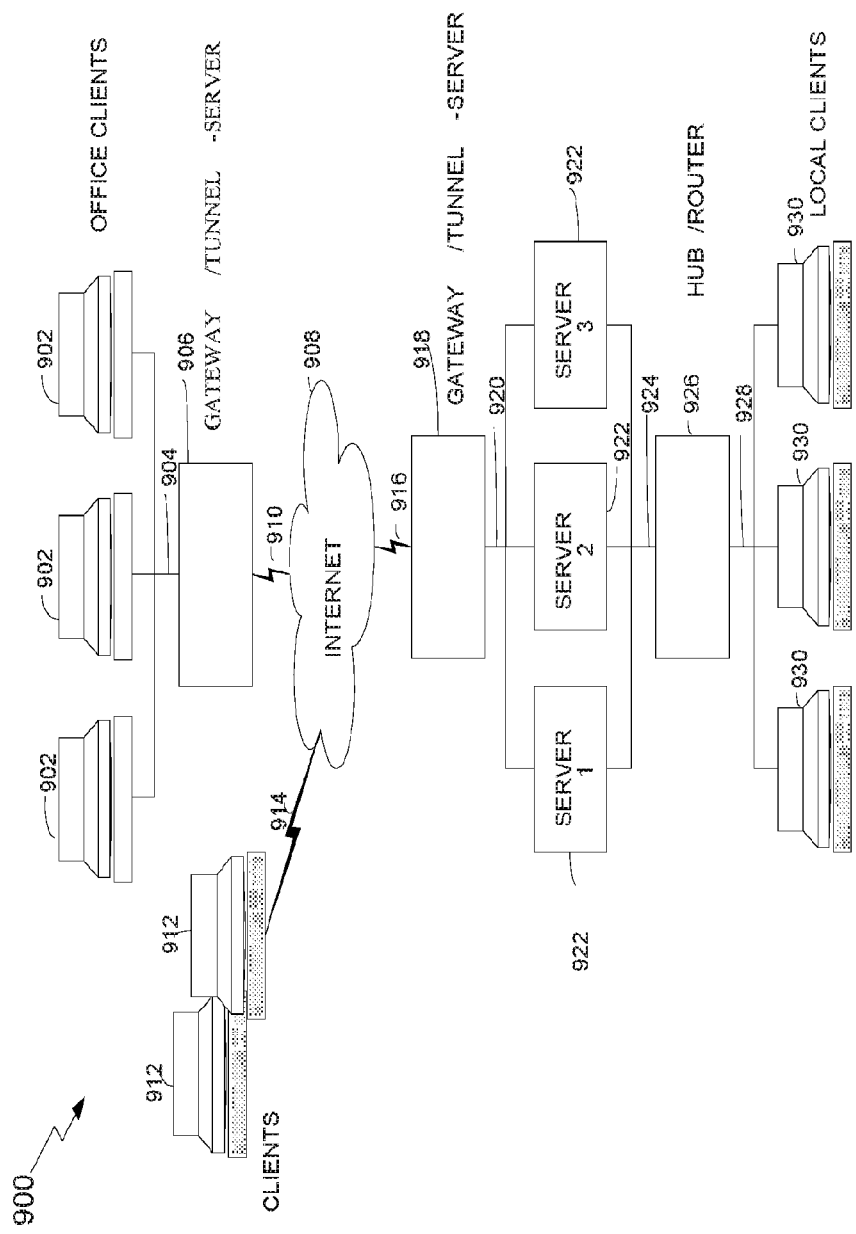
FIG. 9 is a schematic representation of a typical Internet network configuration configured for use in the methods and systems.

Some of the elements of a typical Internet network configuration 900 are shown in FIG. 9, wherein a number of client machines 902 possibly in a remote local office, are shown connected to a gateway/hub/tunnel-server/etc. 910 which is itself connected to the internet 908 via some internet service provider (ISP) connection 910. Also shown are other possible clients 912 similarly connected to the internet 908 via an ISP connection 914, with these units communicating to possibly a central lab or office, for example, via an ISP connection 916 to a gateway/tunnel-server 918 which is connected 920 to various enterprise application servers 922 which could be connected through another hub/router 926 to various local clients 930. Any of these servers 922 could function as a development server for the analysis of potential content management and delivery design solutions as described in the present invention, as more fully described below.

Figure 10:
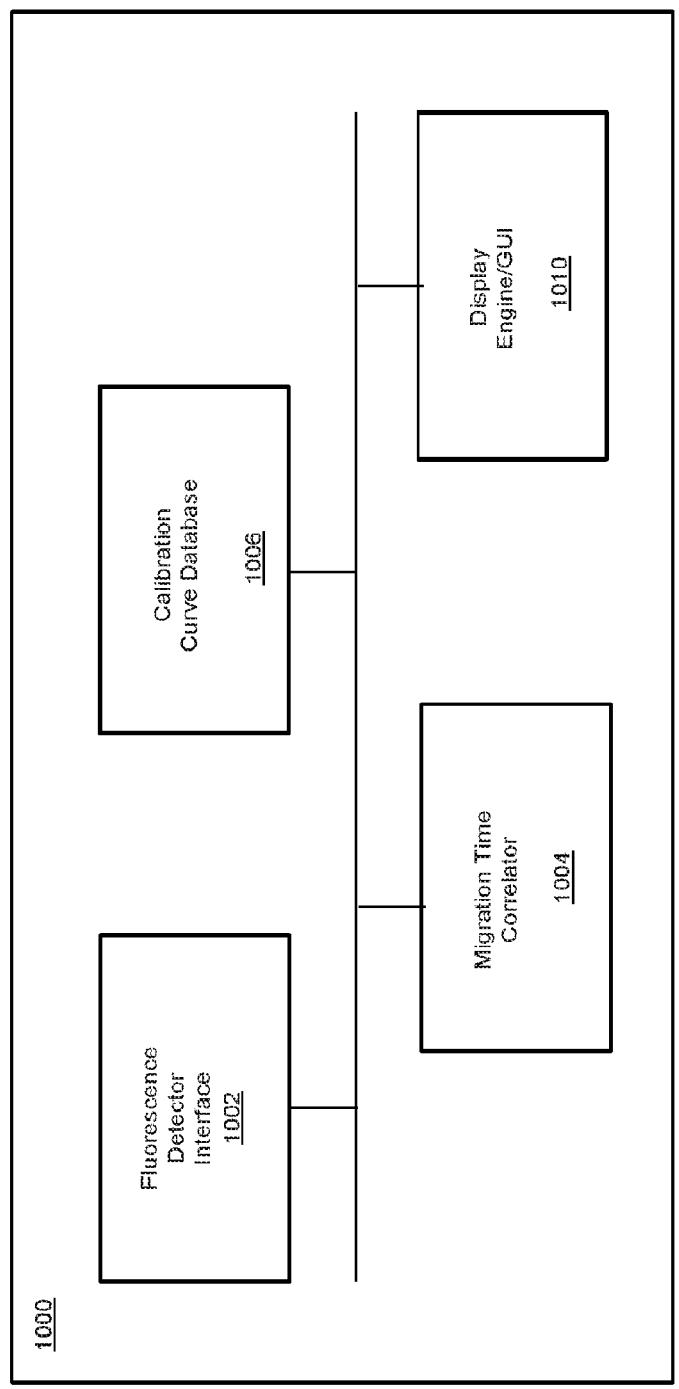
FIG. 10 is a block diagram illustrating a system for generating a calibration curve according to various embodiments described herein.
Figure 11:
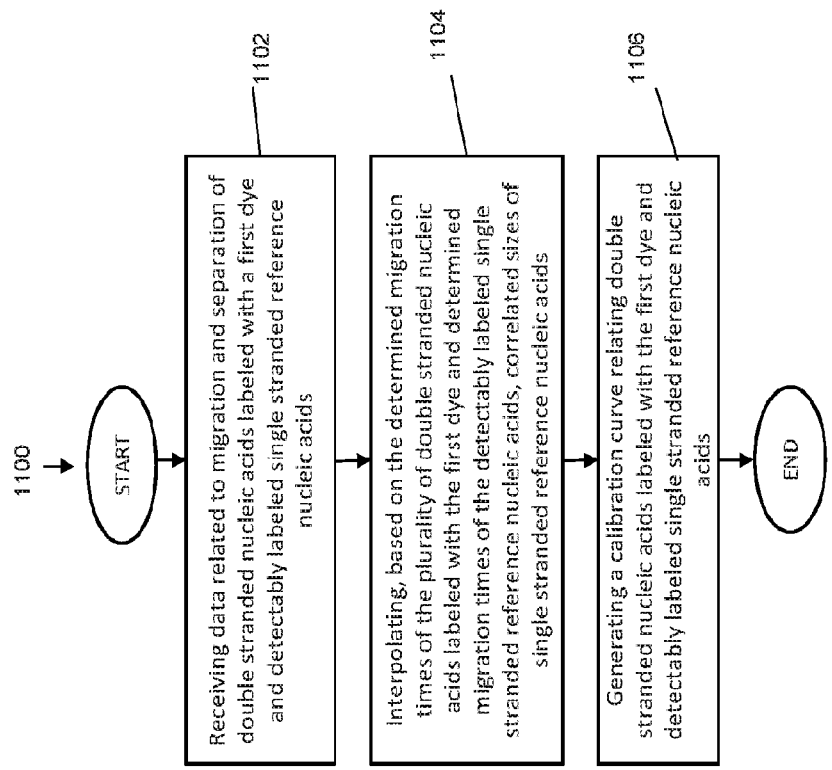
FIG. 11 is a flow diagram illustrating a method for generating a calibration curve according to various embodiments described herein.

Methods and systems for determining a size of a double stranded nucleic acid sample are shown and described in FIGS. 10 and 11.

FIG. 10 is a block diagram illustrating a system 1000 for generating a calibration curve according to various embodiments described herein. System 1000 includes a fluorescence detector interface 1002, a migration time correlator 104, a calibration curve database 1006, and a display 1010. Fluorescence detector interface 1002 is configured to receive data related to:

1) Migrating a plurality of double stranded nucleic acids labeled with a first dye under mobility dependent separation conditions. The size of each of the double stranded nucleic acids is known.
2) Migrating a plurality of detectably labeled single stranded reference nucleic acids under the mobility dependent separation conditions. The size of each of the detectably labeled single stranded reference nucleic acids is known.
3) Separating each of the plurality of double stranded nucleic acids labeled with the first dye and determining a migration time of each of the plurality of double stranded nucleic acids labeled with the first dye.
4) Separating each of the detectably labeled single stranded reference nucleic acids and determining a migration time of each of the detectably labeled single stranded reference nucleic acids.

Migration time correlator 1004 is configured to interpolate, based on the determined migration times of the plurality of double stranded nucleic acids labeled with the first dye and determined migration times of the detectably labeled single stranded reference nucleic acids, correlated sizes of single stranded reference nucleic acids. Migration time correlator 1004 is further configured to generate a calibration curve relating double stranded nucleic acids labeled with the first dye and detectably labeled single stranded reference nucleic acids.

Calibration curve database 1006 is configured to store the calibration curve.

Display 1010 is configured to display the calibration curve to a user.

FIG. 11 is a flow diagram illustrating a method for generating a calibration curve according to various embodiments described herein. The method may be implemented by exemplary computing system shown in FIG. 8. The method includes, in step 1102, receiving data, by a processor, related to:

1) Migrating a plurality of double stranded nucleic acids labeled with a first dye under mobility dependent separation conditions. The size of each of the double stranded nucleic acids is known.
2) Migrating a plurality of detectably labeled single stranded reference nucleic acids under the mobility dependent separation conditions. The size of each of the detectably labeled single stranded reference nucleic acids is known.
3) Separating each of the plurality of double stranded nucleic acids labeled with the first dye and determining a migration time of each of the plurality of double stranded nucleic acids labeled with the first dye.
4) Separating each of the detectably labeled single stranded reference nucleic acids and determining a migration time of each of the detectably labeled single stranded reference nucleic acids.

The method further includes step 1104 of interpolating, by the processor, based on the determined migration times of the plurality of double stranded nucleic acids labeled with the first dye and determined migration times of the detectably labeled single stranded reference nucleic acids, correlated sizes of single stranded reference nucleic acids.

In step 1106, a calibration curve is generated, by the processor, relating double stranded nucleic acids labeled with the first dye and detectably labeled single stranded reference nucleic acids.

Method 1100 may also be stored on a computer-readable storage medium in the form of processor-executable instructions.

Figure 12:
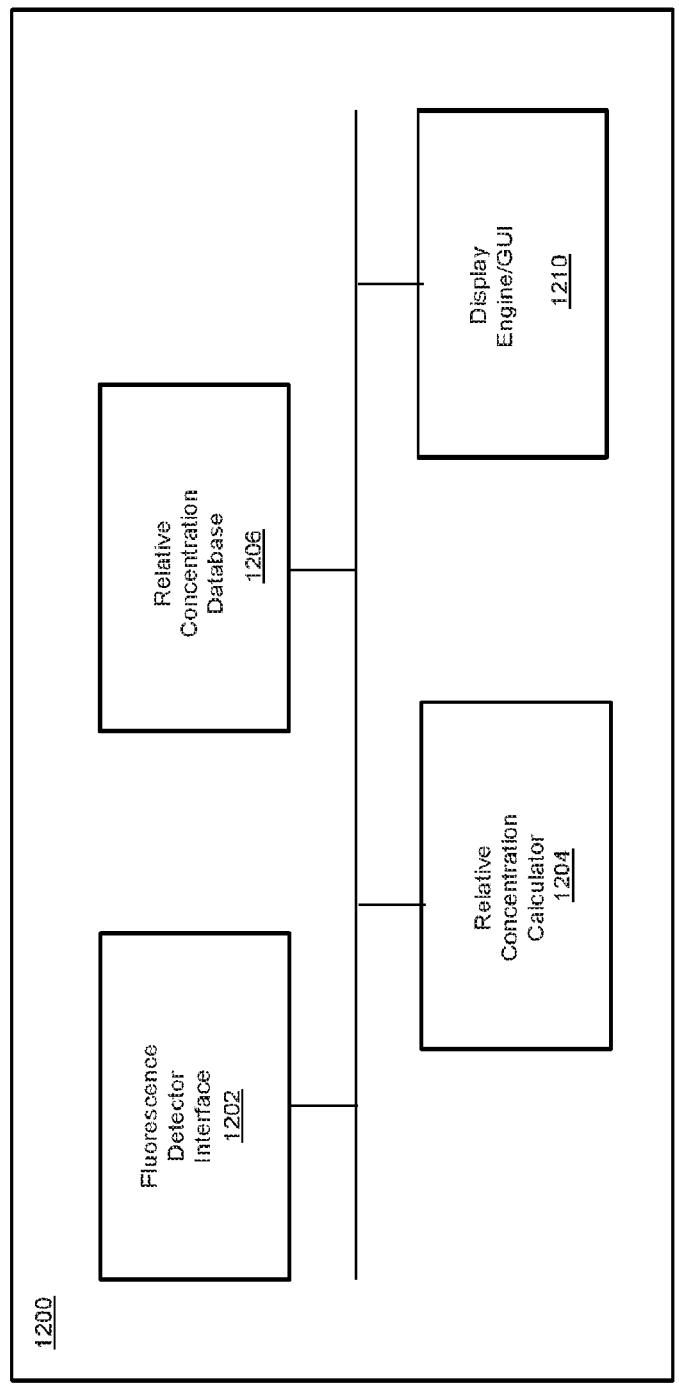
FIG. 12 is a block diagram illustrating a system for determining relative sample concentration according to various embodiments described herein.
Figure 13:
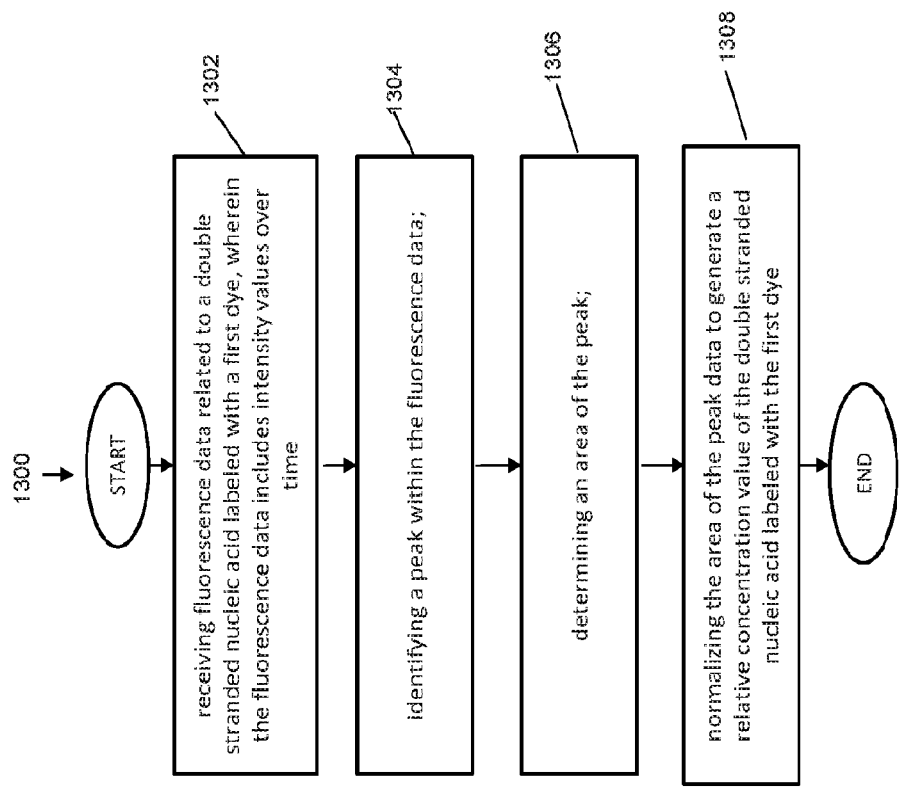
FIG. 13 is a flow diagram illustrating a method for determining relative sample concentration according to various embodiments described herein.

Methods and systems for quantifying a double stranded nucleic acid are described and shown in FIGS. 12 and 13.

FIG. 12 is a block diagram illustrating a system 1200 for determining relative sample concentration according to various embodiments described herein. System 1200 includes fluorescence detector interface 1202, relative concentration calculator 1204, relative concentration database 1206, and display 1210.

Fluorescence detector interface 1202 is configured to receive fluorescence data related to a double stranded nucleic acid labeled with a first dye. The fluorescence data includes intensity values over time.

Relative concentration calculator 1204 is configured to identify a peak within the fluorescence data, determine an area of the peak, and normalize the area of the peak data to generate a relative concentration value of the double stranded nucleic acid labeled with the first dye.

Relative concentration database 1206 is configured to store the relative concentration value.

Display 1210 is configured to display the relative concentration value to the user.

FIG. 13 is a flow diagram illustrating a method 1300 for determining relative sample concentration according to various embodiments described herein. Method 1300 includes step 1302 of receiving fluorescence data related to a double stranded nucleic acid labeled with a first dye, wherein the fluorescence data includes intensity values over time. In step 1304, a peak within the fluorescence data is identified. In step 1306 an area of the peak is determined. In step 1308, the area of the peak data is normalized to generate a relative concentration value of the double stranded nucleic acid labeled with the first dye.

Additional analytical components.

The system may be connected to additional components to provide a second analytical measurement, differing from the electrophoretic separation described above. The second analytical measurement may be selected from mass spectrometry, UV absorbance, Hydrophilic Liquid Chromatography, nuclear magnetic resonance, or other analysis methods offering differing or orthogonal analysis modes. The second analytical measurement could include a second electrophoretic separation under differing buffer or electric field conditions, such that differing migration forces may effect a different migration behavior of the mixture. The output of the first electrophoretic separation may be connected operably with the input of the second analytical instrument or selected aliquots of separated nucleic acids produced from the first electrophoretic separation may be transferred manually to the second analytical instrumentation.

EXAMPLES

Example 1. DNA/NGS Library QC/Sizing on a CE System

Prepared non-covalently labeled amplicons of various sizes and the *E. coli* DH10B 200 and 400-bp ION PGM control libraries are used to demonstrate the ability to 1) distinguish between a size selected ready to run NGS library and a potential impurity such as a spiked in amplicon, 2) estimate the size of an "unknown" impurity (double stranded (ds)-DNA amplicon) and ds-DNA distribution of NGS 200 and 400-bp libraries 3) demonstrate the use of a single strand (ss)-covalently labeled size standard which remains virtually unaffected by the ds-labeling dye when present within the same capillary under the separation conditions.

Materials

AmpliTaq Gold® 360 PCR Mix (Applied Biosystems® PN 4398881, ThermoFisher Scientific); ExoSAP-IT® (Affymetrix, Inc. PN 78201 1 ML); DNA Buffer (10 mM Tris/0.1 mM EDTA, pH 8.0) (Teknova PN T0223); Ultra-Pure™ DNase/RNase-Free Distilled Water (Applied Biosystems® PN 10977-015, ThermoFisher Scientific); Micro-Amp™ Clear Adhesive Film (Applied Biosystems® PN 4306311, ThermoFisher Scientific); MicroAmp® Optical 96-Well Reaction Plate (Applied Biosystems® PN N8010560, ThermoFisher Scientific); YOYO-1 IODIDE (491/509, 1-mM 200-ul) (Molecular Probes PN Y3601, ThermoFisher Scientific); DMSO, Anhydrous (Molecular Probes PN D12345, ThermoFisher Scientific); Genescan®-1200 LIZ® Size Standard Kit (Applied Biosystems® PN 4379950, ThermoFisher Scientific); Ion PGM® Controls Kit V2 (Ion Torrent® PN 4482010, ThermoFisher Scientific); Applied Biosystems® Genetic Analyzer 3730xl (50 cm/96-cap array) and 3500xl (50 cm/24-cap array), ThermoFisher Scientific); Applied Biosystems® POP7® electrophoresis separation medium, ThermoFisher Scientific) and PCR primers for Amplicon generation as shown in Table 2. (ThermoFisher Scientific).

TABLE 2

| PCR Primer Name: ZA (~634-bp amplicon w/M13 tails) | |
|---|---|
| Fwd-primer (*M13 in italics*) | *TGTAAAACGACGGCCAGT*GCCCTGGAAGGAGAACAAA GGC (SEQ ID NO: 1) |
| Rev-primer (*M13 in italics*) | *CAGGAAACAGCTATGACC*TGACCCGAGATGGTGCTTGA (SEQ ID NO: 2) |
| PCR Primer Name: Seq01 (~545-bp amplicon w/M13 tails) | |
| Fwd-primer (*M13 in italics*) | *TGTAAAACGACGGCCAGT*GCTGCCTCTGATGGCGGAC (SEQ ID NO: 3) |
| Rev-primer (*M13 in italics*) | *CAGGAAACAGCTATGACC*GCCACACTCTGGAGCTGGACA (SEQ ID NO: 4) |

TABLE 2-continued

| PCR Primer Name: 11.697 (~197-bp amplicon w/M13 tails) | |
|---|---|
| Fwd-primer (*M13 in italics*) | *TGTAAAACGACGGCCAGT*CCAACCCTTGTCCTTACCAG AACG (SEQ ID NO: 5) |
| Rev-primer (*M13 in italics*) | *CAGGAAACAGCTATGACC*AAACTGTGAGTGGATCCAT TGGAA (SEQ ID NO: 6) |
| PCR Primer Name: 12.839 (~172-bp amplicon w/M13 tails) | |
| Fwd-primer (*M13 in italics*) | *TGTAAAACGACGGCCAGT*TTCCCACAGGTCTCTGCTAG GG (SEQ ID NO: 7) |
| Rev-primer (*M13 in italics*) | *CAGGAAACAGCTATGACC*CAGTCAGATCCTAGCGTCGAG (SEQ ID NO: 8) |

Amplicon Generation.

For the Polymerase Chain Reaction (PCR) amplification reaction to produce the amplicons, 1 ul of DNA Template sample (in this case, Ion PGM® Controls Kit V2), 2 ul of PCR Primer (1.2 um/ea), 5 ul of AmpliTaq Gold® 360 PCR Mix, 0.5-ul (5%) GC Enhancer (part of the AmpliTaq Gold® 360 PCR kit, and 1.5 ul of distilled water (RNase/DNase free) are combined to form a 10 ul reaction volume. The reaction volume is subjected to the cycling conditions shown below in Table 3. The product of the PCR reaction is treated with the steps as shown in Table 4, to provide a mixture of amplicons used as the plurality of double stranded nucleic acids.

TABLE 3

AmpliTaq Gold ® 360 PCR Cycling Conditions

| | Cycle | Temperature | Time |
|---|---|---|---|
| 1x Denaturation | Denaturation | 95° C. | 10-min. |
| 35x Elongation | 96° C. Annealing* 72° C. | 30-sec. 58° C. 45-sec. | 30-sec. |
| 1x | Final Elongation | 72° C. | 7-min. |
| 1x | Hold | 4° C. | Hold |

TABLE 4

PCR Product Clean-up/ExoSAP-IT Treatment (4-ul ExoSapit/10ul PCR product)

| | Cycle | Temperature | Time |
|---|---|---|---|
| 1x | Digest | 37° C. | 15-min. |
| 1x | Heat deactivation | 80° C. | 15-min. |
| 1x | Hold | 4° C. | Hold |

Sample Labeling.

A 10 uM stock solution of YOYO-1 is made from the commercial supply in DMSO, by adding 10-ul of YOYO-1: to 990-ul of Anhydrous DMSO. The solution is stored at −20° C. A working labeling solution is made fresh daily by adding 4 ul of the 10 uM YOYO-1 stock to 796 ul of ultra pure distilled water to provide a 50 nM (1:20,000×) YOYO-1 labeling solution.

To label double stranded nucleic acid, add 8 ul of 50 nM YOYO-1 solution to 1 ul of Genescan®-1200 LIZ® Size Standard and mix well. Addition is made with 1 ul of NGS library (including spiked amplicon, if present) to produce a 10 ul mixture per well. The well is sealed with adhesive film during the incubation period to decrease evaporation. The reaction mixture is incubated according to the cycles in Table 5. The adhesive film is removed after the labeling cycles are complete and septa are added in preparation for electrophoretic separation.

TABLE 5

Incubation cycles for labeling reaction.

| | | Temperature | Time |
|---|---|---|---|
| 1x | Incubate | 37° C. | 10-min. |
| 1x | Hold | 4° C. | Hold |

Electrophoretic Separation.

Due to potential joule heating during electrophoresis the preliminary run conditions vary slightly between the 3500 and 3730 CE instruments.

3500 Run Parameters:

Polymer is POP7®. Run Module is LongFragmentAnalysis50-POP7xl. Oven temp. 40° C. Run voltage 8.5 kVolts. Prerun voltage 15 kVolts. Injection voltage 1.6 kVolts. Run time 6600 sec. Prerun time 180 sec. Injection time 15 sec. Data delay is 240 sec.

3730 Run Parameters:

Polymer is POP7®. Oven temp. 35° C. Buffer temperature 35° C. Prerun voltage 15 kVolts. Prerun time 180 sec. Injection voltage 2.0 kVolts. Injection time 15 sec. First Readout Time 200 msec. Second Readout Time 200 msec. Run Voltage 8.5 kVolts. Voltage number of steps 40. Voltage Step Interval 15 sec. Voltage Tolerance 0.6 kVolts. Current Stability30uA. Ramp Delay 1 sec. Data Delay 360 sec. Run Time 6600 sec.

Results.

Figure 14:
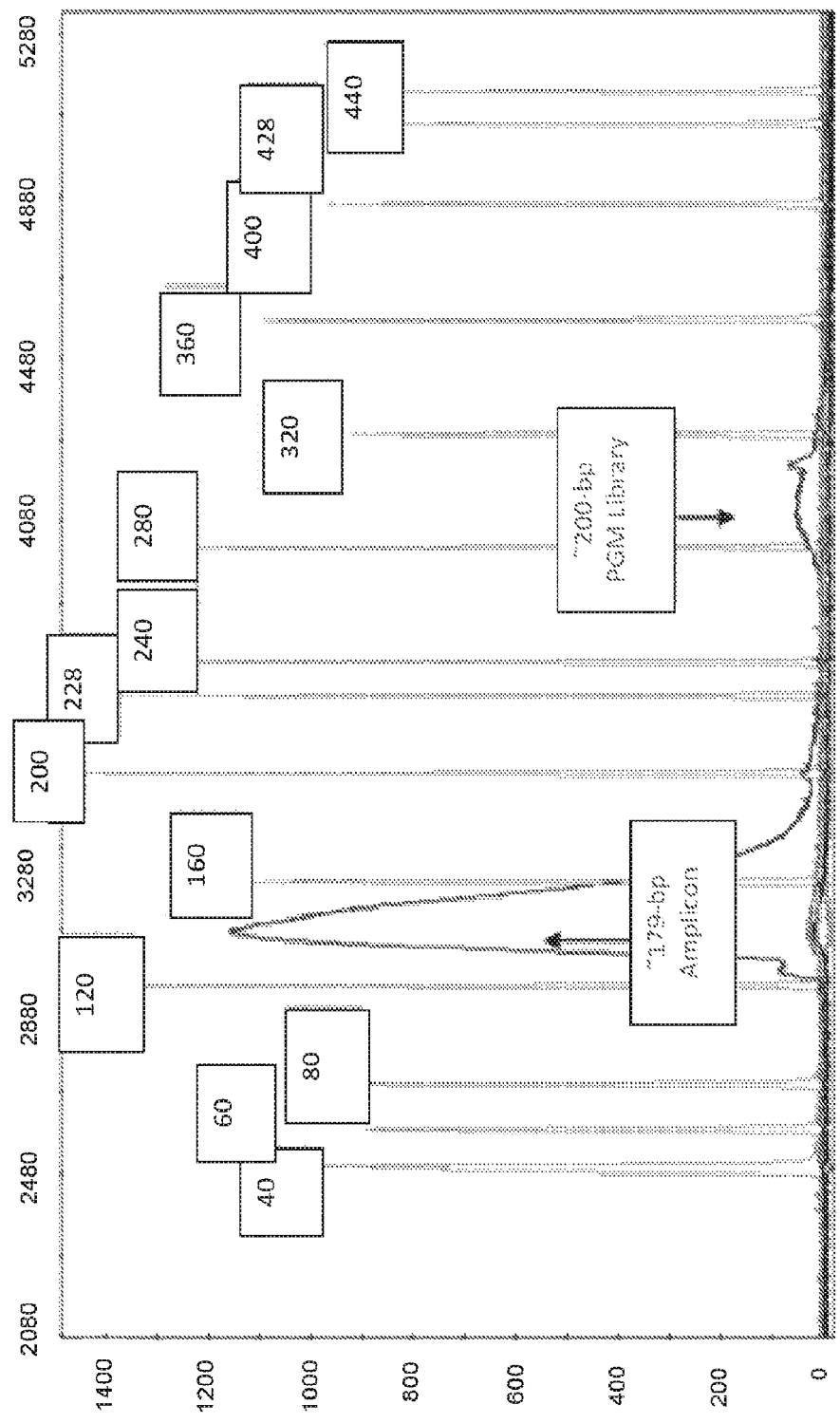
FIG. 14 is a graphical representation of an electropherogram of an approximately 179 bp double stranded amplicon and a library of double stranded nucleic acids designed to have about 200 bp size, each of which is labeled with a first dye, and a single stranded sizing ladder detectably labeled with a spectrally resolvable second dye, having a range of bp up to 1200.

FIG. 14: 200-bp Library Spiked with 179-bp Amplicon.

In this experiment a 200-bp library (DH10B, Ion PGM®) is spiked with an approximately 179 bp double stranded single amplicon. For the purposes of this experiment the single stranded 1200 bp size standard covalently labeled with LIZ® dye is assigned an estimated ds-DNA size value roughly 2x the ss-DNA size; this value can be calibrated against a double stranded size standard covalently labeled with ROX™ dye to provide a more accurate estimate of actual size. FIG. 14 demonstrates that both a ~179-bp amplicon "impurity" as well as a 200-bp PGM control library can be labeled, detected and distinguished from one another when run on a Genetic Analyzer CE 3500 instrument using POP7® polymer and a 50 CM array. With the adapters (~71-bp) ligated to the 200-bp library, the resultant double stranded nucleic acid library is projected to be distributed around 300-bp, which is confirmed in the electropherogram as shown. The LIZ-1200 size standard (sharp peaks with individual size labels) can be potentially optimized and used to size both the "impurity" (the amplicon in this case) as well as the PGM 200-bp library in an automated fashion and relative amounts of each determined by using ratios calculated using areas beneath each curve. The double stranded amplicon and library may demonstrate broadened peaks due to incomplete labeling with YOYO-1 or due to differential loss of some YOYO-1 labeling. YOYO-1 labels tend to intercalate roughly every 5 nucleotides along a double stranded nucleic acid. Under these at least partially denaturing conditions, some loss of YOYO-1 labels may be occurring. However, both the single amplicon spike as well as the double stranded nucleic acid library is shown to be correctly sized by this electrophoretic method.

Figure 15:
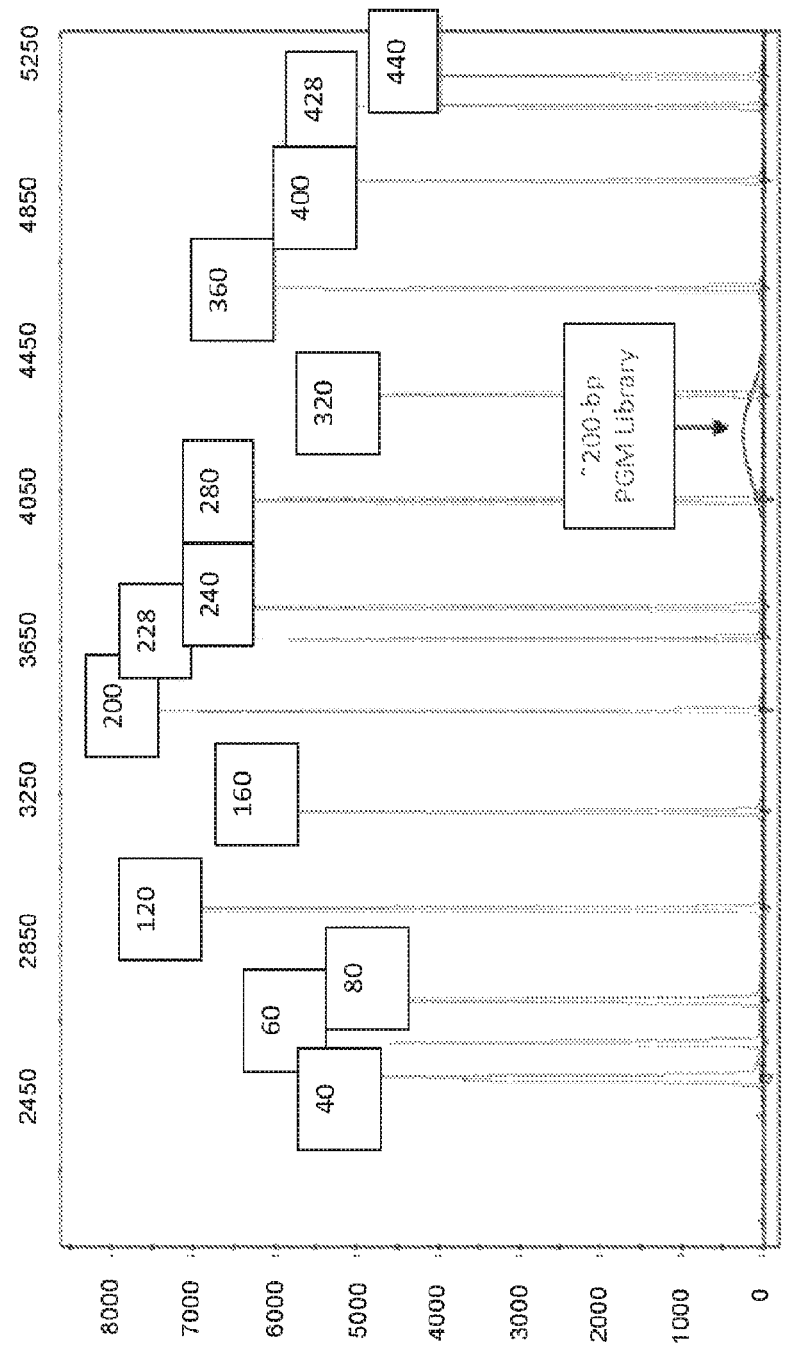
FIG. 15 is a graphical representation of an electropherogram of a library of double stranded nucleic acids designed to have about 200 bp size, each of which is labeled with a first dye, and a single stranded sizing ladder detectably labeled with a spectrally resolvable second dye, having a range of bp up to 1200.

FIG. 15: 200-bp Library Alone.

In this experiment the labeled 200-bp library (DH10B, Ion PGM®) is separated with the single stranded 1200 bp size standard covalently labeled with LIZ® dye. Sizes for the size standard are assigned an estimated ds-DNA size value as discussed above for FIG. 14. FIG. 15 demonstrates even size standard fragment distribution and sizing in an expected range: with the adapters (~71-bp) ligated the 200-bp library is expected to be distributed around 300-bp when run on a Genetic Analyzer CE 3500 instrument using POP7® polymer and a 50 cm array, which is confirmed in the electropherogram as shown.

Figure 16:
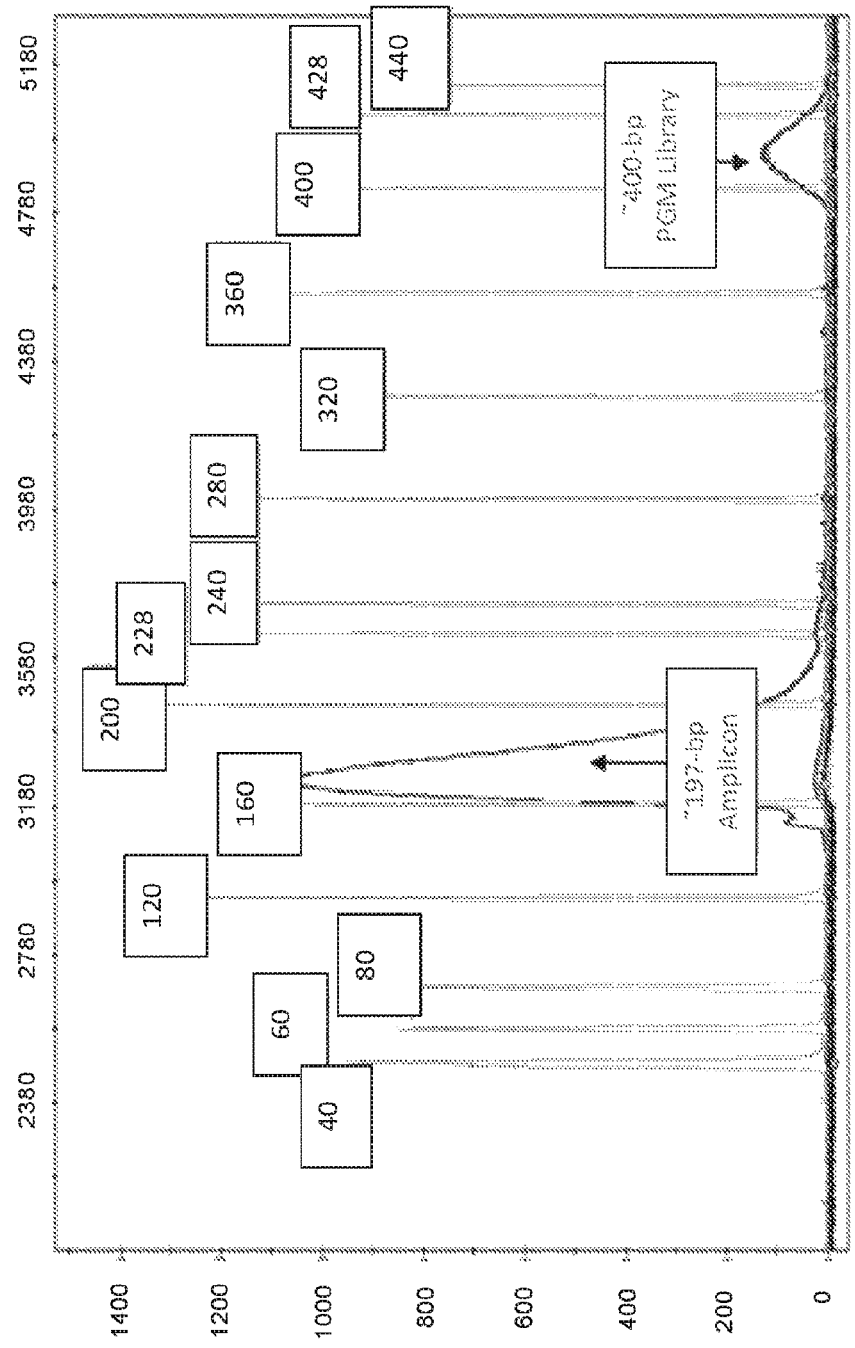
FIG. 16 is a graphical representation of an electropherogram of an approximately 197 bp double stranded amplicon and a library of double stranded nucleic acids designed to have about 400 bp size, each of which is labeled with a first dye, and a single stranded sizing ladder detectably labeled with a spectrally resolvable second dye, having a range of bp up to 1200.

FIG. 16: 400-bp Library Spiked with 197-bp Amplicon.

This experiment demonstrates that both a ~197-bp amplicon "impurity" spike as well as a 400-bp (DH10B PGM) control library can be labeled, detected and distinguished from one another when run on a Genetic Analyzer CE 3500 instrument using POP7® polymer and a 50 cm array. Note that compared to FIG. 14 the 197-bp amplicon fragment migrates slightly later compared to the 179-bp amplicon of the experiment of FIG. 14, indicating reproducibility of migration in the electrophoretic separation. Therefore, amplicons relatively similar in size may be distinguished. The 400-bp PGM Control library migrates to an expected position nearly 2x larger than the 197-bp amplicon on the 3500 POP7/50 cm system.

Figure 17:
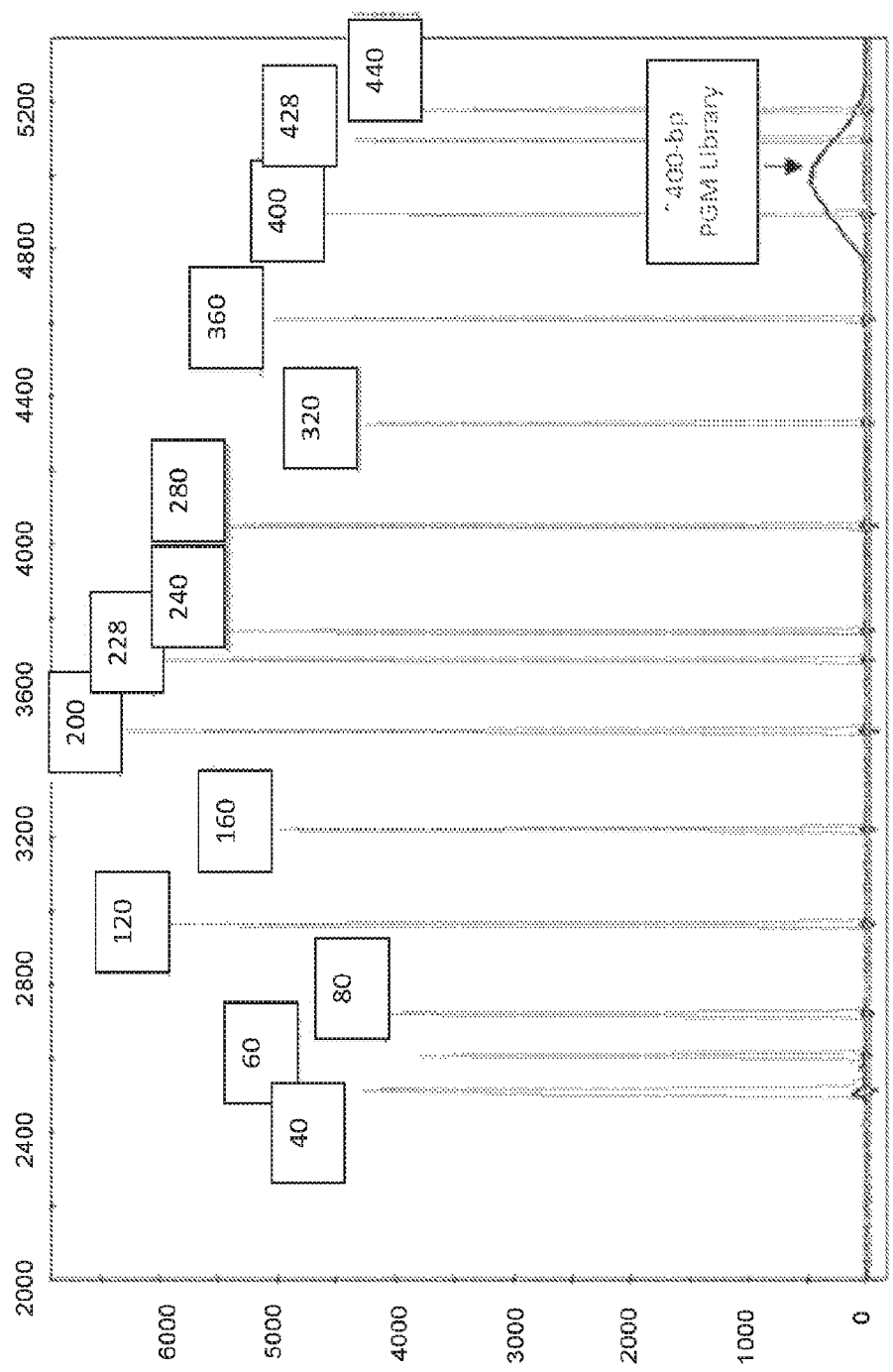
FIG. 17 is a graphical representation of an electropherogram of a library of double stranded nucleic acids designed to have about 400 bp size, each of which is labeled with a first dye, and a single stranded sizing ladder detectably labeled with a spectrally resolvable second dye, having a range of bp up to 1200.

FIG. 17. 400-bp Library Alone.

This experiment demonstrates that the 400-bp (DH10B PGM) control library can be labeled, detected and distinguished from a 200 bp library when run on a Genetic Analyzer CE 3500 instrument using POP7® polymer and a 50 cm array. Even fragment distribution and sizing in an expected range is shown.

Figure 18:
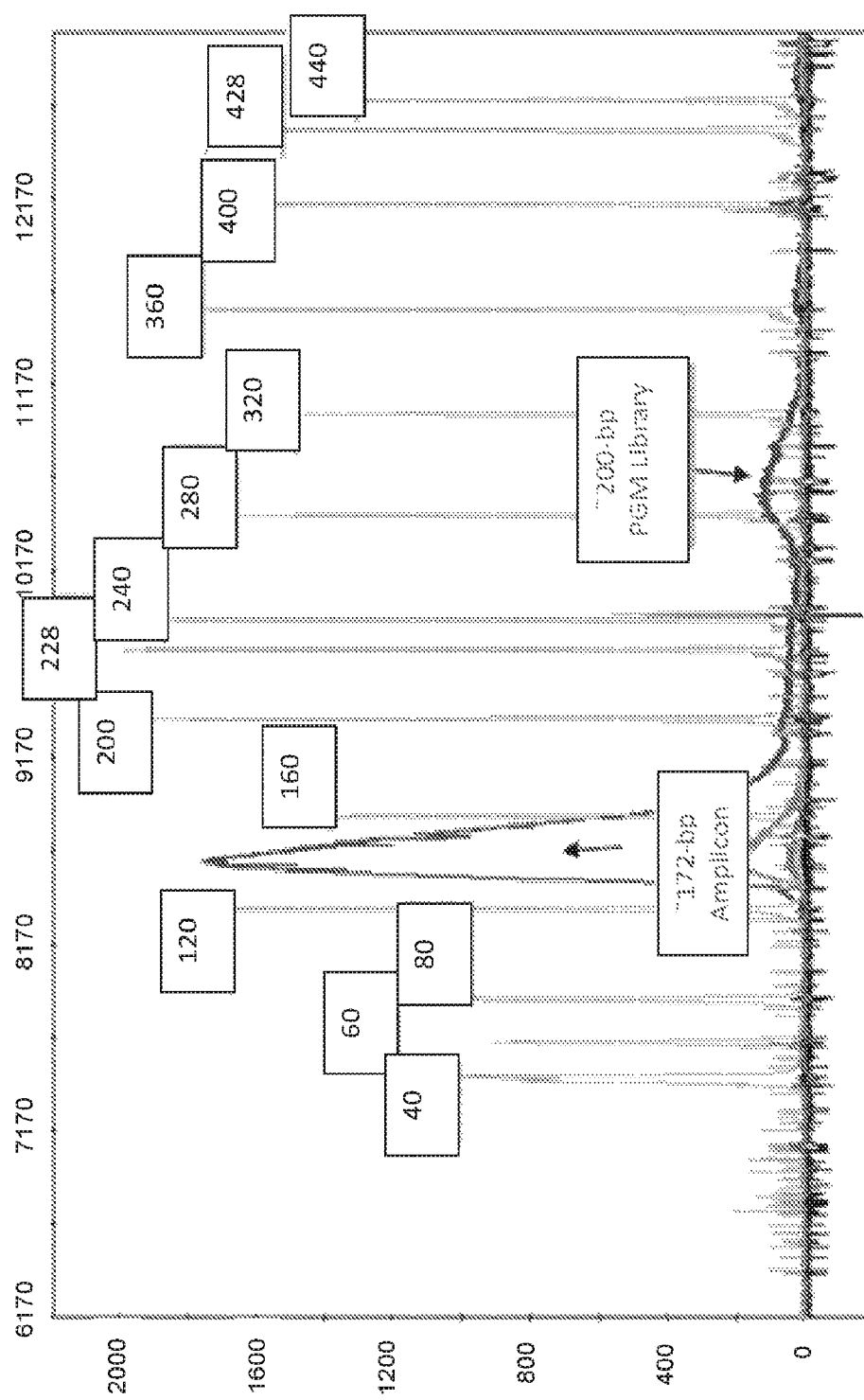
FIG. 18 is a graphical representation of an electropherogram of an approximately 172 bp double stranded amplicon and a library of double stranded nucleic acids designed to have about 200 bp size, each of which is labeled with a first dye, and a single stranded sizing ladder detectably labeled with a spectrally resolvable second dye, having a range of bp up to 1200.

FIG. 18: 200-bp Library Spiked with 172-bp Amplicon.

This experiment demonstrates that it is possible to label, detect and distinguish between an "impurity" peak (172-bp amplicon in this example) spiked into the mixture and a 200-bp library (DH10B PGM control) labeled with 50-nM YOYO-1 when separated in the presence of the 1200 bp single stranded size standard covalently labeled with LIZ® dye on a Genetic Analyzer CE 3730 instrument using POP7® polymer separation medium and a 50-cm array. The LIZ1200 size standard is not labeled with the intercalator and acts as an internal size standard for sizing the ds-DNA. The 3730 baseline noise appears high but is not thought to be related to the chemistry system and appears to be potential electrical interference of some sort or micro-bubbles in the capillary.

Figure 19:
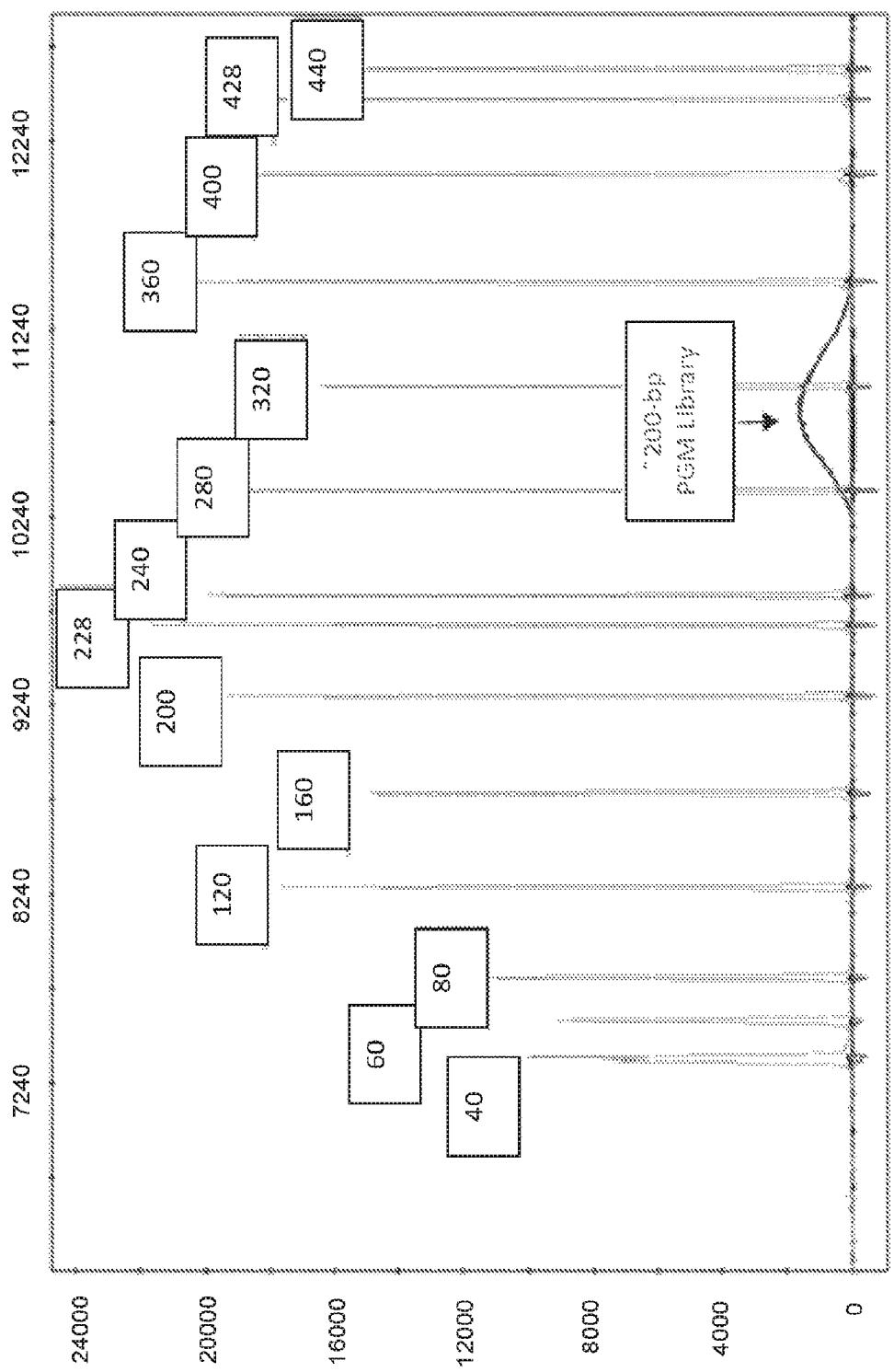
FIG. 19 is a graphical representation of an electropherogram of a library of double stranded nucleic acids designed to have about 200 bp size, each of which is labeled with a first dye, and a single stranded sizing ladder detectably labeled with a spectrally resolvable second dye, having a range of bp up to 1200.

FIG. 19. 200 bp Library Alone.

This experiment demonstrates the ability to detect the 200-bp library (DH10B PGM control) with even fragment distribution and sizing in an expected range, on the on the Genetic Analyzer 3730 CE instrument using POP7® polymer and a 50 cm array. With the adapters (~71-bp) ligated the 200-bp library is projected to be distributed around 300-bp. This is clearly shown in the electropherogram of FIG. 19.

Figure 20:
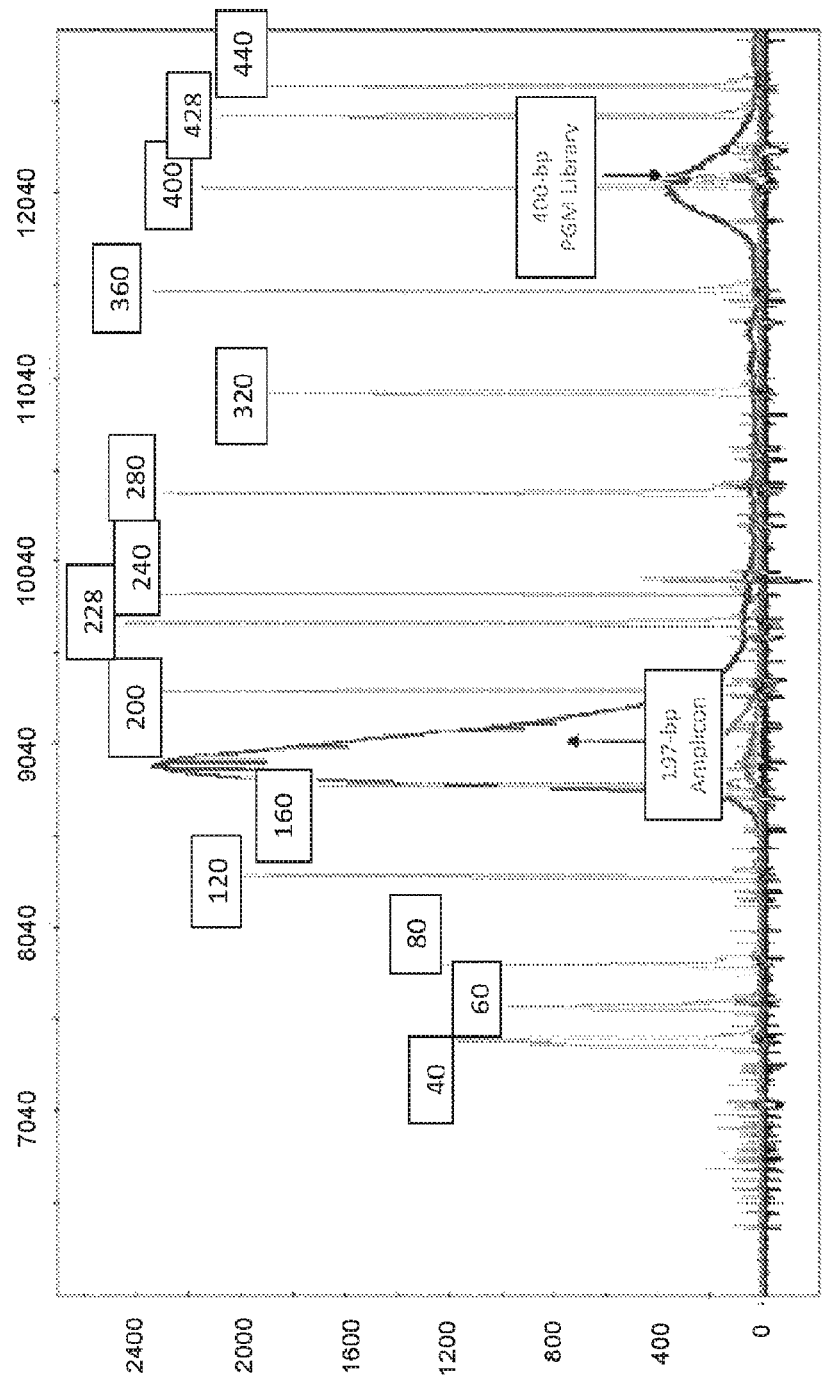
FIG. 20 is a graphical representation of an electropherogram of an approximately 197 bp double stranded amplicon and a library of double stranded nucleic acids designed to have about 400 bp size, each of which is labeled with a first dye, and a single stranded sizing ladder detectably labeled with a spectrally resolvable second dye, having a range of bp up to 1200.

FIG. 20: 400-bp Library Spiked with 197-bp Amplicon.

This experiment demonstrates that both a ~197-bp amplicon "impurity" spike as well as a 400-bp (DH10B PGM) control library labeled with 50-nM YOYO-1 when separated in the presence of the 1200 bp single stranded size standard covalently labeled with LIZ® dye on a Genetic Analyzer CE 3730 instrument using POP7® polymer separation medium and a 50-cm array. The LIZ1200 size standard is not labeled with the intercalator and acts as an internal size standard for sizing the ds-DNA. The 400-bp PGM Control library migrates to an expected position nearly 2× larger than the 197-bp amplicon on the 3730 POP7/50 cm system.

Figure 21:
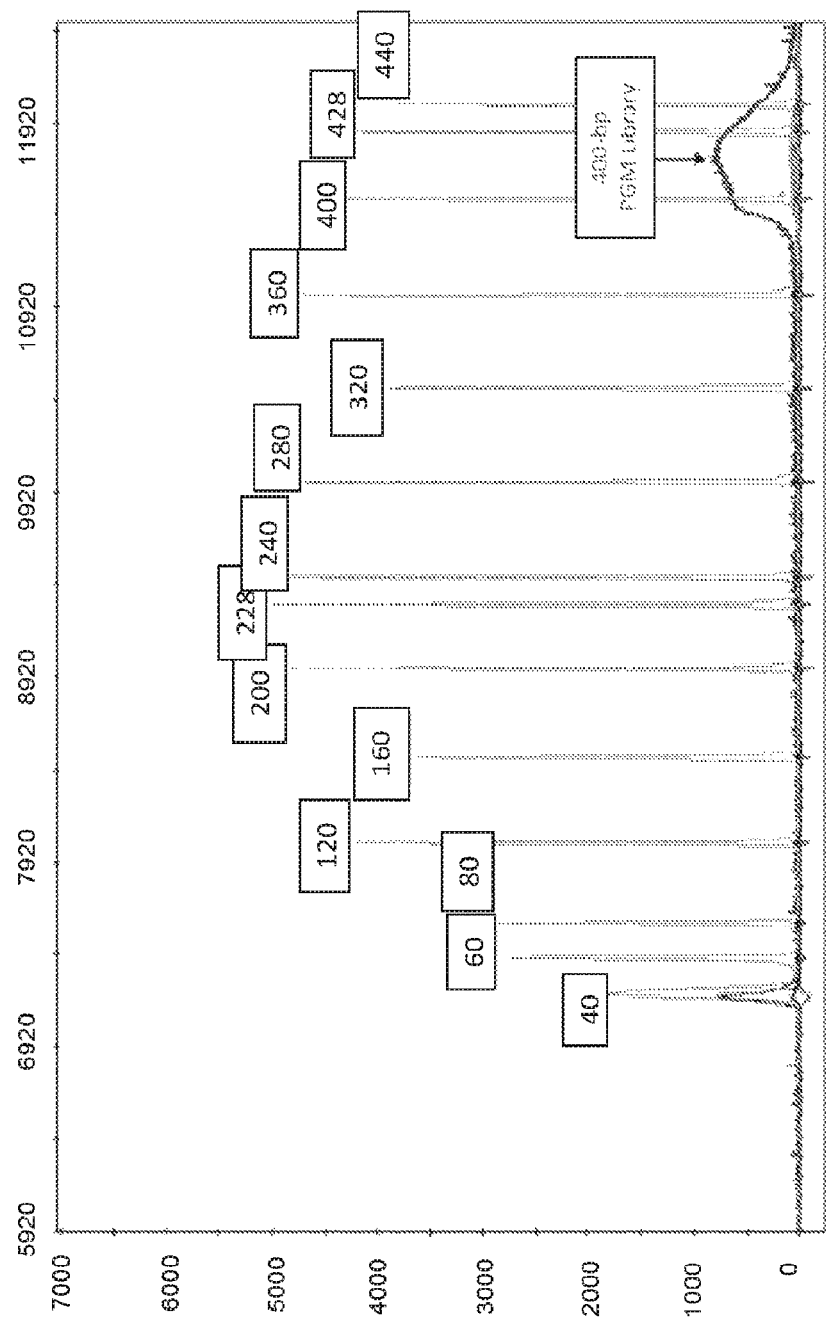
FIG. 21 is a graphical representation of an electropherogram of a library of double stranded nucleic acids designed to have about 400 bp size, each of which is labeled with a first dye, and a single stranded sizing ladder detectably labeled with a spectrally resolvable second dye, having a range of bp up to 1200.

FIG. 21: 400-bp Library Alone.

This experiment demonstrates the ability to detect the 400-bp library (DH10B PGM control) with even fragment distribution and sizing in an expected range, on the on the Genetic Analyzer 3730 CE instrument using POP7® polymer and a 50 cm array. With the adapters (~71-bp) ligated the 200-bp library is projected to be distributed around 300-bp. This is clearly shown in the electropherogram of FIG. 21.

Those skilled in the art understand that the detection techniques employed are generally not limiting. Rather, a wide variety of detection means are within the scope of the disclosed methods and kits, provided that they allow the presence or absence of labeled nucleic acids to be determined. While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed is:

1. A method for determining a range of lengths of a plurality of double stranded nucleic acids; comprising the steps of:
    contacting the plurality of double stranded nucleic acids with a) a first dye, and b) a detectably labeled single stranded sizing ladder, under conditions wherein the first dye is configured to label a double stranded nucleic acid;
    producing a mixture comprising a plurality of first dye-labeled double stranded nucleic acids and the detectably labeled single stranded sizing ladder;
    migrating the mixture under mobility dependent separation conditions;
    separating each of the plurality of first dye-labeled double stranded nucleic acids; and
    determining a migration time of each of the plurality of first dye-labeled double stranded nucleic acids.

2. The method of claim 1, further comprising the step of determining a migration time of each of the plurality of fragments of the detectably labeled single stranded sizing ladder.

3. The method of claim 2, further comprising converting the migration time of each of the plurality of first dye-labeled double stranded nucleic acids to a length.

4. The method of claim 3, wherein the converting step comprises a step of comparing a migration time of the first dye-labeled double stranded nucleic acid to a migration time of at least one fragment of the detectably labeled single stranded sizing ladder.

5. The method of claim 4, wherein the step of comparing a migration time of the first dye-labeled double stranded nucleic acid to the migration time of the at least one fragment of the detectably labeled single stranded sizing ladder further comprises comparing the first dye-labeled double stranded nucleic acid migration time to a plurality of fragment migration times of the detectably labeled single stranded sizing ladder.

6. The method of claim 4, wherein the converting step further comprises assigning a length of each first dye-labeled double stranded nucleic acid based on a correlation factor assigned to each fragment of the detectably labeled single stranded sizing ladder.

7. The method of claim 1, wherein the plurality of double stranded nucleic acids is ribonucleic acid having at least a partially double stranded structure.

8. The method of claim 1, wherein the first dye is configured to label at least a detectable portion of the plurality of double- stranded nucleic acids.

9. The method of claim 1, wherein the first dye is configured to substantially not label a single stranded nucleic acid.

10. The method of claim 1, wherein the mobility dependent separation conditions comprise no denaturing additive.

11. The method of claim 10, wherein the mobility dependent separation conditions are configured to substantially maintain the first dye label labeling each of the plurality of double stranded nucleic acids.

12. The method of claim 1, wherein the detectably labeled single stranded sizing ladder is labeled covalently by a second dye.

13. The method of claim 12, wherein the second dye is spectrally resolvable from the first dye.

14. The method of claim 1, further comprising obtaining quantification of the plurality of double stranded nucleic acids by correlating one or more areas under the curve of at least a first plurality of detected peaks of the plurality of first dye-labeled double stranded nucleic acids with at least one or more areas under the curve of a second plurality of detected peaks of the fragments of the detectably labeled sizing ladder.

15. The method of claim 14, wherein the at least first plurality of detected peaks of the plurality of first dye-labeled double stranded nucleic acids is all of the detected peaks of the plurality of first dye-labeled double stranded nucleic acids.

16. The method of claim 14, further comprising summing all of the correlated areas under the curve of the plurality of the first dye-labeled double stranded nucleic acids, thereby providing quantification for the plurality of double stranded nucleic acids.

17. A method of quantifying the amount of a plurality of double stranded
nucleic acids, the method comprising:
contacting the plurality of double stranded nucleic acids with a) a first dye, and b) a detectably labeled single stranded sizing ladder, under conditions wherein the first dye is configured to label a double stranded nucleic acid;
producing a mixture comprising a plurality of first dye-labeled double stranded nucleic acids and the detectably labeled single stranded sizing ladder;
migrating the mixture under mobility dependent separation conditions;
separating each of the plurality of first dye-labeled double stranded nucleic acids;
receiving fluorescence data related to the plurality of first-dye double stranded nucleic acids, wherein the fluorescence data includes intensity values over time;
identifying a peak within the fluorescence data;
determining an area of the peak; and
normalizing the area of the peak data to generate a relative concentration value of the double stranded nucleic acid labeled with the first dye.

18. A method of generating a calibration curve, the method comprising: receiving data related to:
migrating a plurality of double stranded nucleic acids labeled with a first dye under mobility dependent separation conditions, wherein the size of each of the double stranded nucleic acids is known,
migrating a plurality of detectably labeled single stranded reference nucleic acids under the mobility dependent separation conditions, wherein the size of each of the detectably labeled single stranded reference nucleic acids is known,
separating each of the plurality of double stranded nucleic acids labeled with the first dye and determining a migration time of each of the plurality of double stranded nucleic acids labeled with the first dye, and
separating each of the detectably labeled single stranded reference nucleic acids and determining a migration time of each of the detectably labeled single stranded reference nucleic acids;
interpolating, based on the determined migration times of the plurality of double stranded nucleic acids labeled with the first dye and determined migration times of the detectably labeled single stranded reference nucleic acids, correlated sizes of single stranded reference nucleic acids; and
generating a calibration curve relating double stranded nucleic acids labeled with the first dye and detectably labeled single stranded reference nucleic acids.

19. The method of claim 18, wherein the calibration curve is used to determine
a size of an unknown double stranded nucleic acid labeled with the first dye.

20. The method of claim 18, further comprising:
storing the calibration curve in memory.

* * * * *

UNITED STATES PATENT AND TRADEMARK OFFICE
CERTIFICATE OF CORRECTION

| | |
|---|---|
| PATENT NO. | : 10,913,944 B2 |
| APPLICATION NO. | : 15/542795 |
| DATED | : February 9, 2021 |
| INVENTOR(S) | : Berosik et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 671 days.

Signed and Sealed this
Tenth Day of January, 2023

Katherine Kelly Vidal
*Director of the United States Patent and Trademark Office*

SEQUENCE LISTING

```
<160> NUMBER OF SEQ ID NOS: 8

<210> SEQ ID NO 1
<211> LENGTH: 40
<212> TYPE: DNA
<213> ORGANISM: Artificial Sequence
<220> FEATURE:
<223> OTHER INFORMATION: PCR primer

<400> SEQUENCE: 1
tgtaaaacga cggccagtgc cctggaagga gaacaaaggc                           40

<210> SEQ ID NO 2
<211> LENGTH: 38
<212> TYPE: DNA
<213> ORGANISM: Artificial Sequence
<220> FEATURE:
<223> OTHER INFORMATION: PCR primer

<400> SEQUENCE: 2
caggaaacag ctatgacctg acccgagatg gtgcttga                             38

<210> SEQ ID NO 3
<211> LENGTH: 37
<212> TYPE: DNA
<213> ORGANISM: Artificial Sequence
<220> FEATURE:
<223> OTHER INFORMATION: PCR primer

<400> SEQUENCE: 3
tgtaaaacga cggccagtgc tgcctctgat ggcggac                              37

<210> SEQ ID NO 4
<211> LENGTH: 39
<212> TYPE: DNA
<213> ORGANISM: Artificial Sequence
<220> FEATURE:
<223> OTHER INFORMATION: PCR primer

<400> SEQUENCE: 4
caggaaacag ctatgaccgc cacactctgg agctggaca                            39

<210> SEQ ID NO 5
<211> LENGTH: 42
<212> TYPE: DNA
<213> ORGANISM: Artificial Sequence
<220> FEATURE:
```

```
<223> OTHER INFORMATION: PCR primer

<400> SEQUENCE: 5
tgtaaaacga cggccagtcc aacccttgtc cttaccagaa cg                42

<210> SEQ ID NO 6
<211> LENGTH: 42
<212> TYPE: DNA
<213> ORGANISM: Artificial Sequence
<220> FEATURE:
<223> OTHER INFORMATION: PCR primer

<400> SEQUENCE: 6
caggaaacag ctatgaccaa actgtgagtg gatccattgg aa                42

<210> SEQ ID NO 7
<211> LENGTH: 40
<212> TYPE: DNA
<213> ORGANISM: Artificial Sequence
<220> FEATURE:
<223> OTHER INFORMATION: PCR primer

<400> SEQUENCE: 7
tgtaaaacga cggccagttt cccacaggtc tctgctaggg               40

<210> SEQ ID NO 8
<211> LENGTH: 39
<212> TYPE: DNA
<213> ORGANISM: Artificial Sequence
<220> FEATURE:
<223> OTHER INFORMATION: PCR primer

<400> SEQUENCE: 8
caggaaacag ctatgaccca gtcagatcct agcgtcgag               39
```